United States Patent
Azuma et al.

(10) Patent No.: US 10,584,314 B2
(45) Date of Patent: Mar. 10, 2020

(54) METHOD FOR PREPARATION OF RETINAL GANGLION CELLS

(71) Applicants: NATIONAL CENTER FOR CHILD HEALTH AND DEVELOPMENT, Tokyo (JP); SENJU PHARMACEUTICAL CO., LTD., Osaka (JP)

(72) Inventors: Noriyuki Azuma, Tokyo (JP); Taku Tanaka, Tokyo (JP); Tadashi Yokoi, Tokyo (JP)

(73) Assignees: NATIONAL CENTER FOR CHILD HEALTH AND DEVELOPMENT, Tokyo (JP); SENJU PHARMACEUTICAL CO., LTD., Osaka-Shi (JP)

( * ) Notice: Subject to any disclaimer, the term of this patent is extended or adjusted under 35 U.S.C. 154(b) by 118 days.

(21) Appl. No.: 15/502,321

(22) PCT Filed: Aug. 7, 2015

(86) PCT No.: PCT/JP2015/072463
§ 371 (c)(1),
(2) Date: Feb. 7, 2017

(87) PCT Pub. No.: WO2016/021709
PCT Pub. Date: Feb. 11, 2016

(65) Prior Publication Data
US 2017/0191033 A1    Jul. 6, 2017

(30) Foreign Application Priority Data

Aug. 8, 2014  (JP) ................. 2014-162370
Nov. 12, 2014 (JP) ................. 2014-230157

(51) Int. Cl.
| | |
|---|---|
| C12N 5/00 | (2006.01) |
| C12N 5/079 | (2010.01) |
| C12N 15/09 | (2006.01) |
| C12Q 1/02 | (2006.01) |
| A61L 27/00 | (2006.01) |
| A61P 27/06 | (2006.01) |
| A61K 35/30 | (2015.01) |
| C12Q 1/6876 | (2018.01) |
| G01N 33/50 | (2006.01) |

(52) U.S. Cl.
CPC ............ *C12N 5/0621* (2013.01); *A61K 35/30* (2013.01); *A61L 27/00* (2013.01); *A61P 27/06* (2018.01); *C12N 15/09* (2013.01); *C12Q 1/02* (2013.01); *C12Q 1/6876* (2013.01); *G01N 33/5058* (2013.01); *C12N 2501/13* (2013.01); *C12N 2506/02* (2013.01); *C12N 2506/08* (2013.01); *C12N 2506/45* (2013.01); *C12Q 2600/136* (2013.01); *C12Q 2600/158* (2013.01)

(58) Field of Classification Search
CPC ............................ C12N 5/0621; C12N 5/0605
See application file for complete search history.

(56) References Cited

U.S. PATENT DOCUMENTS

2013/0040330 A1  2/2013 Sasai et al.
2014/0341864 A1  11/2014 Nakano et al.

FOREIGN PATENT DOCUMENTS

JP    2013-509859 A    3/2013
WO   WO 2013/077425 A1  5/2013

OTHER PUBLICATIONS

Takihara et al., "Dynamic image analysis of axonal flow of cultured retinal ganglion cell," Journal of Japanese Ophthalmological Society, vol. 115, special issue, p. 255, 02-151, Apr. 2011.
Nakano et al., "Self-Formation of Optic Cups and Storable Stratified Neural Retina from Human ESC's," Cell Stem Cell, vol. 10, pp. 771-785, Jun. 2012.
Meyer et al., "Optic Vesicle-like Structures Derivied from Human Pluripotent Stem Cells Facilitate a Customized Approach to Retinal Disease Treatment," Stem Cells, vol. 29, pp. 1206-1218, Jun. 2011.
Riazifar et al., "Chemically Induced Specification of Retinal Ganglion Cells From Human Embryonic and Induced Pluripotent Stem Cells," Stem Cells Translational Medicine, vol. 3, pp. 424-432, Feb. 2014.
Takihara et al., "Dynamic image analysis of axonal flow of cultured retinal ganglion cell," Journal of Japanese Opthalmological Society, vol. 115, special issue, p. 02-151, Apr. 2011.
Otori et al., "Neuronal cell death and retinal disease," Igaku No Ayumi, vol. 189, No. 4, pp. 219-222, Apr. 1999.
International Search Report dated Oct. 27, 2015 in application No. PCT/JP2015/072463.

(Continued)

*Primary Examiner* — Marcia S Noble
(74) *Attorney, Agent, or Firm* — Foley & Lardner LLP

(57) ABSTRACT

An object of the present invention is to provide a method of inducing pluripotent stem cells to differentiate into clinically applicable retinal ganglion cells.

The present invention provides a method for inducing pluripotent stem cells to differentiate into retinal ganglion cells that can be used for clinical application. Such method is a method for producing retinal ganglion cells with elongated axons comprising the following steps: (a) a step of inducing pluripotent stem cells to differentiate into retinal progenitor cells via floating culture; (b) a step of inducing the retinal progenitor cells obtained in step (a) to differentiate into retinal ganglion cells via floating culture; and (c) a step of allowing axons to elongate via adhesion culture of the retinal ganglion cells obtained in step (b).

4 Claims, 32 Drawing Sheets
Specification includes a Sequence Listing.

(56) References Cited

OTHER PUBLICATIONS

Bosco et al., "BDNF and NT-4 Differentially Modulate Neurite Outgrowth in Developing Retinal Ganglion Cells," Journal of Neuroscience Research, vol. 57, No. 6, (Sep. 1999), pp. 759-769.
Gill et al., "Methods of Retinal Ganglion Cell Differentiation From Pluripotent Stem Cells," Translational Vision Science & Technology, vol. 3, No. 4, (Jul. 2014), pp. 1-13.
Tanaka et al., "Generation of Retinal Ganglion Cells with Functional Axons from Human Induced Pluripotent Stem Cells," Scientific Reports, vol. 5, No. 8344, (Feb. 2015), pp. 1-11.

Optic vesicle (hiPS cells/24 days after initiation of differentiation induction)

Embryoid body (hiPS cells/40 days after
initiation of differentiation induction)

Embryoid body (hiPS cells/40 days after initiation of differentiation induction)

Embryoid body (mES cells/18 days after
initiation of differentiation induction)

Embryoid body (mES cells/18 days after
initiation of differentiation induction)

A

B

A

Semaphorin 3A
(Sema3A)

Axonal growth suppression

Control

B

A

Embryoid body (hES cells/30 days after initiation of differentiation induction)

B

A

Embryoid body (miPS cells/22 days after initiation of differentiation induction)

B

Fig. 31-1
A. Adhesion
Day 18      Day 27      Day 35
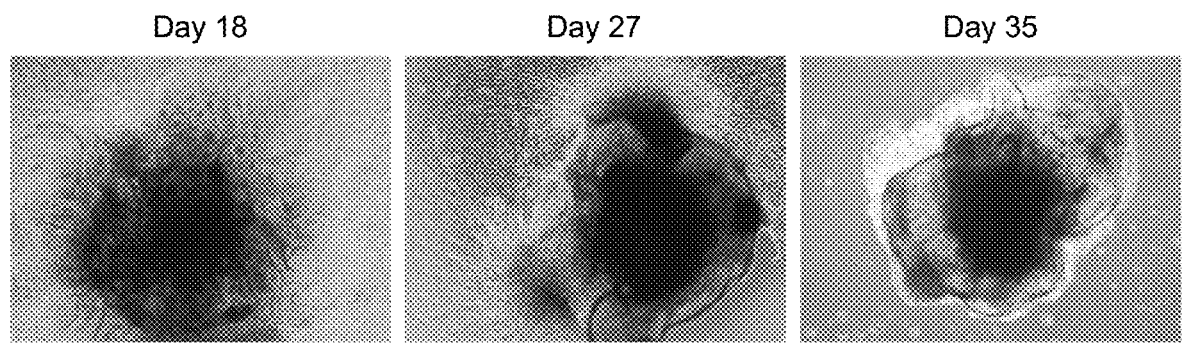
B. Medium level
400 μl      250 μl
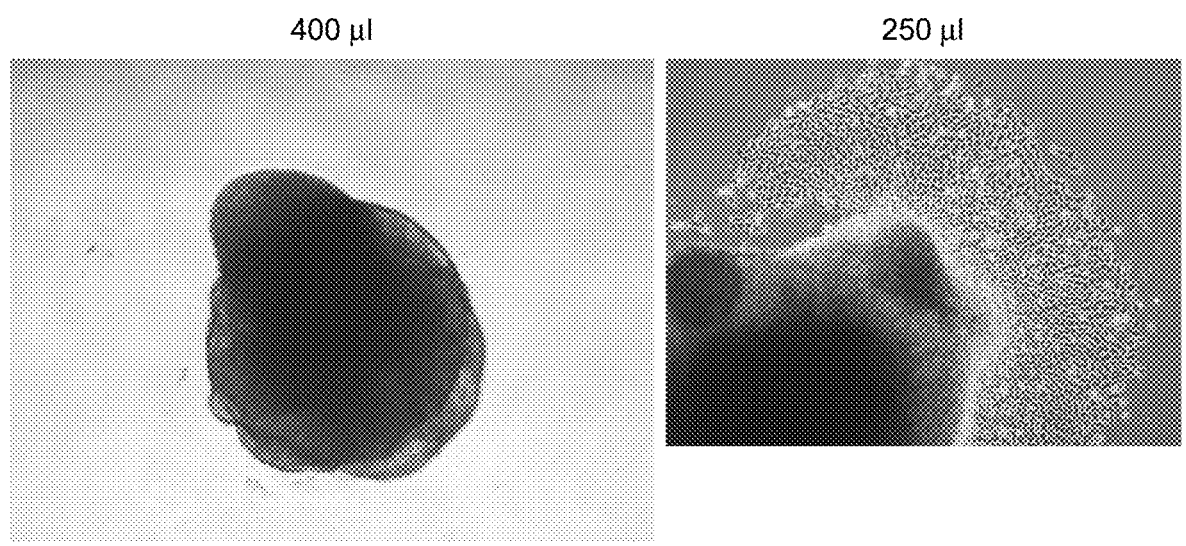
C. Optic vesicle cleavage
Cleaved      Not cleaved
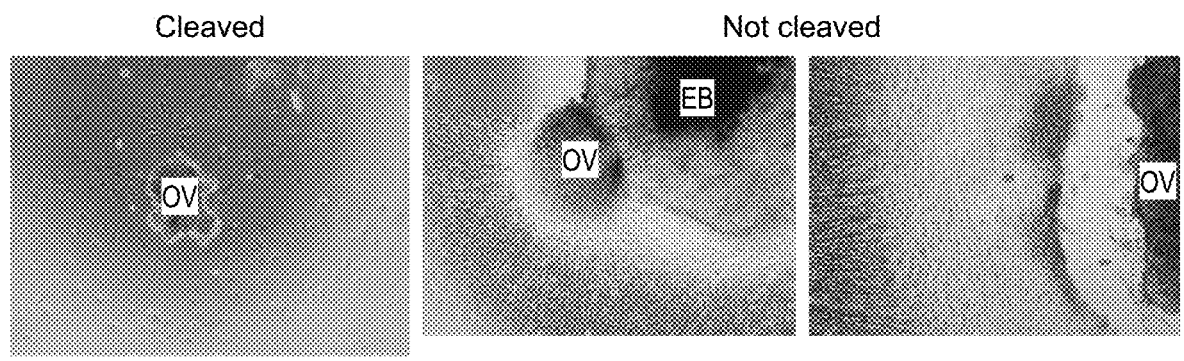

Fig. 31-2
D. BDNF addition
BDNF (+)      (-)
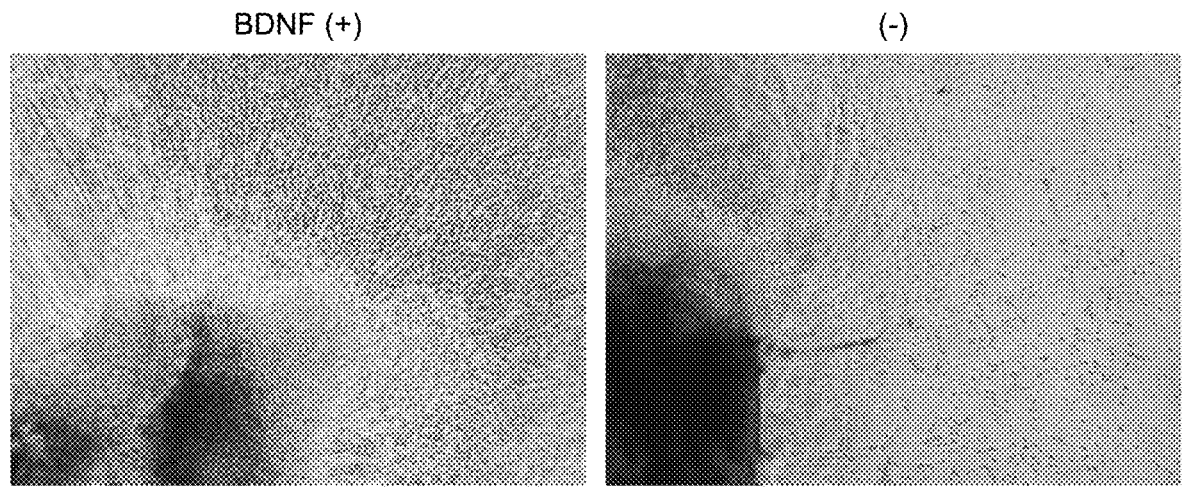
E. Retinoic acid (RA) addition
RA (+)      (-)
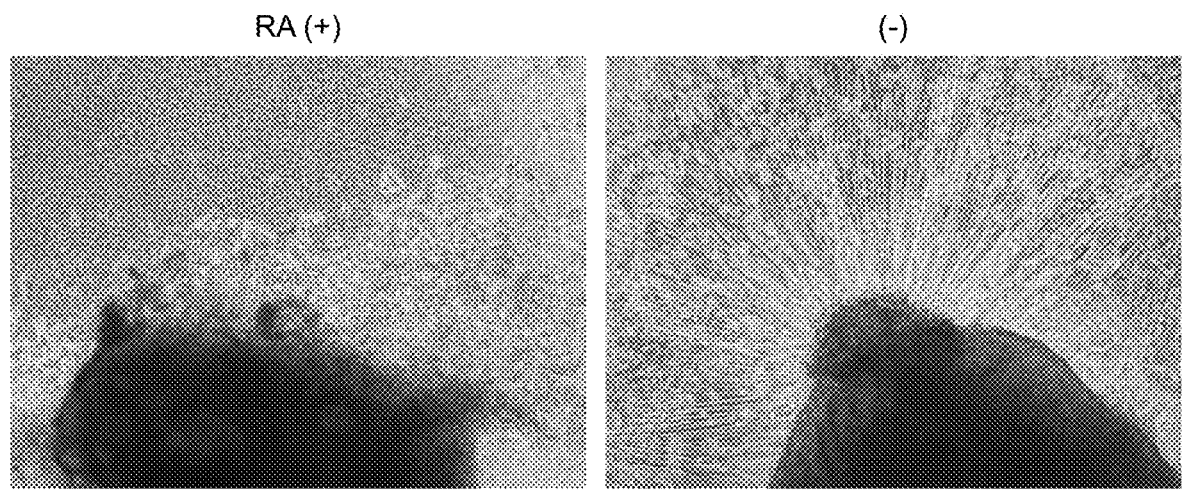
F. Oxygen concentration
High $O_2$: 40%      Normal (indoor) $O_2$
Day 27      Day 27
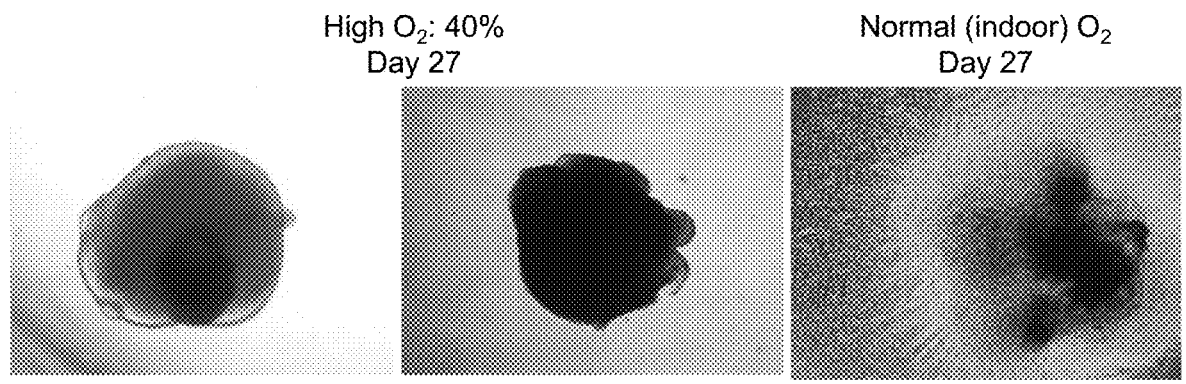

SEQUENCE LISTING

```
<160> NUMBER OF SEQ ID NOS: 64

<210> SEQ ID NO 1
<211> LENGTH: 24
<212> TYPE: DNA
<213> ORGANISM: Artificial
<220> FEATURE:
<223> OTHER INFORMATION: primer

<400> SEQUENCE: 1
tgacacatga gcgctctcac ttac                                          24

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
accaagtggc aaatgcacct a                                             21

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ccgtccctaa gcgtgctttc                                               20

<210> SEQ ID NO 4
<211> LENGTH: 25
<212> TYPE: DNA
<213> ORGANISM: Artificial
<220> FEATURE:
<223> OTHER INFORMATION: primer
```

```
<400> SEQUENCE: 4
actgggagct tcactaattt gctca                                          25

<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
tttaaagatc ctggaggtgg acata                                          25

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gctcaggtgc tcgggttcta                                                20

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
atcgtctccc agagtaagag c                                              21

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
cacgggatgg tgttcatgg                                                 19

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
cgacgttcac cacttaccaa                                                20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
tcggttctgg aaccatacct                                                20

<210> SEQ ID NO 11
```

```
<211> LENGTH: 21
<212> TYPE: DNA
<213> ORGANISM: Artificial
<220> FEATURE:
<223> OTHER INFORMATION: primer

<400> SEQUENCE: 11
taccagtgtc taccagccaa t                                         21

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
tgcacgagta tgaggaggtc t                                         21

<210> SEQ ID NO 13
<211> LENGTH: 25
<212> TYPE: DNA
<213> ORGANISM: Artificial
<220> FEATURE:
<223> OTHER INFORMATION: primer

<400> SEQUENCE: 13
ggcagtataa tccaaagatg gtcaa                                     25

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
gtcaagggca tatcctacaa caaac                                     25

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ccgtccctaa gcgtgctttc                                           20

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
actgggagct tcactaattt gctca                                     25

<210> SEQ ID NO 17
<211> LENGTH: 25
<212> TYPE: DNA
<213> ORGANISM: Artificial
<220> FEATURE:
<223> OTHER INFORMATION: primer

<400> SEQUENCE: 17
```
tttaaagatc ctggaggtgg acata                                     25

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gctcaggtgc tcgggttcta                                           20

<210> SEQ ID NO 19
<211> LENGTH: 23
<212> TYPE: DNA
<213> ORGANISM: Artificial
<220> FEATURE:
<223> OTHER INFORMATION: primer

<400> SEQUENCE: 19
aacccaatct ggctggtaaa tga                                       23

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
cagcaggccc ttaatgcgta                                           20

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
gcagaagacg cattgcttca a                                         21

<210> SEQ ID NO 22
<211> LENGTH: 19
<212> TYPE: DNA
<213> ORGANISM: Artificial
<220> FEATURE:
<223> OTHER INFORMATION: primer

<400> SEQUENCE: 22
gttcgcgttt cttgctggg                                            19

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
tgacacatga gcgctctcac ttac                                      24

<210> SEQ ID NO 24
<211> LENGTH: 21
<212> TYPE: DNA

<213> ORGANISM: Artificial
<220> FEATURE:
<223> OTHER INFORMATION: primer

<400> SEQUENCE: 24
accaagtggc aaatgcacct a                                        21

<210> SEQ ID NO 25
<211> LENGTH: 23
<212> TYPE: DNA
<213> ORGANISM: Artificial
<220> FEATURE:
<223> OTHER INFORMATION: primer

<400> SEQUENCE: 25
accctgatct ctagagccca caa                                      23

<210> SEQ ID NO 26
<211> LENGTH: 22
<212> TYPE: DNA
<213> ORGANISM: Artificial
<220> FEATURE:
<223> OTHER INFORMATION: primer

<400> SEQUENCE: 26
cttaatgtcc cagaacccag ca                                       22

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
taaagagcat cgagcagtcc a                                        21

<210> SEQ ID NO 28
<211> LENGTH: 23
<212> TYPE: DNA
<213> ORGANISM: Artificial
<220> FEATURE:
<223> OTHER INFORMATION: primer

<400> SEQUENCE: 28
gacatgacct ccacaaactt tct                                      23

<210> SEQ ID NO 29
<211> LENGTH: 22
<212> TYPE: DNA
<213> ORGANISM: Artificial
<220> FEATURE:
<223> OTHER INFORMATION: primer

<400> SEQUENCE: 29
tccagggaat caaaatgtgt gg                                       22

<210> SEQ ID NO 30
<211> LENGTH: 22
<212> TYPE: DNA
<213> ORGANISM: Artificial
<220> FEATURE:
<223> OTHER INFORMATION: primer

<400> SEQUENCE: 30
gcacagatcc ttcagtaaag ca                                       22

<210> SEQ ID NO 31
<211> LENGTH: 22
<212> TYPE: DNA
<213> ORGANISM: Artificial
<220> FEATURE:
<223> OTHER INFORMATION: primer

<400> SEQUENCE: 31
acaaccttcc aacaaccttg ac                                              22

<210> SEQ ID NO 32
<211> LENGTH: 19
<212> TYPE: DNA
<213> ORGANISM: Artificial
<220> FEATURE:
<223> OTHER INFORMATION: primer

<400> SEQUENCE: 32
ccttcctgtc ggcaagcat                                                  19

<210> SEQ ID NO 33
<211> LENGTH: 23
<212> TYPE: DNA
<213> ORGANISM: Artificial
<220> FEATURE:
<223> OTHER INFORMATION: primer

<400> SEQUENCE: 33
ccctaaattt gggcaagtga aga                                             23

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
caaagcaact cacgtgcaat c                                               21

<210> SEQ ID NO 35
<211> LENGTH: 22
<212> TYPE: DNA
<213> ORGANISM: Artificial
<220> FEATURE:
<223> OTHER INFORMATION: primer

<400> SEQUENCE: 35
agagtctgaa gcaagagcac tg                                              22

<210> SEQ ID NO 36
<211> LENGTH: 24
<212> TYPE: DNA
<213> ORGANISM: Artificial
<220> FEATURE:
<223> OTHER INFORMATION: primer

<400> SEQUENCE: 36
tgcggtcatt tatgttaaat cttc                                            24

<210> SEQ ID NO 37
<211> LENGTH: 19
<212> TYPE: DNA
<213> ORGANISM: Artificial
<220> FEATURE:

```
<223> OTHER INFORMATION: primer

<400> SEQUENCE: 37
ggccaagggt cactacacg                                                19

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38
gcagtcgcag ttttcacact c                                             21

<210> SEQ ID NO 39
<211> LENGTH: 23
<212> TYPE: DNA
<213> ORGANISM: Artificial
<220> FEATURE:
<223> OTHER INFORMATION: primer

<400> SEQUENCE: 39
gcggagtgta atcagtattt gga                                           23

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
gcatttgatc ccgtacaacc t                                             21

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
tgagcagcgt caacactgtg                                               20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
gaggtgaccg cgatgttctc                                               20

<210> SEQ ID NO 43
<211> LENGTH: 21
<212> TYPE: DNA
<213> ORGANISM: Artificial
<220> FEATURE:
<223> OTHER INFORMATION: primer

<400> SEQUENCE: 43
ccaagtgtgg ctcattaggc a                                             21
```

```
<210> SEQ ID NO 44
<211> LENGTH: 22
<212> TYPE: DNA
<213> ORGANISM: Artificial
<220> FEATURE:
<223> OTHER INFORMATION: primer

<400> SEQUENCE: 44
ccaatcttcg actggactct gt                                                    22

<210> SEQ ID NO 45
<211> LENGTH: 24
<212> TYPE: DNA
<213> ORGANISM: Artificial
<220> FEATURE:
<223> OTHER INFORMATION: primer

<400> SEQUENCE: 45
tcaacgtgaa gatggctttg gata                                                  24

<210> SEQ ID NO 46
<211> LENGTH: 23
<212> TYPE: DNA
<213> ORGANISM: Artificial
<220> FEATURE:
<223> OTHER INFORMATION: primer

<400> SEQUENCE: 46
aagacctggg agctctggga gta                                                   23

<210> SEQ ID NO 47
<211> LENGTH: 22
<212> TYPE: DNA
<213> ORGANISM: Artificial
<220> FEATURE:
<223> OTHER INFORMATION: primer

<400> SEQUENCE: 47
acaaccacga cctcagcagc ta                                                    22

<210> SEQ ID NO 48
<211> LENGTH: 22
<212> TYPE: DNA
<213> ORGANISM: Artificial
<220> FEATURE:
<223> OTHER INFORMATION: primer

<400> SEQUENCE: 48
atgacgagcc atttcccact tt                                                    22

<210> SEQ ID NO 49
<211> LENGTH: 21
<212> TYPE: DNA
<213> ORGANISM: Artificial
<220> FEATURE:
<223> OTHER INFORMATION: primer

<400> SEQUENCE: 49
cagctgcgag aataccagga c                                                     21

<210> SEQ ID NO 50
<211> LENGTH: 25
<212> TYPE: DNA
<213> ORGANISM: Artificial
<220> FEATURE:
<223> OTHER INFORMATION: primer
```

<400> SEQUENCE: 50
cacctttatg tgagtggaca cagag                                  25

<210> SEQ ID NO 51
<211> LENGTH: 21
<212> TYPE: DNA
<213> ORGANISM: Artificial
<220> FEATURE:
<223> OTHER INFORMATION: primer

<400> SEQUENCE: 51
cccgagaggt cttttccga g                                       21

<210> SEQ ID NO 52
<211> LENGTH: 21
<212> TYPE: DNA
<213> ORGANISM: Artificial
<220> FEATURE:
<223> OTHER INFORMATION: primer

<400> SEQUENCE: 52
ccagcccatg atggttctga t                                      21

<210> SEQ ID NO 53
<211> LENGTH: 22
<212> TYPE: DNA
<213> ORGANISM: Artificial
<220> FEATURE:
<223> OTHER INFORMATION: primer

<400> SEQUENCE: 53
catggaagcg aatcaatgga ct                                     22

<210> SEQ ID NO 54
<211> LENGTH: 21
<212> TYPE: DNA
<213> ORGANISM: Artificial
<220> FEATURE:
<223> OTHER INFORMATION: primer

<400> SEQUENCE: 54
ctgtaccaga ccgagatgtc a                                      21

<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
ctccccaaac ttgctttatg                                        20

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
aagaccccag agcattgtta                                        20

<210> SEQ ID NO 57
<211> LENGTH: 19

```
<212> TYPE: DNA
<213> ORGANISM: Artificial
<220> FEATURE:
<223> OTHER INFORMATION: primer

<400> SEQUENCE: 57
ggtggggtca tgtgtgtgg                                               19

<210> SEQ ID NO 58
<211> LENGTH: 22
<212> TYPE: DNA
<213> ORGANISM: Artificial
<220> FEATURE:
<223> OTHER INFORMATION: primer

<400> SEQUENCE: 58
cggttcaggt actcagtcat cc                                           22

<210> SEQ ID NO 59
<211> LENGTH: 22
<212> TYPE: DNA
<213> ORGANISM: Artificial
<220> FEATURE:
<223> OTHER INFORMATION: primer

<400> SEQUENCE: 59
cgattccgaa gatgtttcct cc                                           22

<210> SEQ ID NO 60
<211> LENGTH: 21
<212> TYPE: DNA
<213> ORGANISM: Artificial
<220> FEATURE:
<223> OTHER INFORMATION: primer

<400> SEQUENCE: 60
atctgggtag tgggcttcat t                                            21

<210> SEQ ID NO 61
<211> LENGTH: 21
<212> TYPE: DNA
<213> ORGANISM: Artificial
<220> FEATURE:
<223> OTHER INFORMATION: primer

<400> SEQUENCE: 61
atcaccccta cctcccttc c                                             21

<210> SEQ ID NO 62
<211> LENGTH: 19
<212> TYPE: DNA
<213> ORGANISM: Artificial
<220> FEATURE:
<223> OTHER INFORMATION: primer

<400> SEQUENCE: 62
cgaagagcct ctgcccata                                               19

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
```

| | |
|---|---|
| aggcctattt tgccgtacaa | 20 |

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64

| | |
|---|---|
| cgtctcacac cctcctcagt | 20 |

METHOD FOR PREPARATION OF RETINAL GANGLION CELLS

TECHNICAL FIELD

The present invention relates to a method for preparation of retinal ganglion cells, more particularly, a method for preparation of retinal ganglion cells comprising inducing pluripotent stem cells to differentiate into retinal ganglion cells with elongated axons.

BACKGROUND ART

At present, glaucoma is acknowledged as a major cause of blindness in developed countries. According to World Health Statistics 2002, the number of patients with blindness was 37,000,000 worldwide on the basis of the WHO standard, and 12% of such patients (i.e., 4,500,000 patients) suffer from glaucoma-induced blindness. In Japan, about 20% of visual impairment cases are caused by glaucoma, which is the leading cause of blindness. According to survey results, in addition, about 5% of the population aged 40 and older has been afflicted with glaucoma in Japan. It is also known that the prevalence rate of glaucoma increases with age. In the years to come after the arrival of an aging society, accordingly, the number of patients is deduced to be increasing. Since the clinical condition of glaucoma is retinal ganglion cell death caused by optic-disc cupping, treatment thereof is concentrated on the protection of retinal ganglion cells. The initial means for retinal ganglion cell protection is to lower intraocular pressure, and lowering of intraocular pressure with the use of eye drops is the first option for glaucoma treatment. While eye drops are effective for the lowering of intraocular pressure to a certain extent, the lowering of intraocular pressure is often insufficient to stop the progression of glaucoma. In addition, eye drops merely prevent progression, and use of eye drops would not lead to radical treatment.

Accordingly, there is urgent need for the establishment of cell replacement therapy that enables radical treatment of ocular diseases caused by retinal ganglion cell death, such as glaucoma, by preparing retinal ganglion cells and replacing the dead retinal ganglion cells with the prepared retinal ganglion cells. In the field of regenerative medical techniques that include such cell replacement therapy, the advancement in stem cell engineering has enabled induction of ocular tissues or cells, such as retina and crystalline lens, from mouse or human ES or iPS cells. In the future, treatment of ocular diseases, including glaucoma, which were not possible to effectively treat in the past, is expected to become possible through implantation of such induced ocular tissues or cells.

In the past, several attempts had been made to induce pluripotent stem cells to differentiate into retinal tissues. For example, Non-Patent Document 1 describes that three-dimensional culture of human ES cells had led to regeneration of all layers of the retina. Non-Patent Document 1 describes that retinal ganglion cells were induced from human ES cells 30 days after the initiation of induction, retinal ganglion cells were identified in the inner layer of the retina as a result of immunostaining of Brn3b, which is a retinal ganglion cell marker, and the neuroepithelial cell of the retina was induced when culture was continued for 100 or more days. While all layers of the retina were successfully regenerated according to the method described in Non-Patent Document 1, axons connected to the retinal ganglion cells were not elongated. Non-Patent Document 2 describes a method of inducing retinal progenitor cells serving as cellular components constituting the retina by repeatedly subjecting iPS cells to three-dimensional culture and two-dimensional culture, preparing optic-vesicle-like structures, and continuously subjecting the prepared optic-vesicle-like structures to three-dimensional floating culture. According to the method described in Non-Patent Document 2, however, a retinal layer structure is not formed, the possibility of successfully inducing cellular components constituting the retina is low, and axons of retinal ganglion cells have not resulted in elongation. Non-Patent Document 1 describes a method for producing retinal-layer-specific neurons by allowing Notch signal pathway inhibitors to react with the retinal progenitor cells included in the retinal tissue induced to differentiate from the pluripotent stem cells via floating culture. However, although some cells observed in the produced retinal tissue were ganglion cells, a majority of such cells were visual cells.

When practicing regenerative medicine, completeness of the cells should be first taken into consideration. Even if the results of immunostaining on the retinal ganglion cell-specific markers are positive and expression of such marker genes is observed, it is highly unlikely that such cells would be applicable to treatment without axon elongation. That is, clinically applicable retinal nerve fiber layers with elongated axons have not yet been regenerated according to conventional techniques. In addition, such techniques are not practically satisfactory in terms of the rate of induction or the number of days until induction.

In the development of an agent for treatment of optic neuropathy of the retina represented by glaucoma, animal models of diseases, such as mouse models of hereditary high-tension glaucoma (DBA/2J mice), mouse models of drug-induced disorders, various gene knock-out mice, and mutant mice, have been established. However, such disease animal models are disadvantageous since breeding and management thereof are laborious, animal cells are significantly different from human cells, and evaluation of therapeutic effects of drugs may not be definite.

PRIOR ART DOCUMENTS

Patent Documents

Patent Document 1: WO 2013/077425

Non-Patent Documents

Non-Patent Document 1: Nakano, T., Ando, S., Takata, N., Kawada, M., Muguruma, K., Sekiguchi, K., Saito, K., Yonemura, S., Eiraku, M., and Sasai, Y., Self-formation of optic cups and storable stratified neural retina from human ESCs, Cell Stem Cell, 10, 771-785, 2012

Non-Patent Document 2: Meyer, J. S. et al., Optic vesicle-like structures derived from human pluripotent stem cells facilitate a customized approach to retinal disease treatment, Stem cells 29, 1206-1218, 2011

SUMMARY OF THE INVENTION

Problem to be Solved by the Invention

An object of the present invention is to provide a method of inducing pluripotent stem cells to differentiate into clinically applicable retinal ganglion cells.

Means for Solving the Problem

The present inventors have conducted concentrated studies in order to attain the above objects. As a result, they succeeded in obtaining retinal ganglion cells with axons elongated to 1 to 2 cm that can be used in practical clinical applications within a short period of time after differentiation induction has been initiated (e.g., within 40 days in the case of human stem cells) with high induction efficiency (e.g., about 90% or higher). Such retinal ganglion cells can be obtained by continuing floating culture of a cell mass induced to differentiate from pluripotent stem cells via floating culture while adjusting the blood serum level and the neural differentiation inducing factor, so as to accelerate differentiation thereof into nerve progenitor cells, subjecting the cultured cell mass to adhesion culture, and optimizing conditions for floating culture and adhesion culture (i.e., medium components and concentrations). In addition, such retinal ganglion cells were implanted into the recipient's retina, the cells survived in the retina, and axon elongation was observed therein. Further, it was found that all the marker molecules inherent to retinal ganglion cells or axons had been expressed in the retinal ganglion cells and that such axons had characteristic structures including various neurofilaments, Tau, and the like and had functions with respect to axonal flow (orthodromic flow and antidromic flow) and electrophysiological reactions (active potentials and active currents). That is, such retinal ganglion cells were found to be sufficiently useful as tools for screening for an agent for treatment of optic neuropathy of the retina. The present invention has been completed on the basis of such findings.

Specifically, the present invention includes the following.
(1) A method for producing retinal ganglion cells with elongated axons comprising:
  (a) a step of inducing pluripotent stem cells to differentiate into retinal progenitor cells via floating culture;
  (b) a step of inducing the retinal progenitor cells obtained in step (a) to differentiate into retinal ganglion cells via floating culture; and
  (c) a step of allowing axons to elongate via adhesion culture of the retinal ganglion cells obtained in step (b).
(2) The method according to (1), wherein the pluripotent stem cells are induced pluripotent stem cells (iPS cells) or embryonic stem cells (ES cells).
(3) The method according to (1) or (2), wherein the adhesion culture is carried out in a medium containing neurotrophic factors.
(4) The method according to any of (1) to (3), wherein the adhesion culture is carried out in a medium with a surface level that is the same as the height of the cells.
(5) A culture product of the retinal ganglion cells with elongated axons obtained by the method according to any of (1) to (4).
(6) A cell preparation containing the culture product of retinal ganglion cells according to (5).
(7) A cell sheet containing the culture product of retinal ganglion cells according to (5).
(8) A method for screening for a protective agent for a retinal nerve or a regenerative agent for a retinal nerve comprising bringing a test substance into contact with the culture product of retinal ganglion cells according to (5) and evaluating protective or regenerative effects of the test substance on retinal ganglion cells.
(9) A method for treating an eye disease involving retinal ganglion cell damage comprising administering a therapeutically effective amount of the culture product of retinal ganglion cells according to (5) to a mammalian animal.
(10) The method for treating an eye disease according to (9), wherein the eye disease involving retinal ganglion cell damage is selected from the group consisting of glaucomatous disease, hereditary optic atrophy, optic nerve hypoplasia, ischemic disorders, and retinal disease.
(11) The culture product of retinal ganglion cells according to (5), which is used for treatment of an eye disease involving retinal ganglion cell damage.
(12) The culture product according to (11), wherein the eye disease involving retinal ganglion cell damage is selected from the group consisting of glaucomatous disease, hereditary optic atrophy, optic nerve hypoplasia, ischemic disorders, and retinal disease.
(13) Use of the culture product of retinal ganglion cells according to (5) for producing a cell preparation used for treatment of an eye disease involving retinal ganglion cell damage.
(14) The use according to (13), wherein the eye disease involving retinal ganglion cell damage is selected from the group consisting of glaucomatous disease, hereditary optic atrophy, optic nerve hypoplasia, ischemic disorders, and retinal disease.

This patent application claims priority from Japanese Patent Application No. 2014-162370 filed on Aug. 8, 2014, and Japanese Patent Application No. 2014-230157 filed on Nov. 12, 2014, and it includes part or all of the contents as disclosed in the descriptions thereof.

Effects of the Invention

According to the method of the present invention, retinal ganglion cells with elongated axons that are applicable to actual clinical practice can be efficiently produced from pluripotent stem cells within a short period of time. In addition, such retinal ganglion cells can be produced in a simple manner without inserting a gene from the outside. The retinal ganglion cells produced by the method of the present invention can be used for cell replacement therapy that involves implantation of cells into the damaged site of a retinal nerve. The cell replacement therapy involving the use of the retinal ganglion cells is advantageous over conventional cell replacement therapy involving the use of retinal pigment epithelial cells, the clinical application of which to humans has already been initiated, or cell replacement therapy involving the use of visual cells, the application of which is expected in the future, for the following reasons. That is, retinal ganglion cells are present in the inner layer of the retina and in the vicinity of the vitreous cavity, and, accordingly, cells can be easily supplied. In addition, there is no risk of retinal detachment. With the use of such retinal ganglion cells, also, screening of a drug, such as an agent for glaucoma treatment (e.g., a "protective agent for the retinal nerve" that delays retinal nerve cell death or a "regenerative agent for the retinal nerve" that promotes plasticity or regeneration of the retinal nerve), can be carried out readily and rapidly in vitro. Accordingly, the time, labor, cost, and the like required for drug screening involving the use of experimental animals comprising breeding of experimental animals, preparation of pharmacological samples, and immunostaining can be reduced to a significant extent.

BRIEF DESCRIPTION OF THE DRAWINGS

FIG. 1 also shows phase-contrast micrographs of embryoid bodies at points after the initiation of differentiation induction (i.e., 6, 18, 24, and 30 days after initiation) (scale bar: 500 μm).

FIG. 11B: vertical plane; scale bar: 80 µm).

FIG. 16A shows a microscopic photograph of retinal ganglion cells stained with Lucifer yellow CH (triangular arrow: dendritic process; arrow: axonal process). FIG. 16B shows the records of action potentials of retinal ganglion cells (whole-cell recording). FIG. 16C shows the records of action potentials of retinal ganglion cells (upper panel: action potentials; middle panel: attenuation by tetrodotoxin; lower panel: recovery by washing; scale bar: 30 µm).

FIG. 30A shows an electron microscopic photograph of cells into which a patch-clamp electrode is implanted. FIG. 30B shows a microscopic photograph of retinal ganglion cells subjected to detection of electrophysiological reactions, followed by procion yellow staining. FIG. 30C shows the records of action potentials of retinal ganglion cells (whole-cell recording). FIG. 30D shows the records of action potentials of retinal ganglion cells (upper panel: action potentials; middle panel: attenuation by tetrodotoxin; lower panel: recovery by washing).

FIG. 31-1 shows the results of comparison of conditions for inducing human iPS cells to differentiate into retinal ganglion cells (A: day of transition to adhesion culture (Day 18, Day 27, and Day 35; B: amount of medium used for adhesion culture (250 µl and 400 µl); C: whether or not the optic vesicle is cleaved from the embryoid body at the time of adhesion).

FIG. 31-2 shows the results of comparison of conditions for inducing human iPS cells to differentiate into retinal ganglion cells (D: with or without the addition of neurotrophic factors (BDNF) (+, −); E: with or without the addition of retinoic acid (RA) (+, −); F: oxygen concentration at the time of floating culture).

EMBODIMENTS FOR CARRYING OUT THE INVENTION

Figure 1:
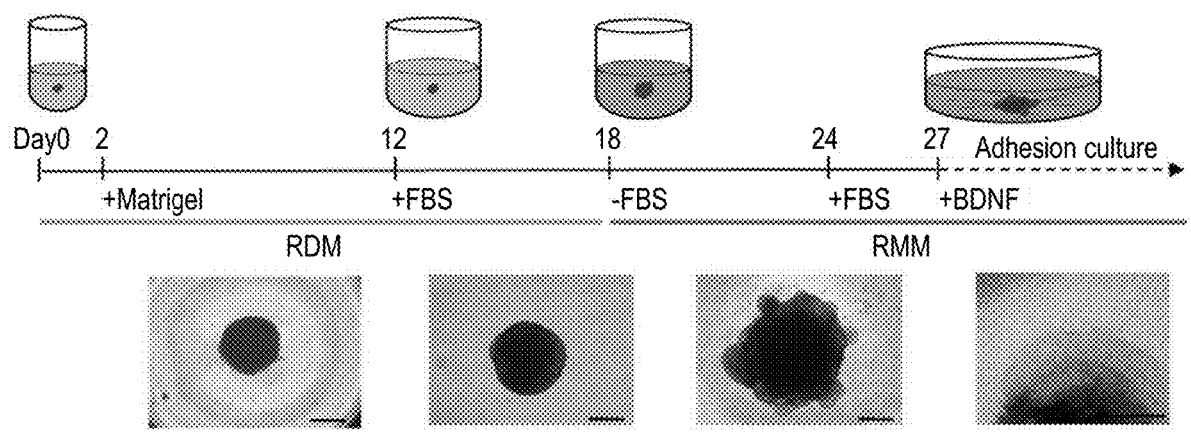
FIG. 1 schematically shows a method of inducing human iPS (hiPS) cells to differentiate into retinal ganglion cells.

Hereafter, the present invention is described in detail.
1. Method for Producing Retinal Ganglion Cells with Elongated Axons The present invention concerns a method for producing retinal ganglion cells with elongated axons comprising: (a) a step of inducing pluripotent stem cells to differentiate into retinal progenitor cells via floating culture; (b) a step of inducing the retinal progenitor cells obtained in step (a) to differentiate into retinal ganglion cells via floating culture; and (c) a step of allowing axons to elongate via adhesion culture of the retinal ganglion cells obtained in step (b).

In the present invention, the term "pluripotent stem cells" refers to stem cells that have the potential to differentiate into any cells existing in organisms derived from ectoblasts, mesoblasts, and endoblasts (i.e., pluripotency) and also have growth capacity. Examples of pluripotent stem cells that are used in the present invention include induced pluripotent stem cells (iPS cells), embryonic stem cells (ES cells), somatic stem cells (tissue-specific stem cells), cloned embryo-derived embryonic stem cells obtained by nuclear transfer (ntES cells), germ-line stem cells (GS cells), embryonic germ cells (EG cells), and pluripotent adult progenitor cells (MAPC cells), with iPS cells and ES cells being preferable.

Pluripotent stem cells that are used in the present invention are preferably derived from mammalian animals. Examples of mammalian animals include humans, monkeys, mice, rats, hamsters, guinea pigs, rabbits, dogs, cats, sheeps, pigs, and cows.

The term "induced pluripotent stem cells (iPS cells)" used herein refers to artificial stem cells derived from somatic cells having pluripotency and growth capacity via autoreplication equivalent to those of embryonic stem (ES) cells that can be produced by introducing particular reprogramming (initialization) factors into somatic cells, such as skin cells, in the form of DNAs or proteins.

At first, iPS cells were established by Yamanaka et al. by introducing four factors (i.e., OCT3/4, SOX2, KLF4, and C-MYC) into mouse fibroblasts (K. Takahashi and S. Yamanaka, 2006, Cell, 126: 663-676). Thereafter, human iPS cells were also established by introducing the same four factors into human fibroblasts (K. Takahashi et al., 2007, Cell, 131: 861-872). In addition, iPS cells are successfully established by, for example, a method in which, among the four factors, C-MYC is excluded (M. Nakagawa et al., 2008, Nat. Biotechnol., 26: 101-106), a method in which some of the four factors are replaced with other factors, and a method in which another factor is (or other factors are) added, in addition to the four factors (e.g., J. Yu et al., 2007, Science, 318: 1917-1920).

Such reprogramming (initialization) factors may be introduced into somatic cells by techniques such as lipofection, binding to cell-permeable peptides, or microinjection, in the form of proteins. Alternatively, such factors may be introduced into somatic cells by techniques such as a method involving the use of vectors, such as virus, plasmid, or artificial chromosome vectors, lipofection, a method involving the use of liposomes, or microinjection, in the form of DNAs. Examples of virus vectors include retrovirus vectors, lentivirus vectors, adenovirus vectors, adeno-associated virus vectors, and Sendai virus vectors. Examples of artificial chromosome vectors include human artificial chromosome (HAC) vectors, yeast artificial chromosome (YAC) vectors, and bacterial artificial chromosome (BAC and PAC) vectors. Plasmids for mammalian cells can be used, and vectors can contain control sequences, such as promoters, enhancers, ribosome-binding sequences, terminators, and polyadenylation sites, so that initiation factors can be expressed. According to need, selection marker sequences, such as drug tolerant genes (e.g., kanamycin tolerant genes, ampicillin tolerant genes, and puromycin tolerant genes), thymidine kinase genes, and diphtheria toxin genes, and reporter gene sequences, such as green fluorescent proteins (GFP), β-glucuronidase (GUS), and FLAG, can be contained.

Also, the vector may comprise a LoxP sequence at each terminus of a gene encoding the reprogramming factor or a gene encoding a reprogramming factor that binds to a promoter, so as to cleave such gene after it has been introduced into the somatic cells.

The "iPS cells" used in the present invention are not particularly limited in terms of, for example, the origin thereof, initialization factors to be introduced, and methods of introduction. Within the scope of the present invention, any iPS cells that are produced by known techniques can be used. The origin is preferably a human, and it is more preferably derived from a patient who requires the retinal ganglion cells induced to differentiate from such iPS cells.

The "iPS cells" used in the present invention may be produced in accordance with a technique known in the art. Alternatively, such iPS cells are available from public institutions, such as the Riken BioResource Center (RIKEN BRC).

The term "embryonic stem cells (ES cells)" used in the present invention refers to stem cells having pluripotency and growth capacity by autoreplication established from embryoblasts of early embryos (e.g., blastocysts) of mammalian animals, such as humans or mice.

While ES cells are preferably derived from mammalian animals as described above, mouse-derived ES cells are preferably used from the viewpoint of availability. Human-derived ES cells are preferably used for treatment of humans.

ES cells that are provided by public institutions or commercialized can be used. Examples of mouse-derived ES cells include C57/BL6 cells, EB3 cells, E14 cells, D3 cells, CCE cells, R1 cells, 129SV cells, J1 cells, and RF8 cells, and such cells are available from, for example, the Riken BioResource Center (RIKEN BRC), American Type Culture Collection (ATCC), or Sumitomo Dainippon Pharma Co., Ltd. (Osaka, Japan). Human ES cells are available from, for example, the Stem Cell Research Center, the Institute for Frontier Medical Sciences, Kyoto University, and the WiCell Research Institute (Madison, U.S.A.).

The term "embryoid body (EB)" used in the present invention refers to a cell aggregate (a cell mass) formed via culture of pluripotent stem cells. In addition, the term refers to any form of cell mass, such as a cell mass including retinal progenitor cells, a cell mass including retinal ganglion cells, and a cell mass including retinal ganglion cells with elongated axons.

The "retinal ganglion cells with elongated axons" produced from pluripotent stem cells by the method of the present invention are characterized by axon elongation and Brn3b, which is a marker specific therefor. Retinal ganglion cells are a type of cell constituting the retina. In the retina of an organism, visual cells, horizontal cells, bipolar cells, amacrine cells, ganglion cells, and Muller cells are arranged in laminae in such order from the outside toward the inside. When "axons are elongated" herein, a long axon is elongated from a retinal ganglion cell body, and axons elongated from cells are arranged so as to be oriented in the same direction.

The "retinal ganglion cells with elongated axons" produced from pluripotent stem cells by the method of the present invention are provided in the form of a culture product containing the same. In such culture product, the retinal ganglion cells with elongated axons preferably account for 80% or more, more preferably 85% or more, further preferably 90% or more, and most preferably 95% or more of a cell mass.

Hereafter, the method for preparation of retinal ganglion cells of the present invention is described in detail.
Step (a):
In Step (a), pluripotent stem cells are induced to differentiate into retinal progenitor cells via floating culture.

When iPS cells or ES cells used as the pluripotent stem cells are to be maintained, culture may be carried out with the use of an adequate medium (e.g., a commercially available iPS cell culture medium or a commercially available ES cell culture medium) on feeder cells, such as mouse embryonic fibroblast (MEF) cells, SNL, or SNLP.

The "retinal progenitor cells" obtained in Step (a) can differentiate into any of matured retinal cells selected from among visual cells, horizontal cells, bipolar cells, amacrine cells, and ganglion cells.

"Floating culture" conducted in Step (a) is three-dimensional culture that is conducted under non-adherent conditions with respect to the culture vessel, and such culture is preferably aggregation floating culture. By conducting aggregation floating culture, a pluripotent stem cell aggregate can be formed, and such cell mass can be induced to differentiate into target cells. Aggregation floating culture can be carried out by serum-free floating culture of embryoid body-like aggregates (SFEB; Watanabe, K., Sasai, Y. et. al., 2005, Nature Neuroscience 8 (3), 288-296), culture of embryoid bodies (Keller et al., 1995, Curr. Opin. Cell Biol., 7, 862-869), or another technique modified therefrom. It is preferable that culture of embryoid bodies be conducted via SFBE, such as in a serum-free medium.

A culture vessel used for floating culture is not particularly limited, and examples thereof include flasks, dishes, microplates, chambers, tubes, and roller bottles. Floating culture is preferably carried out in a non-cell-adhesive vessel. Accordingly, it is preferable that a culture vessel be made of a hydrophobic material or be coated with a coating agent aimed at preventing cells from adsorbing to the surface (e.g., a polyhydroxyethyl methacrylate copolymer).

Conditions of floating culture, such as culture temperature and $CO_2$ concentration, can be adequately determined in accordance with the type of stem cells used. For example, culture temperature is about 30° C. to 40° C., and preferably about 37° C., and $CO_2$ concentration is about 1% to 10%, and preferably about 5%.

In principle, floating culture can be carried out in accordance with the serum-free floating culture of embryoid bodies-like aggregates with the quick (SFEBq) method, which is improved from the SFEB method described above with the addition of an Rho kinase inhibitor to the medium, in the case of human-derived pluripotent stem cells, although an adequate method varies depending on the type of pluripotent stem cells used.

The duration of culture (the number of days) in Step (a) varies depending on the type of pluripotent stem cells used. When the day on which culture was initiated is designated as Day 0 after the initiation of differentiation induction and the number of days is counted, for example, culture is conducted for up to 18 days after the initiation of differentiation induction in the case of human pluripotent stem cells, and culture is conducted for up to 7 days after the initiation of differentiation induction in the case of mouse pluripotent stem cells. It should be noted that such culture duration is merely an example, and it can be modified within 1 to 3 days from the number of days described above.

In the case of human pluripotent stem cells, more specifically, a pluripotent stem cell aggregate is first formed in a serum-free medium (Medium 1), the cell aggregate is cultured in a serum-free medium containing a basal membrane sample (Medium 2), and the resultant is further cultured in a serum medium containing a basal membrane sample (Medium 3). When the day on which culture was initiated is designated as Day 0 after the initiation of differentiation induction, culture in Medium 1 is conducted from Day 1 to Day 2 after the initiation of differentiation induction, culture in Medium 2 is conducted from Day 2 to Day 12 after the initiation of differentiation induction, and culture in Medium 3 is conducted from Day 12 to Day 18 after the initiation of differentiation induction. The culture duration in each medium may be adequately changed. In the case of mouse pluripotent stem cells, culture is conducted up to Day 7 after the initiation of differentiation induction only in a serum-free medium containing a basal membrane sample (Medium 2).

In the present invention, Medium 1, Medium 2, and Medium 3 used in Step (a) are each referred to as a "retinal differentiation medium." A retinal differentiation medium (RDM medium) used in Step (a) can be prepared using a medium used for animal cell culture as a basal medium. A basal medium is not particularly limited, provided that it contains ingredients necessary for cell survival (e.g., inorganic salts, amino acids, glucose, and vitamins) and it is known to a person skilled in the art. Examples of such basal medium include Dulbecco's Modified Eagle's Medium (D-MEM), Dulbecco's Modified Eagle's Medium/Nutrient Mixture F-12 (D-MEM/F-12), Glasgow MEM (G-MEM), Basal Medium Eagle (BME), Minimum Essential Medium (MEM), Eagle's minimal essential medium (EMEM), Iscove's Modified Dulbecco's Medium (IMDM), RPMI 1640 medium, Medium 199, αMEM medium, Ham medium, Fischer medium, and a mixture of any thereof.

A "serum-free medium" used as Medium 1 or 2 is a medium prepared without the addition of a non-adjusted or unpurified animal serum to the basal medium. A "serum-free medium" may contain a serum replacement. Examples of "serum replacement" include Knockout serum replacement (KSR), a collagen progenitor, albumin, transferrin, insulin, progesterone, putrescine, a trace element (e.g., sodium selenate), and a mixture of any thereof. Serum replacements that are generally used for culture of nervous system cells, such as KnockOut Serum Replacement™ (KSR, Invitrogen Corporation), N2 Supplements™ (Gibco), B27 Supplements™ (Gibco), and Chemically-Defined Lipid Concentrate (Gibco), are preferably used.

The "basal membrane sample" used for Medium 2 or 3 is a sample containing basal membrane components having functions of regulating, for example, configurations, differentiation, growth, movement, or expression of functions of cells, when particular cells having the capacity for basal membrane formation are sowed and cultured on such sample. As a basal membrane sample, commercial products containing known extracellular matrix molecules, such as laminin, type IV collagen, heparan sulfate proteoglycan, or entactin, as basal membrane components (e.g., Matrigel™, BD Bioscience) can be used. Concentration of a basal membrane sample in the medium is preferably about 0.1% to 5%, and more preferably about 0.5% to 2%, when, for example, Matrigel is used.

The "serum medium" used as Medium 3 is a medium prepared with the addition of an animal serum to the basal medium. For example, mammalian animal serum, such as bovine serum, fetal bovine serum, horse serum, or human serum, can be used. Serum concentration in the medium is preferably about 0.1% to 10%, more preferably about 1% to 10%, and further preferably about 1% to 5%.

Pluripotent stem cell density in the retinal differentiation medium used in Step (a) is not particularly limited, provided that a homogeneous pluripotent stem cell aggregate (a cell mass) is formed. When human pluripotent stem cells are subjected to floating culture using a 96-well microplate, for example, cell density is preferably about $1 \times 10^3$ to $3 \times 10^4$ cells/well, more preferably about $5 \times 10^3$ to $2 \times 10^4$ cells/well, and further preferably about $9 \times 10^3$ cells/well.

Also, ingredients necessary for differentiation induction, growth, and maintenance of cells may be added to the basal medium. Examples of such ingredients include nonessential amino acids, such as glycine, serine, and glutamine, glutamine replacements, such as GlutaMAX™, pyruvic acids, cytokines, such as growth factors, including FGF, PDGF, TGF-β, and EGF, reducing agents, such as 2-mercaptoethanol and 3'-thiol glycerol, antibiotics, such as streptomycin and penicillin, vitamins, such as ascorbic acid and d-biotin, buffers, such as HEPES, and antioxidants.

Examples of ingredients that are preferably used for differentiation induction in Step (a) include serum replacements, such as KSR, nonessential amino acids, 2-mercaptoethanol, and sodium pyruvate. As Medium 1, accordingly, use of a serum-free medium supplemented with an adequate amount of commercially available KSR (e.g., G-MEM or D-MEM supplemented with 0.1 mM 2-mercaptoethanol, 0.1 mM nonessential amino acid mix, and 1 mM sodium pyruvate) is preferable. KSR concentration in the serum-free medium is preferably about 1% to 20%, and more preferably about 10% to 20% when, for example, human iPS cells are used.

When pluripotent stem cells are derived from humans, a Rho-associated coiled-coil forming kinase (ROCK) inhibitor capable of suppressing cell death caused by dispersion is added to Medium 1. As a ROCK inhibitor (an Rho kinase inhibitor), for example, [R)-(+)-trans-N-(4-pyridyl)-4-(1-aminoethyl)-cyclohexanecarboxamide dihydrochloride] (Y-27632) and 1-(5-isoquinolinesulfonyl)homopiperazine dihydrochloride (Fasudil; HA-1077) are known (K. Watanabe et al., Nat. Biotech., 25: 681-686, 2007). Y-27632 is particularly preferable, and commercially available products (e.g., those manufactured by Wako Pure Chemical Industries, Ltd.) can be used. Concentration of the ROCK inhibitor in the medium is not particularly limited, provided that death of stem cells is suppressed and the viability is improved. It is preferably about 1 μM to 50 μM, and more preferably about 5 μM to 30 μM.

When pluripotent stem cells are derived from humans, a Wnt signal inhibitor is added to Medium 1. A Wnt signal inhibitor is not particularly limited, provided that it can suppress signal transmission mediated by Wnt. Examples thereof include IWR-1-endo (IWR-1e), IWP-2, Dkk1, Cerberus protein, Wnt receptor inhibitor, soluble Wnt receptor, and Wnt antibody. Concentration of the Wnt signal inhibitor in the medium is not particularly limited, provided that embryoid bodies of pluripotent stem cells can be formed. In the case of a general Wnt signal inhibitor, such as IWR-1e, it is preferably about 0.1 μM to 100 μM, and more preferably about 1 μM to 10 μM.

Medium 2 may be prepared with the addition of a basal membrane sample to Medium 1, or it may be prepared with the addition of a basal membrane sample to a fresh serum-free medium. It is preferable that the ROCK inhibitor be removed upon completion of culture in Medium 1.

Medium 3 is preferably a fresh medium prepared with the addition of serum to the serum-free medium described above (e.g., G-MEM or D-MEM supplemented with 0.1 mM 2-mercaptoethanol, 0.1 mM nonessential amino acid mix, and 1 mM sodium pyruvate).

When pluripotent stem cells are derived from humans, an Shh (sonic hedgehog) signal activator and a Wnt signal activator are added to Medium 3, so as to accelerate the growth of retinal progenitor cells (Rx-positive).

An Shh signal activator is not particularly limited, provided that it can potentiate signal transmission mediated by Shh. Examples of Shh signal activators include proteins that belong to the Hedgehog family (e.g., Shh), an Shh receptor, an Shh receptor agonist, Purmorphamine, and SAG. Concentration of the Shh signal activator in the medium is preferably about 0.1 nM to 10 μM, and more preferably about 10 nM to 1 μM, in the case of SAG, for example.

A representative example of a Wnt signal activator is a GSK3β inhibitor, and examples thereof include an indirubin derivative BIO (GSK-3β inhibitor IX; 6-bromoindirubin-3'-oxime), a maleimide derivative SB216763 (3-(2,4-dichlorophenyl)-4-(1-methyl-1H-indol-3-yl)-1H-pyrrole-2,5-dione), a phenyl α bromomethylketone compound GSK-3β inhibitor VII (4-dibromoacetophenone), CHIR99021, 6-[(2-{[4-(2,4-dichlorophenyl)-5-(4-methylimidazol-2-yl)pyrimidin-2-yl]amino}ethyl)amino]pyridine-3-carbonitrile (WO1999/65897), and cell-permeable phosphorylated peptide L803-mts (GSK-3β peptide inhibitor; Myr-N-GKEAPPAPPQSpP-NH$_2$). The concentration of the Wnt signal activator in the medium is preferably about 0.1 μM to 100 μM, and more preferably about 1 μM to 30 μM in the case of, for example, CHIR99021.

The Shh signal activator and the Wnt signal activator may be added simultaneously with the initiation of culture in Medium 3, or these activators may be added 2 to 3 days after the initiation of culture in Medium 3.

Whether or not pluripotent stem cells are induced to differentiate into retinal progenitor cells in Step (a) can be confirmed with the aid of a marker that is expressed specifically in the retinal progenitor cells. Examples of retinal progenitor cell markers include Rx, Pax6, Chx10, and Six3, one such marker may be used alone, or two or more such markers may be used in combination. Marker expression can be confirmed via immunostaining of marker proteins or assay of marker gene expression levels via RT-PCR.

Step (b):

In Step (b), the retinal progenitor cells obtained in Step (a) are further induced to differentiate into retinal ganglion cells via floating culture. In Step (b), retinal progenitor cells can be matured to result in retinal ganglion cells. In Step (b), the retinal progenitor cells obtained in Step (a) are subjected to floating culture in a serum-free medium (a serum-free retinal maturation medium), and the resultant is further cultured in a serum medium (a serum-containing retinal maturation medium). In the present invention, the serum-free retinal maturation medium and the serum-containing retinal maturation medium used in Step (b) are referred to as "retinal maturation media (RMM)." The duration of floating culture (the number of days) in Step (b) varies depending on the type of pluripotent stem cells used. In the case of human pluripotent stem cells, culture in the serum-free retinal maturation medium is conducted from Day 18 to Day 24 after the initiation of differentiation induction, and culture in the serum-containing retinal maturation medium is conducted from Day 24 to Day 26 after the initiation of differentiation induction. In the case of mouse pluripotent stem cells, culture in the serum-free retinal maturation medium is conducted from Day 7 to Day 10 after the initiation of differentiation induction, and culture in the serum-containing retinal maturation medium is conducted from Day 10 to Day 13 after the initiation of differentiation induction. It should be noted that the culture durations mentioned above are merely examples, and they can each be modified within 1 to 3 days from the numbers of days described above.

The basal medium described above can be used as the "retinal maturation medium." In Step (b), a basal medium is preferably D-MEM/F-12. A serum replacement may be added to the serum-free retinal maturation medium, and the serum replacements described above may be used, with N2 Supplements being preferable. Serum concentration is preferably about 0.1% to 1%, and more preferably about 0.5% to 1% in the serum-containing retinal maturation medium. Retinoic acid or the like is added as a neural differentiation inducing factor to the serum-containing retinal maturation medium.

Conditions of floating culture employed in Step (b), such as a culture vessel, culture temperature, and $CO_2$ concentration, are the same as those employed in Step (a). When conducting floating culture in Step (b), retinal progenitor cells are likely to differentiate into visual cells or pigment epithelia at a high oxygen concentration (40%). In general, accordingly, $O_2$ concentration is preferably atmospheric oxygen concentration (about 20%).

Whether or not retinal progenitor cells are induced to differentiate into retinal ganglion cells in Step (b) can be confirmed by detecting the expression of markers that are expressed specifically in retinal ganglion cells, such as Brn3b, Math5, Sncg, Islet1, or Tuj1, and it can be preferably confirmed by detecting the expression of Brn3b. Marker expression can be confirmed via, for example, immunostaining of marker proteins or assay of marker gene expression levels via RT-PCR.

Step (c):

In Step (c), the retinal ganglion cells obtained in Step (b) are further subjected to adhesion culture. In Step (c), retinal ganglion cells with elongated axons can be formed. At the time of transition from Step (b) to Step (c), optic-vesicle-like tissue is formed by a cell mass containing retinal ganglion cells; however, the cell mass can be subjected to adhesion culture in such state without cleavage thereof. Since differentiation becomes insufficient if optic-vesicle-like tissue is cleaved and subjected to adhesion culture, a cell mass is preferably subjected to adhesion culture without cleavage of the optic-vesicle-like tissue therefrom. In the present invention, a medium used in Step (c) is referred to as a "neuronal maintenance medium." Transition from floating culture into adhesion culture is implemented 26 to 30 days, and preferably 26 to 28 days, after the initiation of differentiation induction in the case of human pluripotent stem cells. In the case of mouse pluripotent stem cells, it is implemented 12 to 14 days after the initiation of differentiation induction. It should be noted that the times of transition mentioned above are merely examples, and they may vary within a range of 1 to 3 days each. The time of transition from floating culture to adhesion culture is critical. If such transition is carried out before or after the time mentioned above, the number of resulting retinal ganglion cells with elongated axons is reduced. In the case of human pluripotent stem cells, culture is conducted from 26 days to 40 days after the initiation of differentiation induction. In the case of mouse pluripotent stem cells, culture is conducted from 12 days to 20 days after the initiation of differentiation induction. The culture durations (the numbers of days) and the times to terminate the cultures described above are merely examples, and such conditions can be adequately modified.

The surface of a culture vessel used for adhesion culture may be coated with gelatin, laminin, collagen, poly-D-lysine, polyornithine, fibronectin, or vitronectin, so as to allow cells to adhere to the culture vessel and spread and grow thereon.

The basal medium described above can be used as the "neuronal maintenance medium." In this step, a basal medium is preferably D-MEM/F-12. The "neuronal maintenance medium" is a serum medium, and serum concentration is preferably about 1% to 10%, and more preferably about 5% to 10%, in the medium. Serum concentration may be increased gradually within the above-mentioned range, or it may be maintained at a constant level. In addition, neurotrophic factors that accelerate axon elongation can be added to the "neuronal maintenance medium." Examples of neurotrophic factors include BDNF, Neurotrophin-3, and Neurotrophin-4, with BDNF being preferable. The medium may further contain other growth factors, such as FGF, or additives, such as N2 Supplements. If retinoic acid is continuously added to the neuronal maintenance medium, axon elongation is inhibited after a given period of time has elapsed. Accordingly, it is preferable that the medium be retinoic acid-free.

If the level of the medium used in adhesion culture in Step (c) is above the height of the cell mass, adhesion of the cell mass to the culture vessel is likely to be inhibited. From the viewpoint of axon elongation to be achieved by firm adhesion of the cell mass to the culture vessel and prevention of damage imposed on the cell mass because of surface dryness, accordingly, the level of the medium is preferably the same as the height of the cell mass adhered to the culture vessel. Other culture conditions are in accordance with general cell culture conditions. For example, culture is carried out at about 30° C. to 40° C., and preferably at about 37° C., and at a $CO_2$ concentration of about 1% to 10%, and preferably about 5%.

In Step (c), retinal ganglion cells with elongated axons can be identified under the optical microscope or stereoscopic microscope. At the same time, expression of retinal ganglion cell markers, such as Brn3b, Math5, Sncg, Islet1, or Tuj1 may be inspected, and expression of Brn3b may be preferably inspected. Brn3b and Math5, which are the most inherent thereof to the retinal ganglion cells, are observed on the outermost layer of embryoid bodies. By separating this outermost layer, accordingly, retinal ganglion cells can be completely extracted.

2. Application in Regenerative Medicine

The retinal ganglion cells with elongated axons produced by the method of the present invention can be used as materials for regenerative medicine aimed at treatment of eye disease involving retinal ganglion cell damage in the form of, for example, a cell preparation or a cell sheet.

Examples of eye diseases involving retinal ganglion cell damage include glaucomatous diseases, hereditary optic neuropathy, optic nerve hypoplasia, ischemic disorders, and retinal diseases. Specific examples thereof include, but are not limited to, glaucoma (e.g., glaucomatous constriction of the visual field and glaucomatous atrophy of the optic nerve), autosomal dominant atrophy of the optic nerve, Leber's hereditary optic neuropathy (Leber's disease), idiopathic optic neuritis, optic nerve hypoplasia involved with iridosteresis, optic neuromyelitis (demyelination), multiple sclerosis (demyelination), ischemic optic neuropathy, central retinal artery occlusion, branch retinal artery occlusion, central retinal vein occlusion, branch retinal vein occlusion, traumatic or drug-induced optic neuropathy, diabetic optic neuropathy, retinopathy of prematurity, and retinal detachment.

It is sufficient if the cell preparation of the present invention contains a culture product of the retinal ganglion cells produced by the method described above. If necessary, the cell preparation can contain substances that accelerate or assist contact with the lesion. Examples of such substances include extracellular matrices, such as Matrigel™, collagen, fibronectin, vitronectin, laminin, cadherin, integrin, selectin, and cell-adhesive peptides typified by RGD peptides. The cell preparation of the present invention can be prepared in a dosage form, such as an injection preparation or injectable filler, and the resultant can be administered topically in the retina.

Also, the retinal ganglion cells produced by the method of the present invention can be superposed on top of each other, so as to produce a cell sheet. The retinal ganglion cells produced by the method of the present invention do not merely constitute an aggregate of retinal ganglion cells, but the retinal ganglion cells with elongated axons constitute layers of cells, and cell-to-cell interactions are retained. Thus, such retinal ganglion cells can be directly implanted into the lesion in the form of a culture product of retinal ganglion cells.

In Step (c), adhesion culture is carried out with the use of a culture vessel equipped with a coating layer that facilitates peeling and recovery of cells on a culture surface. This enables efficient production of a cell sheet. By seeding cells on the coating layer provided on the culture vessel and conducting culture, a cell sheet is formed on the surface of the coating layer. Thereafter, the culture surface is separated from the cell sheet in accordance with properties of the coating layer (e.g., temperature responsiveness and enzymatic degradability), and the cell sheet can be easily peeled and recovered from the culture vessel. As such coating layer, a self-degradable or self-disappearing material can be used. For example, a temperature-reactive polymer, such as poly-N-isopropylacrylamide (PIPAA), and collagen gel can be used.

3. Application in Screening of Protective Agent for Retinal Nerve or Regenerative Agent for Retinal Nerve The retinal ganglion cells produced by the method of the present invention can be used to screen for a protective agent for a retinal nerve, a regenerative agent for a retinal nerve, or the like. Screening can be carried out with the use of the retinal ganglion cells produced by the method described above (i.e., normal cell models), and screening can also be carried out with the use of retinal ganglion cells with the reproduced diseases or damages of the retinal nerve (i.e., optic neuropathy cell models). Optic neuropathy cell models can be produced in the manner described below. In the case of cell models of non-hereditary disease, for example, the normal cell models produced from iPS cells or ES cells are exposed to stresses (e.g., pressurization, low oxygen, elongation, or prophlogistic substances), the retinal nerve is damaged under such conditions, and optic neuropathy cell models can be thus produced. For example, retinal ganglion cells produced under pressurization can be used as glaucoma cell models, retinal ganglion cells produced under low-oxygen conditions can be used as ischemic optic neuropathy cell models, and retinal ganglion cells produced under elongation conditions can be used as trauma cell models. In the cases involving the use of cell models of hereditary diseases, iPS cells established from patients with hereditary optic neuropathy or normal iPS cells are genetically engineered, so as to produce iPS cells with the reproduced diseases (i.e., disease-specific iPS cells), and retinal ganglion cells are induced to differentiate therefrom by the method of the present invention. Examples of hereditary optic neuropathies include optic nerve hypoplasia involved with congenital iridosteresis caused by a mutation of the Pax6 gene (a nonsense mutation of Pax6), autosomal dominant atrophy of the optic nerve caused by a mutation of the OPA1 gene (high-frequency mutation of c.2708delTTAG), and Leber's hereditary optic neuropathy (Leber's disease) caused by a mutation of the mitochondrial gene (high-frequency mutation of G117788A). Test substances are brought into contact with these cell models, and the effects of the test substances for protection or regeneration of retinal ganglion cells can be evaluated. Whether or not the test substances are capable of protecting or regenerating retinal ganglion cells can be evaluated by, for example, bringing the test substances into contact with the retinal ganglion cells, and, after a given period of time, analyzing cell viability, promotion or suppression of axon elongation, changes in the axonal flow and electrophysiological reactions (action potentials and action currents), and expression of molecular markers (e.g., apoptosis-associated genes). Test substances can be brought into contact with retinal ganglion cells by any method known to a person skilled in the art, without particular limitation. For example, test substances may be added to a medium containing retinal ganglion cells, and the retinal ganglion cells may then be cultured in the presence of the test substances for a given period of time. Such contact can be carried out under stress conditions (e.g., pressurization, low-oxygen, or prophlogistic substances). In the same manner as in the screening method described above, inhibition of axonal growth of retinal ganglion cells caused by chemical substances or the like can be evaluated.

Test substances to be subjected to the screening method of the present invention are not particularly limited. Examples of test substances include: mixtures containing a plurality of compounds, such as animal and/or plant tissue extracts or microbial culture products and samples purified therefrom; naturally occurring molecules, such as amino acids, peptides, oligopeptides, polypeptides, proteins, nucleic acids, lipids, steroids, glycoproteins, and proteoglycans; synthetic analogs or derivatives of naturally occurring molecules, such as peptide mimics; non-naturally occurring molecules, such as low-molecular-weight organic compounds prepared via combinatorial chemistry; and mixtures of any thereof. A single type of test substance may be independently tested, or a mixture of several candidate test substances (including libraries) may be tested. Examples of libraries including a plurality of test substances include synthetic compound libraries and peptide libraries.

4. Application in Analysis of Intractable Optic Neuropathy

Hereditary optic neuropathies, such as autosomal dominant atrophy of the optic nerve, Leber's disease, and optic nerve hypoplasia involved with iridosteresis, are intractable optic neuropathies, and pathogenic mechanisms thereof and disease-associated molecules thereof are unknown. The process of inducing iPS cells with the reproduced diseases produced by genetic engineering of iPS cells established from patients with hereditary optic neuropathy or normal iPS cells (i.e., disease-specific iPS cells) to differentiate into retinal ganglion cells by the method of the present invention is compared with the process of inducing iPS cells established from healthy persons to differentiate into retinal ganglion cells by the method of the present invention. Thus, pathogenic mechanisms of the diseases and disease-associated molecules can be analyzed, and causes and clinical conditions of the diseases can be revealed.

EXAMPLES

Hereafter, the present invention is described in greater detail with reference to the examples, although the technical scope of the present invention is not limited to these examples.

(Example 1) Preparation of Retinal Ganglion Cells from Human iPS Cells

1. Method
(1) Induction of Differentiation from Human iPS Cells into Retinal Progenitor Cells Human skin-derived iPS cells 409B2 provided by the Riken BioResource Center (RIKEN BRC) were used as human iPS cells (Okita et al., 2011, A more efficient method to generate integration-free human iPS cells, Nat. Methods). Basically, human iPS cells were induced to differentiate into retinal progenitor cells in the manner described below in accordance with the serum-free floating culture of embryoid body-like aggregates with the quick reaggregation (SFEBq) method described in the literature (Nakano, T. et al., Self-formation of optic cups and storable stratified neural retina from human ESCs, Cell Stem Cell 10, 771-785, 2012), except that Matrigel concentration and FBS concentration were changed.

MEF feeder cells treated with mitomycin (MMC) were seeded in a petri dish, the human iPS cells described above were seeded on the MEF feeder cells, and culture was conducted in a iPS cell culture medium (ReproCELL) supplemented with 10 ng/ml recombinant human bFGF (Invitrogen Corporation) for 4 days. The iPS cells were peeled and recovered via trypsin treatment, the cells were transferred to a 10-cm gelatin-coated petri dish, and the cells were then allowed to stand for 30 minutes therein. After the cells were recovered, 10,000 cells were suspended relative to 100 µl of the retinal differentiation medium RDM (i.e., G-MEM supplemented with 20% KSR, 0.1 mM 2-mercaptoethanol, 0.1 mM non-essential amino acid additive, 1 mM sodium pyruvate, 20 µM Y-27632 (ROCK inhibitor), 3 µM IWR-1e (Wnt signal inhibitor), 100 U/ml penicillin, and 100 µg/ml streptomycin), the cells were seeded in a non-adherent 96-well plate at 9,000 cells/well, and floating culture was initiated at 37° C. in the presence of 5% $CO_2$ (hereafter, the culture duration (the number of days) is counted relative to Day 0 when the floating culture was initiated). Matrigel (BD Bioscience) was added to adjust the final concentration to 0.5% 2 days after the initiation of differentiation induction (Day 2), Y-27632 and IWR-1e were excluded from the composition of the retinal differentiation medium described above on Day 12, and the medium was exchanged with a serum medium supplemented with FBS (final concentration: 1%). The Wnt signal activator CHIR99021 (final concentration: 3 µM) and the Shh signal activator SAG (final concentration: 100 nM) were added to the medium on Day 15, and culture was conducted for an additional 3 days.

(2) Maturation of Retinal Progenitor Cells (Induction of Differentiation from Retinal Progenitor Cells into Retinal Ganglion Cells)

The medium was exchanged with a serum-free retinal maturation medium RMM (GlutaMAX-containing D-MEM/F12, N2 Supplements (Life Technologies)) on Day 18, and floating culture was continued up to Day 24 in the same medium. The medium was exchanged with a retinal maturation medium supplemented with FBS (final concentration: 1%) and retinoic acid (0.5 µM) (GlutaMAX-containing D-MEM/F12, N2 Supplements (Life Technologies)) on Day 24, and floating culture was then continued for an additional 3 days. This floating culture was conducted at atmospheric oxygen concentration.

(3) Axon Elongation

Floating culture was terminated on Day 27, embryoid bodies were transferred to a 24-well plate coated with poly-D-lysine and laminin in such a state that optic vesicles (OVs) remained attached to the main bodies of the embryoid bodies, and adhesion culture was then initiated. Adhesion culture was conducted in a neuronal maintenance medium supplemented with BDNF (final concentration: 100 ng/ml) (GlutaMAX-containing D-MEM/F12, N2 Supplements (Life Technologies), 1% FBS), FBS concentration in the medium was increased successively (5% on Day 30 and 10% on Day 35), and culture was continued up to Day 40 (i.e., 13 days after the initiation of adhesion culture). At the time of adhesion culture, the medium level was maintained to be approximately the same as the height of cells (about 250 µl).

FIG. 1 schematically shows a method for preparation of retinal ganglion cells from human iPS cells comprising the steps (1) to (3) described above.

(4) Immunostaining

After the cells were immobilized with PFA on Day 24 and on Day 40, the cells were blocked with 3% BSA at room temperature for 60 minutes. Thereafter, the cells were allowed to react with the primary antibodies overnight (with anti-Rx antibodies (Thermo Scientific) on Day 24 and with anti-Brn3b antibodies (Santa Cruz Biotechnology, Inc.) on Day 40), washed with TBS, and then allowed to react with the secondary antibodies (Alexa Fluor-555).

(5) Time Course of Marker Gene (Brn3b, Rx, and Pax6) Expression

The time course of marker gene (Brn3b, Rx, and Pax6) expression in the process of differentiation induction was inspected. Specifically, cells were recovered with the elapse of time starting from the time when differentiation induction was initiated (i.e., 6, 12, 18, 24, 30, and 40 days thereafter), the recovered cells were washed twice with PBS(−), and RNAs were extracted from the cells with the use of the RNeasy Mini Kit (Qiagen). After RNAs were reversely transcribed into cDNAs with the use of the 2-step real-time PCR kit (Takara Bio Inc.), real-time PCR was carried out with the use of the StepOnePlus Real-Time PCR Systems (Life Technologies) and the sets of primers described below (40 cycles of 95° C. for 15 seconds and 60° C. for 30 seconds), and expression levels of the Brn3b gene, the Rx gene, and the Pax6 gene were assayed.

Primer Set for Human Brn3b Gene Amplification

```
Forward primer:
                                  (SEQ ID NO: 1)
5'-TGACACATGAGCGCTCTCACTTAC-3'

Reverse primer:
                                  (SEQ ID NO: 2)
5'-ACCAAGTGGCAAATGCACCTA-3'
```

Primer Set for Human Rx Gene Amplification

```
Forward primer:
                                  (SEQ ID NO: 3)
5'-CCGTCCCTAAGCGTGCTTTC-3'

Reverse primer:
                                  (SEQ ID NO: 4)
5'-ACTGGGAGCTTCACTAATTTGCTCA-3'
```

Primer Set for Human Pax6 Gene Amplification

```
Forward primer:
                                  (SEQ ID NO: 5)
5'-TTTAAAGATCCTGGAGGTGGACATA-3'
```

```
               -continued
  Reverse primer:
                                       (SEQ ID NO: 6)
    5'-GCTCAGGTGCTCGGGTTCTA-3'
```

The mRNA expression levels were normalized to the HPRT gene expression levels and expressed relative to the expression level on the day when the differentiation induction was initiated, which was set to 1.

2. Results

Figure 2:
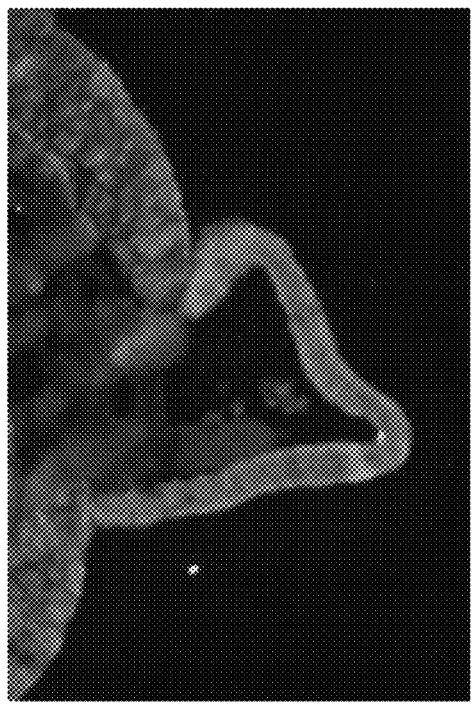
FIG. 2 shows an immunostaining image of embryoid bodies induced to differentiate from human iPS (hiPS) cells using the anti-Rx antibody (24 days after the initiation of differentiation induction).

FIG. 2 shows an immunostaining image of embryoid bodies 24 days after the initiation of differentiation induction obtained with the use of an anti-Rx antibody. The presence of the optic vesicle as a retinal progenitor was confirmed 24 days after the initiation of differentiation induction.

Figure 3:
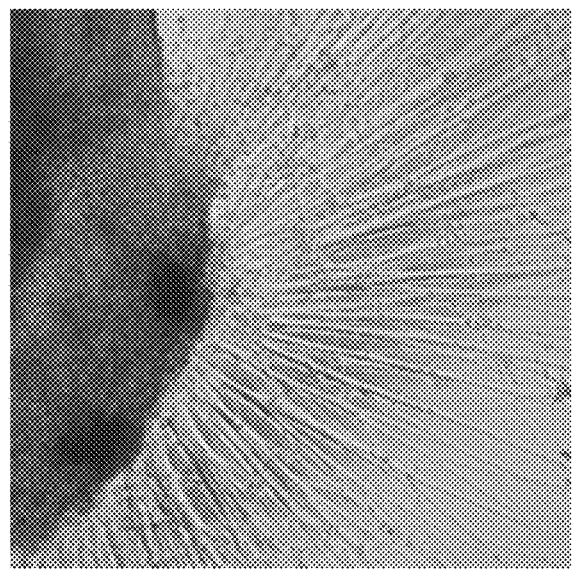
FIG. 3 shows a stereomicroscopic photograph of embryoid bodies induced to differentiate from human iPS (hiPS) cells (100×) (40 days after the initiation of differentiation induction and 13 days after the initiation of adhesion culture).

FIG. 3 shows a stereomicroscopic image of embryoid bodies 40 days after the initiation of differentiation induction (13 days after the initiation of adhesion culture). Axon elongation was already confirmed on the day following the initiation of adhesion culture, and elongated axons approximately 1 cm in length radially from the margins of the embryoid bodies that had adhered to the plate were confirmed 40 days after the initiation of differentiation induction (13 days after the initiation of adhesion culture). The percentage of embryoid bodies induced to differentiate into retinal ganglion cells with elongated axons was found to be 80% to 90% on the basis of the number of embryoid bodies in which axon elongation was observed relative to the number of the embryoid bodies adhered to the plate.

Figure 4:
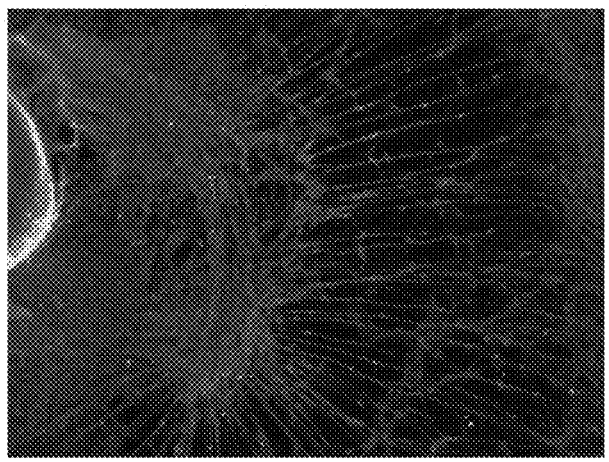
FIG. 4 shows an immunostaining image of embryoid bodies induced to differentiate from human iPS (hiPS) cells using the anti-Brn3b antibody (40 days after the initiation of differentiation induction and 13 days after the initiation of adhesion culture).

FIG. 4 shows an immunostaining image of embryoid bodies 40 days after the initiation of differentiation induction (13 days after the initiation of adhesion culture) obtained using the anti-Brn3b antibody. The presence of retinal ganglion cells (Brn3b-positive cells) was confirmed 40 days after the initiation of differentiation induction.

Figure 5:
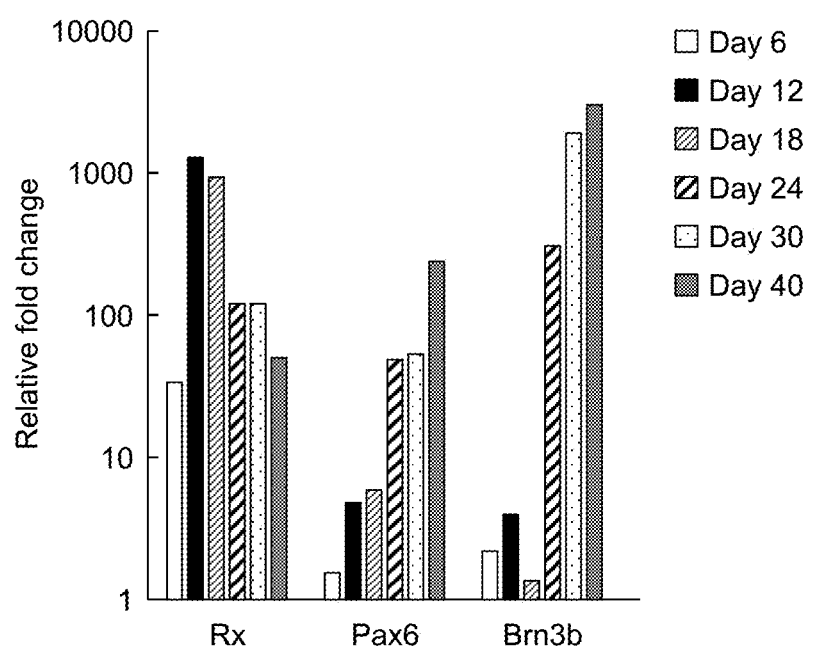
FIG. 5 shows the time course of expression of retinal differentiation-associated marker genes (Brn3b, Rx, and Pax6) in the embryoid bodies induced to differentiate from human iPS cells.

FIG. 5 shows the time course of expression levels of marker genes (Brn3b, Rx, and Pax6). Expression of the Rx and Pax6 genes as retinal progenitor cell marker genes was observed at an early stage after the initiation of differentiation induction, the expression level of the Brn3b gene as the retinal ganglion cell marker gene began to rapidly increase 18 days after the initiation of differentiation induction, and the expression level reached its maximal level 40 days after the initiation of differentiation induction (13 days after the initiation of adhesion culture).

(Example 2) Preparation of Retinal Ganglion Cells from Mouse ES Cells

1. Method (1) Induction of Differentiation from Mouse ES Cells into Retinal Progenitor Cells GFP-expressing LB10 Mouse Embryonic Stem Cells (GSC-5003, Cosmo Bio Co., Ltd.) were used as mouse ES cells. Mouse ES cells were induced to differentiate into retinal progenitor cells in the manner described below in accordance with the literature (Eiraku M., Sasai Y., Mouse embryonic stem cell culture for generation of three-dimensional retinal and cortical tissues, Nat. Protoc., 2011, 7 (1): 69-79).

MEF feeder cells treated with mitomycin (MMC) were seeded in a petri dish, the mouse ES cells described above were seeded on the MEF feeder cells, and culture was conducted in a mouse ES cell culture medium (Knockout DMEM supplemented with 15% KSR, 0.05 mM 2-mercaptoethanol, 0.1 mM nonessential amino acid additive, 0.01 v/v % GlutaMax, and 0.001 v/v % LIF, Wako). The culture medium was exchanged every day, and cells were transferred every 3 days. The mouse ES cells were peeled via trypsin treatment and recovered 3 days after the final transfer, the recovered cells were transferred to a 10-cm gelatin-coated petri dish, and the cells were then allowed to stand for 30 minutes therein. After the cells were recovered, the cells were suspended in a retinal differentiation medium (G-MEM supplemented with 1.5% KSR, 0.1 mM 2-mercaptoethanol, 0.1 mM nonessential amino acid additive, and 1 mM sodium pyruvate) at 5,000 cells relative to 100 µl of the medium, the cells were seeded in a non-adherent 96-well plate at 4,500 cells/well, and floating culture was initiated at 37° C. in the presence of 5% $CO_2$ (hereafter, the duration of culture (the number of days) is counted relative to Day 0 after the initiation of differentiation induction when the floating culture was initiated). Matrigel was added thereto to the final concentration of 2.0% on Day 1, and floating culture was continued up to Day 7 in the same medium.

(2) Maturation of Retinal Progenitor Cells (Induction of Differentiation from Retinal Progenitor Cells into Retinal Ganglion Cells)

The medium was exchanged with a serum-free retinal maturation medium (GlutaMAX-containing D-MEM/F12, N2 Supplements (Life Technologies)) on Day 7, and floating culture was continued in the same medium up to Day 10. The medium was exchanged with a retinal maturation medium (GlutaMAX-containing D-MEM/F12, N2 Supplements (Life Technologies)) supplemented with FBS (final concentration: 1%) and retinoic acid (0.5 µM) on Day 10, and floating culture was then continued for 3 days.

(3) Axon Elongation

Floating culture was terminated on Day 13, embryoid bodies were transferred to a 24-well plate coated with poly-D-lysine and laminin, and adhesion culture was then initiated. Adhesion culture was conducted in a neuronal maintenance medium (GlutaMAX-containing D-MEM/F12, N2 Supplements (Life Technologies), 5% FBS, 100 ng/ml BDNF) up to Day 20 (7 days after the initiation of adhesion culture). At the time of adhesion culture, the medium level was maintained to be approximately the same as the height of cells.

(4) Immunostaining

After the cells were immobilized with PFA on Day 18, the cells were blocked with 3% BSA at room temperature for 60 minutes. Thereafter, the cells were allowed to react with primary antibodies (anti-Brn3b antibodies, Santa Cruz Biotechnology, Inc.) overnight, washed with TBS, and then allowed to react with secondary antibodies (Alexa Fluor-555).

(5) Time Course Expression Levels of Marker Genes (Brn3b, Rx, and Pax6)

The time course of expression levels of marker genes (Brn3b, Rx, and Pax6) in the process of differentiation induction was inspected. Specifically, cells were recovered with the elapse of time after the initiation of differentiation induction (7, 10, 14, and 20 days after the initiation of differentiation induction), the recovered cells were washed twice with PBS (−), and RNAs were extracted from the cells with the use of the RNeasy Mini Kit (Qiagen). After RNAs were reversely transcribed into cDNAs with the use of the 2-step real-time PCR kit (Takara Bio Inc.), real-time PCR was carried out with the use of the StepOnePlus real-time PCR system (Life Technologies) with the use of the sets of primers described below (40 cycles of 95° C. for 15 seconds and 60° C. for 30 seconds), and the expression levels of the Brn3b gene, the Rx gene, and the Pax6 gene were assayed.

Primer Set for Mouse Brn3b Gene Amplification

```
Forward primer:
                                      (SEQ ID NO: 7)
5'-ATCGTCTCCCAGAGTAAGAGC-3'

Reverse primer:
                                      (SEQ ID NO: 8)
5'-CACGGGATGGTGTTCATGG-3'
```

Primer Set for Mouse Rx Gene Amplification

```
Forward primer:
                                      (SEQ ID NO: 9)
5'-CGACGTTCACCACTTACCAA-3'

Reverse primer:
                                      (SEQ ID NO: 10)
5'-TCGGTTCTGGAACCATACCT-3
```

Primer Set for Mouse Pax6 Gene Amplification

```
Forward primer:
                                      (SEQ ID NO: 11)
5'-TACCAGTGTCTACCAGCCAAT-3'

Reverse primer:
                                      (SEQ ID NO: 12)
5'-TGCACGAGTATGAGGAGGTCT-3'
```

The mRNA expression level was normalized to the HPRT gene expression level and expressed relative to the expression level on the day when differentiation induction was initiated, which was set to 1.

2. Results

Figure 6:
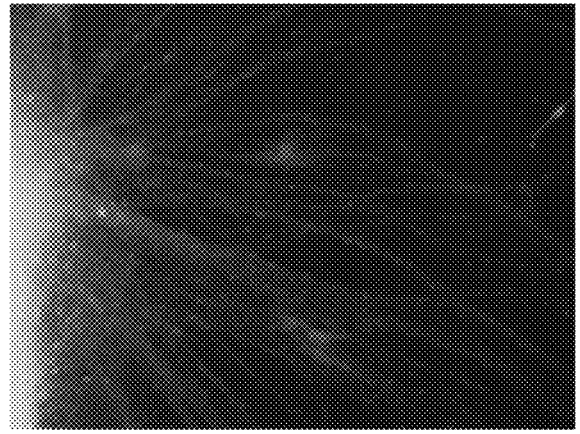
FIG. 6 shows a stereomicroscopic photograph of embryoid bodies induced to differentiate from mouse ES (mES) cells (100×) (18 days after the initiation of differentiation induction and 5 days after the initiation of adhesion culture).

FIG. 6 shows a stereomicroscopic image of embryoid bodies 18 days after the initiation of differentiation induction (5 days after the initiation of adhesion culture). As with the case of human iPS cells, axons that had radially developed approximately 1 cm from the margin of the embryoid bodies adhered to the plate were observed.

Figure 7:
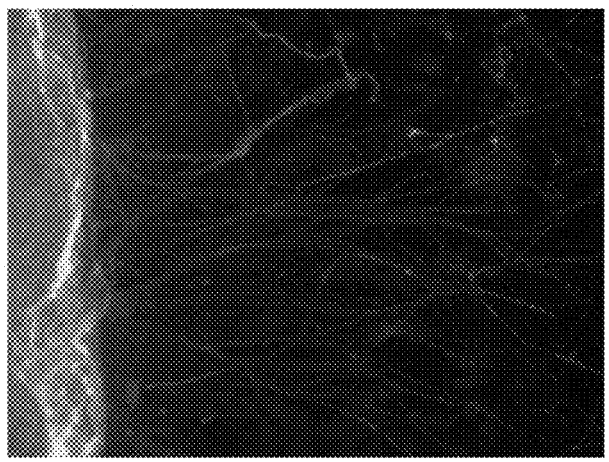
FIG. 7 shows an immunostaining image of embryoid bodies induced to differentiate from mouse ES (mES) cells using the anti-Brn3b antibody (18 days after the initiation of differentiation induction and 5 days after the initiation of adhesion culture).

FIG. 7 shows an immunostaining image of embryoid bodies 18 days after the initiation of differentiation induction (5 days after the initiation of adhesion culture) using the anti-Brn3b antibody. As with the case of human iPS cells, the presence of retinal ganglion cells (Brn3b-positive cells) was confirmed.

Figure 8:
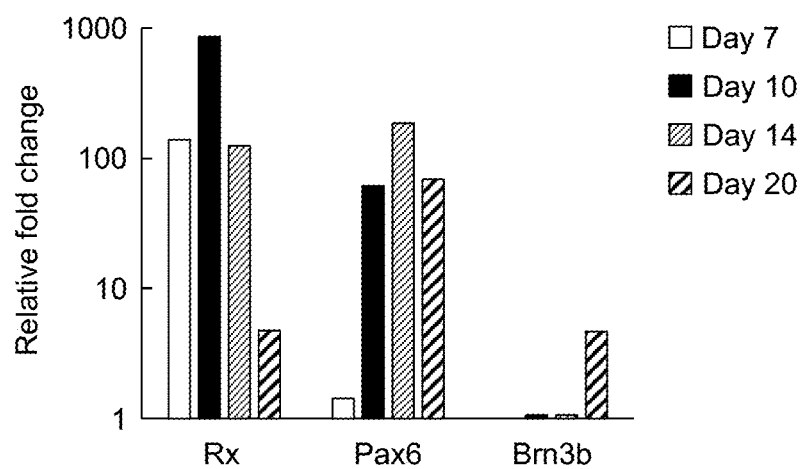
FIG. 8 shows the time course of expression of retinal differentiation-associated marker genes (Brn3b, Rx, and Pax6) in the embryoid bodies induced to differentiate from mouse ES cells.

FIG. 8 shows the time course of expression of marker genes (Brn3b, Rx, and Pax6). Expression of the Rx and Pax6 genes as the retinal progenitor cell marker genes was observed at an early stage after the initiation of differentiation induction, and the expression level of the Brn3b gene as the retinal ganglion cell marker gene began to increase 20 days after the initiation of differentiation induction.

Figure 9:
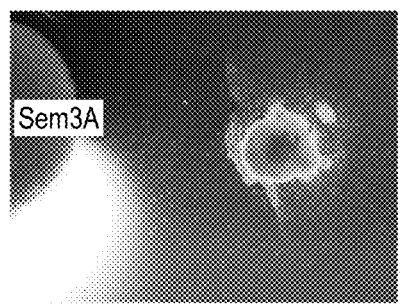
FIG. 9 shows the results of a controlled-release test of neural inhibitors (Sema3A) on retinal ganglion cells produced from human iPS cells by the method of the present invention.

(Example 3) Controlled-Release Test of Neural Inhibitor on Retinal Ganglion Cells Floating culture was terminated 27 days after the initiation of differentiation induction that was conducted in Example 1, embryoid bodies were transferred and allowed to adhere to a 6-well plate coated with poly-D-lysine and laminin, and adhesion culture was then initiated using a neuronal maintenance medium supplemented with BDNF (final concentration: 100 ng/ml) (GlutaMAX-containing D-MEM/F12, N2 Supplements (Life Technologies), 1% FBS). The nerve growth inhibitor (Semaphorin 3A (SemaA)) was subjected to a controlled-release test 2 days after the initiation of adhesion culture. At the outset, MedGEL SP P15 (MedGEL Corporation) was soaked in 30 μl of 100 μg/μl Sema3A, and it was allowed to stand at 4° C. for 60 minutes. MedGEL was placed on Kimwipes, an excess solution was removed therefrom, and MedGEL was placed in a region approximately 5 mm away from the embryoid bodies. Thereafter, 10 μl of 100 μg/μl Sema3A was added on top of MedGEL every 3 days. It was observed under the stereoscopic microscope 9 days after the initiation of the controlled-release test. The results are shown in FIG. 9. It was confirmed that axon elongation would be significantly inhibited on the Semaphorin 3A (SemaA) side. Therefore, the retinal ganglion cells prepared by the method of the present invention can be used for dynamic analysis of retinal ganglion cells against neural inhibitors using changes in axons thereof as the indicators.

Primers used for gene expression analysis via real-time RT-PCR and antibodies used for immunostaining test in Examples 4 to 8 and 13 below are summarized in Table 1 and Table 2 below.

TABLE 1

| Gene | Accession No | Forward | Reverse |
| --- | --- | --- | --- |
| Hprt1 | NM_000194.2 | GGCAGTATAATCCAAAGATGGTCAA (SEQ ID NO: 13) | GTCAAGGGCATATCCTACAACAAAC (SEQ ID NO: 14) |
| Rx | NM_013435.2 | CCGTCCCTAAGCGTGCTTTC (SEQ ID NO: 15) | ACTGGGAGCTTCACTAATTTGCTCA (SEQ ID NO: 16) |
| Pax6 | NM_000280.4 | TTTAAAGATCCTGGAGGTGGACATA (SEQ ID NO: 17) | GCTCAGGTGCTCGGGTTCTA (SEQ ID NO: 18) |
| Chx10 | NM_182894.2 | AACCCAATCTGGCTGGTAAATGA (SEQ ID NO: 19) | CAGCAGGCCCTTAATGCGTA (SEQ ID NO: 20) |
| Six3 | NM_005413.3 | GCAGAAGACGCATTGCTTCAA (SEQ ID NO: 21) | GTTCGCGTTTCTTGCTGGG (SEQ ID NO: 22) |
| Brn3b | NM_004575.2 | TGACACATGAGCGCTCTCACTTAC (SEQ ID NO: 23) | ACCAAGTGGCAAATGCACCTA (SEQ ID NO: 24) |
| Crx | NM_000554.4 | ACCCTGATCTCTAGAGCCCACAA (SEQ ID NO: 25) | CTTAATGTCCCAGAACCCAGCA (SEQ ID NO: 26) |
| Syntaxin | NM_004603.3 | TAAAGAGCATCGAGCAGTCCA (SEQ ID NO: 27) | GACATGACCTCCACAAACTTTCT (SEQ ID NO: 28) |

TABLE 1-continued

| Gene | Accession No | Forward | Reverse |
|---|---|---|---|
| Calbindin | NM_004929.2 | TCCAGGGAATCAAAATGTGTGG (SEQ ID NO: 29) | GCACAGATCCTTCAGTAAAGCA (SEQ ID NO: 30) |
| PKC α | NM_002737.2 | ACAACCTTCCAACAACCTTGAC (SEQ ID NO: 31) | CCTTCCTGTCGGCAAGCAT (SEQ ID NO: 32) |
| Math5 | NM_145178.3 | CCCTAAATTTGGGCAAGTGAAGA (SEQ ID NO: 33) | CAAAGCAACTCACGTGCAATC (SEQ ID NO: 34) |
| Mitf | NM_198159.2 | AGAGTCTGAAGCAAGAGCACTG (SEQ ID NO: 35) | TGCGGTCATTTATGTTAAATCTTC (SEQ ID NO: 36) |
| Tuj1 | NM_006086.3 | GGCCAAGGGTCACTACACG (SEQ ID NO: 37) | GCAGTCGCAGTTTTCACACTC (SEQ ID NO: 38) |
| Islet1 | NM_002202.2 | GCGGAGTGTAATCAGTATTTGGA (SEQ ID NO: 39) | GCATTTGATCCCGTACAACCT (SEQ ID NO: 40) |
| Sncg | NM_003087.2 | TGAGCAGCGTCAACACTGTG (SEQ ID NO: 41) | GAGGTGACCGCGATCTTCTC (SEQ ID NO: 42) |
| Tau | NM_001123066.3 | CCAAGTGTGGCTACATTAGGCA (SEQ ID NO: 43) | CCAATCTTCGACTGGACTCTGT (SEQ ID NO: 44) |
| NFL | NM_006158.4 | TCAACGTGAAGATGGCTTTGGATA (SEQ ID NO: 45) | AAGACCTGGGAGCTCTGGGAGTA (SEQ ID NO: 46) |
| NFM | NM_005382.2 | ACAACCACGACCTCAGCAGCTA (SEQ ID NO: 47) | ATGACGAGCCATTTCCCACTTT (SEQ ID NO: 48) |
| NFH | NM_021076.3 | CAGCTGCGAGAATACCAGGAC (SEQ ID NO: 49) | CACCTTTATGTGAGTGGACACAGAC (SEQ ID NO: 50) |

TABLE 2

| Gene product | Supplier | Product No. | Dilution ratio |
|---|---|---|---|
| RX | Thermo Fisher Scientific | PA5-11477 | 1:25 |
| PAX6 | Covance | PRB-278P | 1:50 |
| BRN3B | Santa Cruz | sc-31989 | 1:25 |
| CRX | Abnova | H00001406-M02 | 1:50 |
| MATH5 | Millipore | AB5694 | 1:50 |
| ISLET1 | Abcam | ab20670 | 1:50 |
| SNCG | GeneTex | GTX110483 | 1:50 |
| TUJ1 | Sigma | T-5076 | 1:200 |
| TAU | Santa Cruz | sc-5587 | 1:100 |
| NFL | Cell Signaling Technology | #8024S | 1:500 |
| NFH | Abcam | ab8135 | 1:100 |

(Example 4) Expression Analysis of Transcription Factor Associated with Retinogenesis 1. Method
(1) Real-Time RT-PCR Total RNA was extracted from cells using an RNeasy Mini Kit (Qiagen). The mRNA expression level in each RNA sample was determined using the StepONE Sequence Detection System (Applied Biosystems). The reverse transcription polymerase chain reaction (RT-PCR) was performed using a One Step SYBR™ PrimeScript™ PLUS RT-PCR Kit (Takara Bio Inc.). Real-time PCR was carried out using the primers shown above (Table 1), and expression levels of the genes (Rx, Pax6, Chx10, Six3, Brn3b, Crx, Syntaxin, Calbindin, PKCα, Math5, and Mitf) as transcription factors associated with retinogenesis were assayed with the elapse of time. PCR conditions were as follows: an initial hold at 42° C. for 5 minutes; incubation at 95° C. for 10 seconds; and then 40 cycles of 95° C. for 5 seconds and 60° C. for 31 seconds. The mRNA expression level was assessed by evaluating the threshold cycle ($C_T$) value. The $C_T$ value was normalized to the HPRT1 expression level and expressed relative to the mRNA expression level on the day (Day 0) when the differentiation induction was initiated (when floating culture was initiated), which was set to 1.

(2) Immunostaining

Immunostaining of Rx, Pax6, Brn3b, Math5, and Crx of the optic vesicles (OVs) on the floating embryoid bodies (EB) 24 days after the induction of differentiation from human iPS cells, and those of an extruded clump of cells 34 days after the initiation of differentiation induction (cells induced to differentiate from optic vesicles on embryoid bodies (EB)) transferred to adhesion culture) was performed in the manner described below. Specimens (frozen cell sections or whole cells) were fixed with 4% paraformaldehyde (pH 7.0) at room temperature for 20 minutes. After the specimens were washed two times with PBS, the specimens were incubated in the presence of 0.1% Triton X-100 at room temperature for 15 minutes, and the specimens were then washed three times with PBS (each washing was conducted for 5 minutes). Subsequently, the specimens were incubated in the presence of 3% BSA at room temperature for 30 minutes and then allowed to react with primary antibodies (Table 2) at 4° C. for 16 hours. Secondary antibody reactions were carried out by incubation with the corresponding species-specific Alexa Fluor-488-conjugated antibodies (1:500, Invitrogen Corporation) at room temperature for 1 hour in the dark. After the specimens were washed four times with PBS (each washing was conducted for 5 minutes), the specimens were stained with ProLong Gold Antifade Reagent with DAPI (Invitrogen Corporation), followed by observation under an IX71 inverted research microscope (Olympus Corporation) or BZ-9000E (Keyence Corporation).

2. Results

Figure 10:
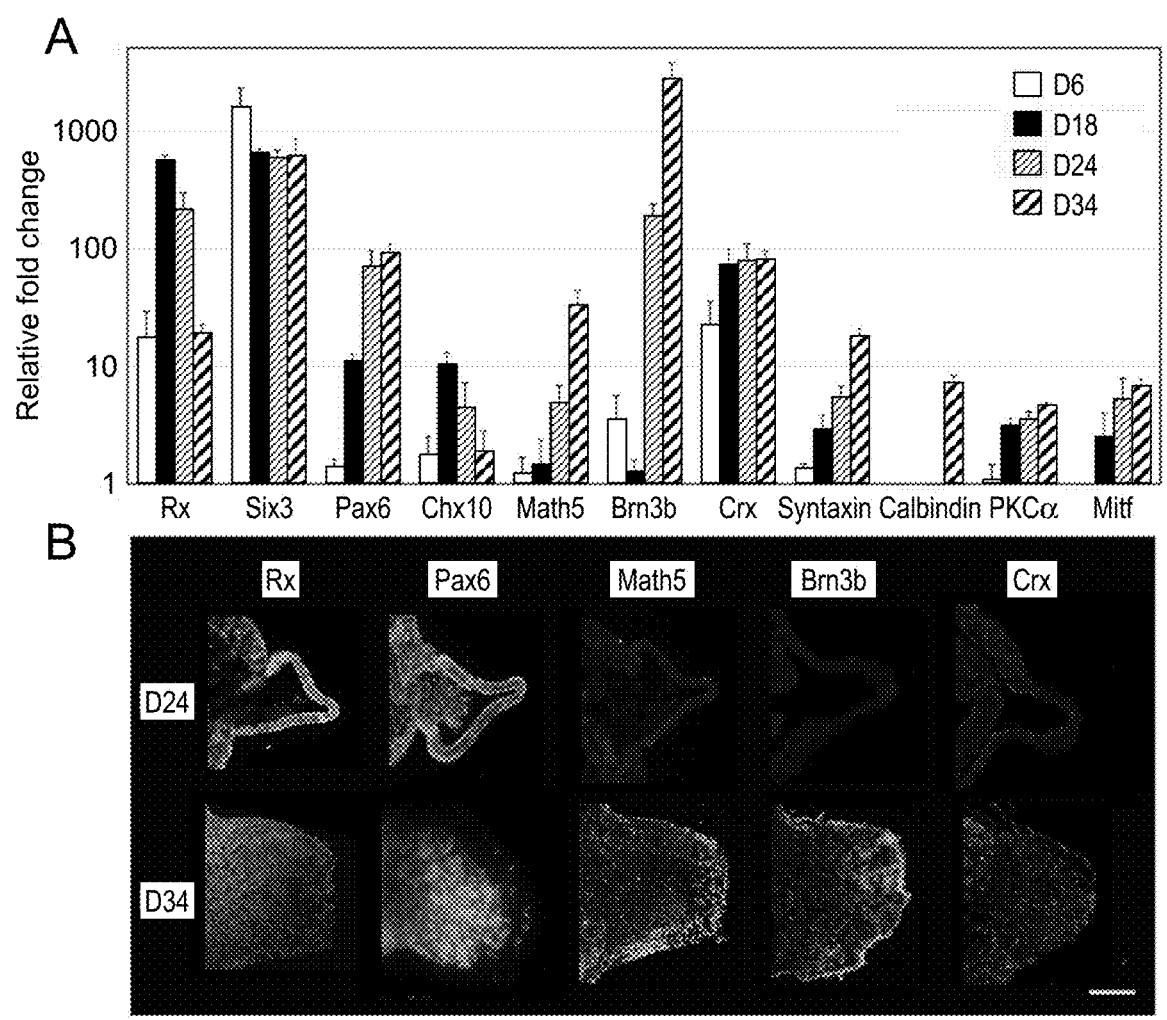
FIG. 10A shows the results of expression analysis of retinogenesis-associated transcription factors (i.e., Rx, Six3, Pax6, Chx10, Math5, Brn3b, Crx, Syntaxin, Calbindin, PKCα, and Mitt) 6 days (D6), 18 days (D18), 24 days (D24), and 34 days (D34) after the initiation of differentiation induction from human iPS cells via RT-PCR (error bar: the mean of three independent tests±SD; vertical axis: semi-logarithmic scale). The mRNA expression level is normalized to the HPRT1 expression level, and it is expressed relative to the mRNA expression level measured 0 days after the initiation of differentiation induction, which is designated 1.
FIG. 10B shows an immunostaining image of Rx, Pax6, Math5, Brn3b, and Crx in optic vesicles (OV) on embryoid bodies (EB) 24 days (D24) and 34 days (D34) days after the initiation of differentiation induction from human iPS cells in optic vesicles (OV) (scale bar: 100 µm).

The results of expression analysis of the transcription factors are shown in FIG. 10. The retinal homeobox gene, Rx, and the paired box gene 6, Pax6, are known to belong to the group of eye-field transcription factors and to be crucial in early retinogenesis. Upregulation of Rx apparently began 6 days after the initiation of differentiation induction (Day 6) when embryoid bodies (EB) had maturely formed, and the expression level reached its peak 18 days after the initiation of differentiation induction (Day 18) when the OVs began to develop. Thereafter, upregulation of the Pax6 gene, which was the downstream gene of Rx, continued (FIG. 10A).

Math5 is known to be expressed in post-mitotic retinal progenitor cells under direct control by Pax6 and to regulate the formation of retinal ganglion cells (RGCs). Math5 mutation leads to lack of retinal ganglion cells in mice, and it leads to optic nerve aplasia in humans. Brn3b, which is known as the most reliable RGC marker, is a member of the POU-domain family of transcription factors, and its expression is controlled by Math5. Brn3b is considered to determine the RGC fate by acting as a repressor of differentiation into non-RGC cell types. In the differentiation process thereof, Islet1, an LIM-homeodomain factor, acts as a coregulator. According to this analysis, the Brn3b expression level was relatively low until 18 days after the initiation of differentiation induction (Day 18), and such expression level dramatically increased up to 24 days after the initiation of differentiation induction when the optic vesicles (OVs) were well developed from the floating embryoid bodies (Ebs), following an increase in the Math5 expression level (FIG. 10A).

It is known that Chx10 is associated with the proliferation of retinal progenitor cells and that it is initially expressed in all retinal progenitor cells, although expression thereof would then be restricted to retinal bipolar cells. This analysis revealed that Chx10 expression became apparent 18 days after the initiation of differentiation induction (Day 18) and it continued up to at least 34 days after the initiation of differentiation induction (Day 34) when retinal ganglion cells and axons would begin to develop. While Crx expression is known to be restricted in premature and mature cells of a photoreceptor lineage, Crx expression was also first observed 18 days after the initiation of differentiation induction (Day 18), following Chx10 expression (FIG. 10A).

Amacrine cells start to differentiate immediately after RGC differentiation. In this analysis, Syntaxin, which is known as an amacrine cell marker, showed delayed expression, following Brn3b expression. Expression of Calbindin, which is a horizontal cell marker developing at later stages of retinogenesis, and that of PKCα, which is a bipolar cell marker, were not substantially observed up to 34 days after the initiation of differentiation induction (Day 34). The time course of the gene expression was quite consistent with that in human retinogenesis.

In this analysis, expression of Mitf, which is a microphthalmia-associated transcription factor and the master regulator of melanocyte and retinal pigment epithelium (RPE) development, was not substantially observed. This indicates that human iPS cells are induced to differentiate into the neural retinal lineage but they are not induced to differentiate into the retinal pigment epithelial (RPE) cell lineage by the method of the present invention.

As a result of immunostaining, expression of Rx and Pax6 was observed in both optic vesicles (OVs) and the clump. Expression of Brn3b and Math5, which are the most typical RGC markers, was observed only in the clump and localized within the margins of the clump. In contrast, low expression of Crx was observed within the clump (FIG. 10B).

(Example 5) Structural Analysis of Retinal Ganglion Cells Induced to Differentiate from Human iPS Cells (1) Optical Microscopy
(Method)

Specimens were fixed with 4% paraformaldehyde in 100 mM phosphate buffer at 4° C. for 3 hours, rinsed in water, dehydrated through a graded series of alcohol to xylene, and embedded in paraffin. Each block was serially sectioned at a 3-μm thickness. Deparaffinized sections were then stained with haematoxylin and eosin.
(Results)

Figure 11:
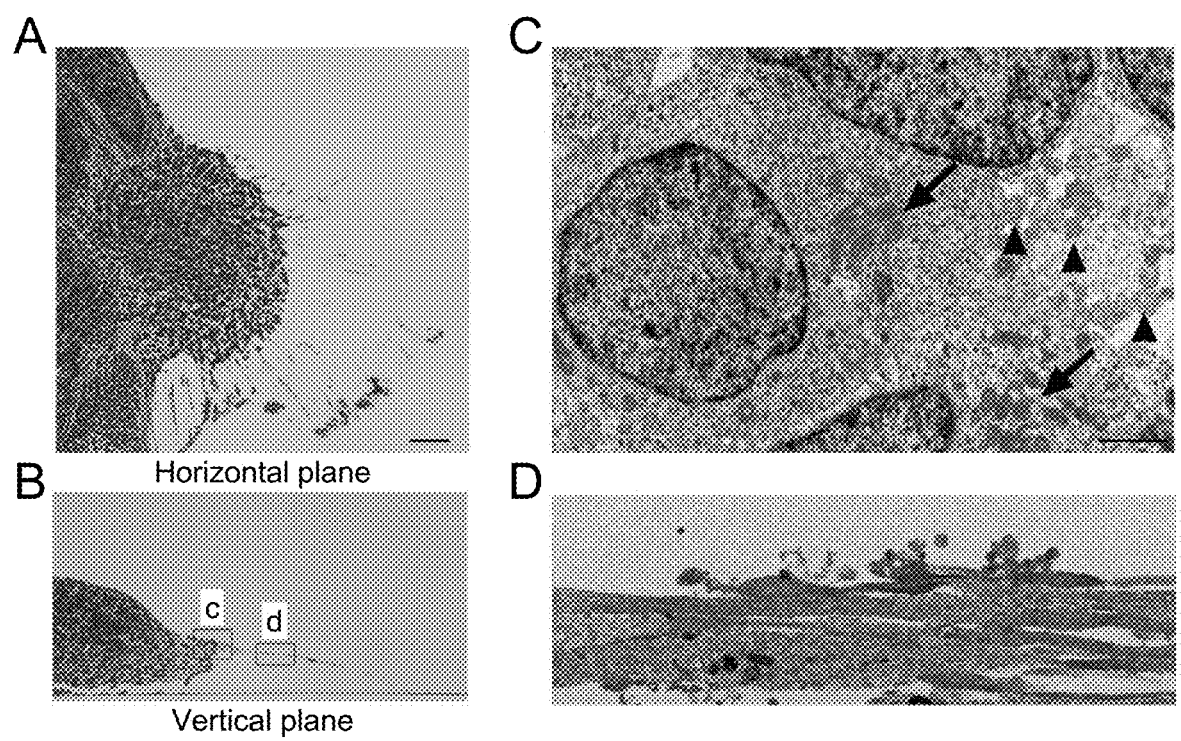
FIG. 11A and FIG. 11B show HE-staining images of axons elongated radially from the external margin of the cell clump corresponding to the optic vesicles (OV) protruding from the embryoid bodies (EB) (FIG. 11A: horizontal plane.
FIG. 11C shows an electron microscopic photograph of the retinal ganglion cell body corresponding to a region "c" shown in FIG. 11B (arrow: rough-surfaced endoplasmic reticulum; triangular arrow: axon projection; scale bar: 5 µm).
FIG. 11D shows an electron microscopic photograph of the retinal ganglion cell axon corresponding to a region "d" shown in FIG. 11B (scale bar: 5 µm).

The optic vesicles (OVs) adhered to the dish became complanate 26 to 29 days after the initiation of differentiation induction, the dish was filled with cells, and numerous axons developed radially from the outer margin on the dish surface. The cells in the clump were apparently different from those in the main bodies of the embryoid bodies, which were filled with small cells. The cells in the clump showed relatively large cell bodies (range: 16.1-23.6 μm; average: 21.6 μm, n=10) with clear cytoplasms and nuclei, such cells were in the spindle or round forms, and they were sometimes accompanied by prominent axons. These findings were identical to those concerning retinal ganglion cells (RGCs) in vivo, whose cell body sizes ranged from 12 μm to 25 μm. Notably, several cells located peripheral to the structure had Nissl bodies, which is considered to be characteristic of RGCs. The axons were found to be eosinophilic, have few branches, and grow directly and radially as with the axons of RGCs that would grow toward optic papilla in vivo (FIGS. 11A and 11B).

(2) Transmission Electron Microscopy
(Method)

Specimens were fixed with 2% glutaraldehyde in 100 mM cacodylate buffer for 2 hours and then with 1% osmium oxide in 100 mM cacodylate buffer for 1 hour. Specimens were then dehydrated through a graded series of alcohol to xylene, permeated with propylene oxide, and embedded in epoxy resin. Ultrathin sections of representative areas were stained with uranyl acetate and lead citrate and observed under a JEM-1200EX electron microscope (Japan Electron Optics Laboratory).
(Results)

Electron microscopy of the samples 35 days after the initiation of differentiation induction demonstrated that the retinal ganglion cells (RGCs) with axons were relatively large (range: 16.0-24.1 μm; average: 20.6 μm, n=10) and were stratified at the margin of the clump. These RGCs contained prominent rough endoplasmic reticulum (indicated with an arrow, FIG. 11C). The axons developed from the axon hillock (indicated with a triangular arrow, FIG. 11C) exhibited a characteristic conical cell body with many neurotubules but no rough-surfaced endoplasmic reticulum. Such finding was consistent with those concerning the retinal ganglion cells (RGCs) in vivo. The diameters of the axons varied (range: 1.7-2.2 μm; average: 1.8 μm, n=10), and the axons were not myelinated. These findings were identical to those concerning axons in the retinal nerve fiber layer and in the optic nerve located anterior to the lamina cribrosa (FIG. 11D).

Figure 12:
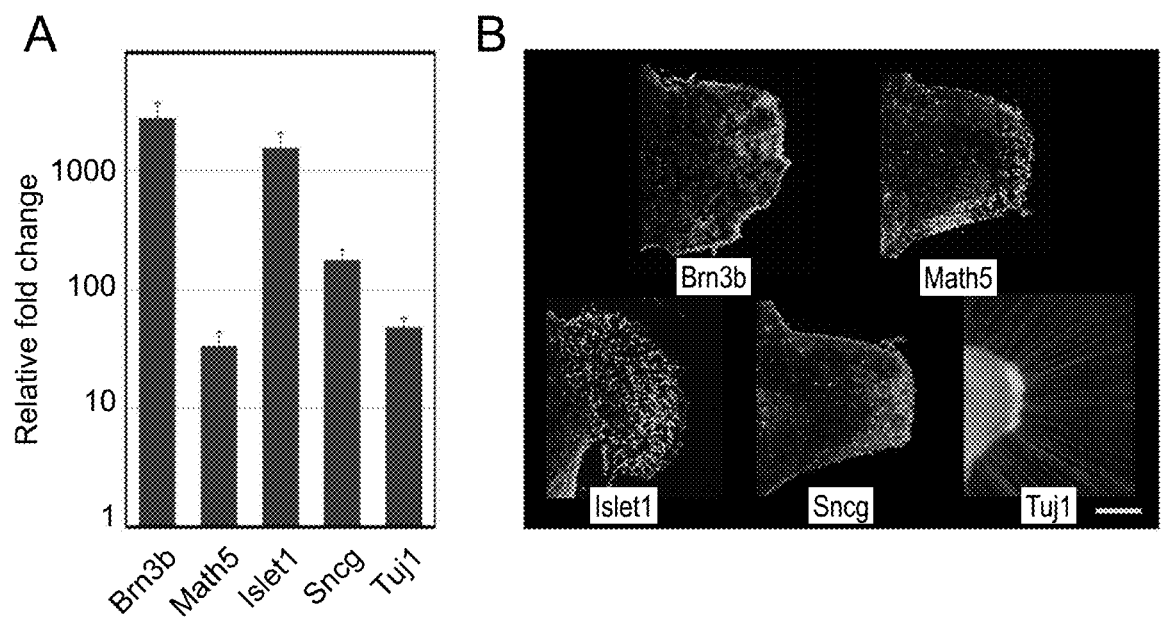
FIG. 12A shows the results of expression analysis of retinal ganglion cell-specific markers (Brn3b, Math5, Islet1, Sncg, and Tuj1) in the embryoid bodies 34 days after the initiation of differentiation induction from human iPS cells via RT-PCR (error bar: the mean of three independent tests±SD; vertical axis: semi-logarithmic scale). The mRNA expression level is normalized to the HPRT1 expression level, and it is expressed relative to the mRNA expression level measured 0 days after the initiation of differentiation induction, which is designated 1.
FIG. 12B shows immunostaining images of retinal ganglion cell-specific markers (Brn3b, Math5, Islet1, Sncg, and Tuj1) in the embryoid bodies 34 days after the initiation of differentiation induction from human iPS cells (scale bar: 100 µm).

(Example 6) Examination of Expression and Distribution of Retinal Ganglion Cell (RGC)-Specific Markers In order to confirm that the cells with axons in the margin of the clump differentiated from the optic vesicles (OVs) were retinal ganglion cells (RGCs), the expression and distribution of typical markers associated with RGCs (i.e., Brn3b, Math5, Islet1, γ-synuclein (Sncg), and β3-tublin (Tuj1)) were examined. Total RNA extracted 34 days after the initiation of differentiation induction from human iPS cells (Day 34) were subjected to real-time PCR (with the use of the primers shown in Table 1), and this real-time PCR revealed a 30-fold or more increase in expression levels of Brn3b, Math5, Islet1, Sncg, and Tuj1. Among these markers, Brn3b, which is the most RGC-specific marker, showed a nearly 3,000-fold increase in expression 34 days after the initiation of differentiation induction (Day 34), compared with Day 1 (FIG. 12A).

Immunostaining of Brn3b, Math5, Islet1, Sncg, and Tuj1 conducted 34 days after the initiation of differentiation induction revealed positive staining for all markers except for Tuj1 in the marginal portion of the clump, which was therefore thought to be the incipient RGC layer. Math5, an upstream transcription factor for Brn3b, and Sncg, another RGC marker and contributor to neurofilament integration, showed similar distributions in the marginal portion of the clump.

Islet1, a marker of RGCs and amacrine cells, was positive both in the marginal portion and further toward the interior of the clump, suggesting that amacrine cells also developed there. Notably, Brn3b-positive cells were apparently localized to the outermost marginal portion of the clump on the surface of the dish. This indicates that the long radial axons originate from the marginal portion of the clump and that the marginal portion is the retinal ganglion cell region (RGCRs) (FIG. 12B).

Figure 13:
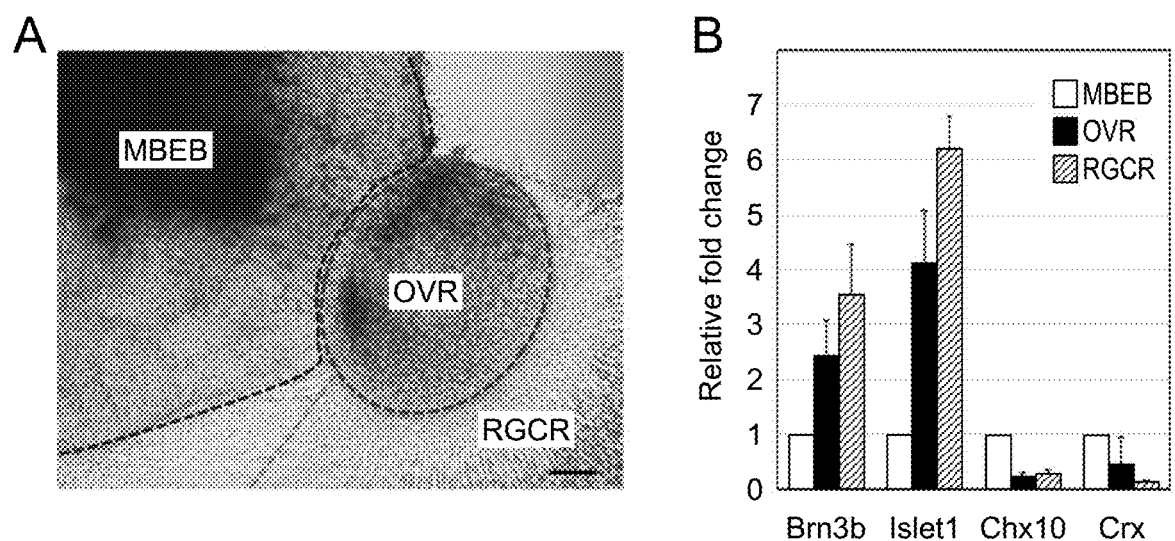
FIG. 13A shows an electron microscopic photograph of three regions in the embryoid bodies 34 days after the initiation of differentiation induction from human iPS cells (i.e., RGCR: retinal ganglion cell region; OVR: optic vesicle region; MBEB: main body of embryoid body) (scale bar: 100 µm).
FIG. 13B shows the results of expression analysis of retinal nerve markers (Brn3b, Islet1, Chx10, and Crx) in three regions in the retinal ganglion cells (i.e., RGCR: retinal ganglion cell region; OVR: optic vesicle region; MBEB: main body of embryoid body) via RT-PCR (error bar: the mean of three independent tests±SD; vertical axis: semi-logarithmic scale). The mRNA expression level is normalized to the HPRT1 expression level, and it is expressed relative to the mRNA expression level measured 0 days after the initiation of induction, which is designated 1.

In order to further confirm the presence of RGCs localized in the supposed RGCR, the structural complex subjected to adhesion culture was mechanically divided into three parts: the retinal ganglion cell region (RGCR); the optic vesicle region (OVR); and the main body of the embryoid body (MBEB) (FIG. 13A). The Brn3b expression level was nearly four-fold higher in the RGCR than in the MBEB (FIG. 13B). In addition, expression of Crx, which is a visual cell marker, was generally suppressed in the RGCR (FIG. 13B). These results apparently demonstrate that the RGCR is highly specified into the ganglion cell lineage. Islet1 (a marker for retinal ganglion cells and amacrine cells) was also upregulated in both the RGCR and the OVR (FIG. 13B). According to the results demonstrated above, Islet1-positive/Brn3b-negative cells are considered to be differentiated into amacrine cells, and Brn3b and its cofactor (Islet1) are considered to be associated with the RGC growth in the RGCR. In addition, the isolated RGCR was found to have survived for approximately 10 days after it was separated from the OVR. This suggests that mechanical purification of RGCs is possible after the growth of abundant axons.

(Example 7) Examination of Axonal Neurofilaments

Figure 14:
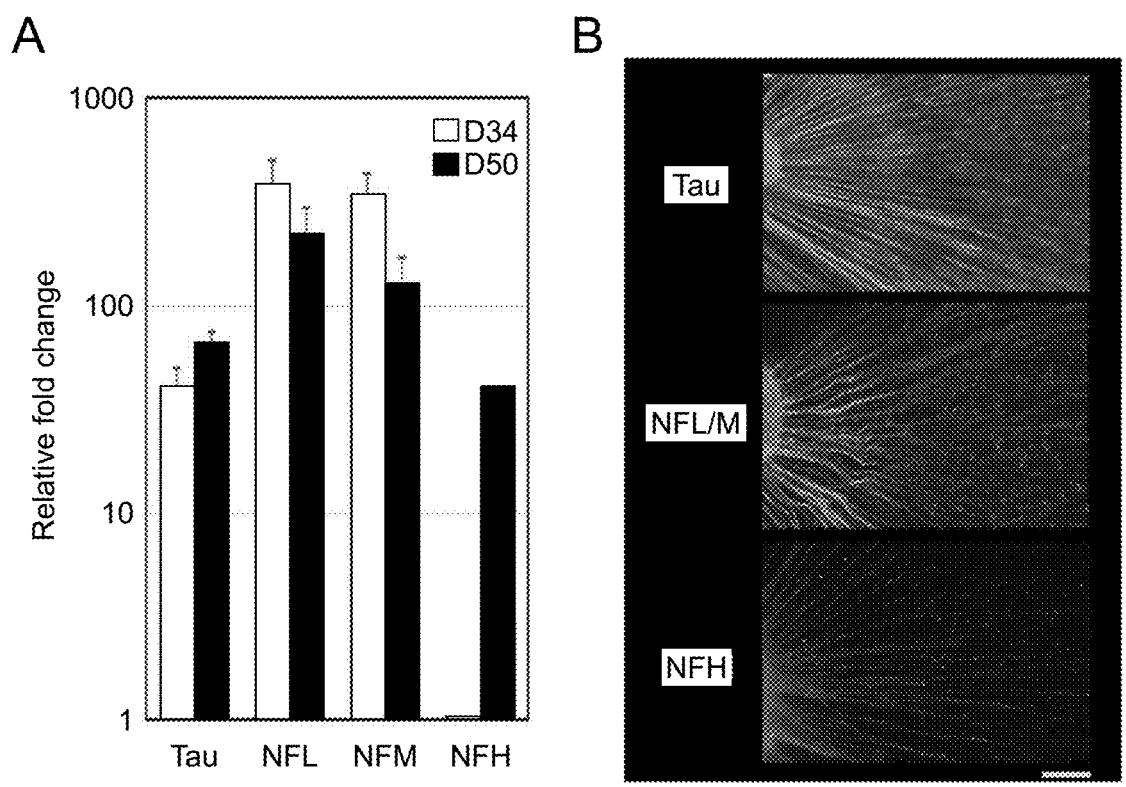
FIG. 14A shows the results of expression analysis of neurofilament markers (Tau, NFL, NFM, and NFH) in the embryoid bodies 34 days (D34) and 50 days (D50) after the initiation of differentiation induction from human iPS cells via RT-PCR. The mRNA expression level is normalized to the HPRT1 expression level, and it is expressed relative to the mRNA expression level of NFH measured 34 days after the initiation of differentiation induction, which is designated 1.
FIG. 14B shows immunostaining images of neurofilament markers (Tau, NFL/NFM, and NFH) in the embryoid bodies 34 days (D34) after the initiation of differentiation induction from human iPS cells (scale bar: 100 µm).

To confirm that the apparent axons emanating from the retinal ganglion cell region (RGCR) constitute typical axons, Tau and neurofilaments (NFs) were subjected to immunostaining (FIG. 14B). The time-series expression of all neurofilament components (i.e., neurofilament-light chain (NFL), neurofilament-medium chain (NFM), and neurofilament-heavy chain (NFH)) was studied in parallel (34 days (Day 34) and 50 days (Day 50) after the initiation of differentiation induction). Microtubules, neurofilaments (NFs), microtubule-associated proteins (MAPs), and actin play crucial roles in axonal development. Tau, which is a MAP, is known to contribute to polymerization, stabilization, and organization of microtubules and to promote axonal growth and effective axonal transport. The axons detected in this example were clearly stained for Tau. Thus, axonal transport was verified.

It is known that neurofilaments are the intermediate filaments of neurons and are abundant especially in the central nerve system (CNS) axons, where they develop as heteropolymers made of four subunits, namely, neurofilament-light chain (NFL), neurofilament-medium chain (NFM), neurofilament-heavy chain (NFH), and α-internexin. Neurofilaments are known to have essential roles in radial axonal growth and in axon caliber maintenance and the ability to transmit action potentials. In addition, both NFL and NFM appear early in retinogenesis, while synthesis of NFH is delayed. It was confirmed in this example that Tau, NFL, and NFM were already expressed at high levels 34 days after the initiation of differentiation induction (Day 34) and such expression was maintained up to Day 50. In contrast, expression of NFH was quite low 34 days after the initiation of differentiation induction (Day 34) and gradually increased up to Day 50 (FIG. 14A). As a result of immunostaining, specimens showed positive staining for Tau, NFL, and NFM but weak staining for NFH 34 days after the initiation of differentiation induction. Such results were in agreement with the results of the time course expression test (FIG. 14B).

(Example 8) Functional Analysis of Axons (1) Observation of Axonal Flow
(Method)

RGCs and their axons are known to be rich in mitochondria and to maintain homeostasis by axonal transport, as in other neurons. Neurotrophic tyrosine kinase receptor 1 (NTRK1), a member of the neurotrophic tyrosine kinase receptor family, is a nerve growth factor receptor. It is known to be expressed in RGCs, especially when the cells are damaged.

Using these two factors; i.e., NTRK1 and mitochondria, as tracers, a plasmid vector composed of GFP-NTRK1 with a CMV promoter and a plasmid vector composed of mCherry-mitochondria with a CMV promoter were directly introduced into the RGC cell body 34 days after the initiation of differentiation induction from human iPS cells (Day 34) via electroporation, and the anterograde rapid axonal transport was analyzed.

A specific test procedure is described below. The NTRK1 expression vector (RG213091; OriGene Technologies, Inc.), the pPAmCherry-Mito Vector (Takara Bio Inc.), and the pcDNA™6.2/C-EmGFP Vector (Invitrogen Corporation) were electroporated into cultured cells. For electroporation, NEPA21 (Nepa Gene Co., Ltd.) with platinum electrodes was used. The cultured colony was injected with a Fast Green-dyed DNA solution using a sharp glass pipette, placed between the electrodes, and electroporated with voltage pulses (poring pulse: voltage 100 V, width 2.5 ms, interval 50 ms, two times; transfer pulse: voltage 20 V, width 50 ms, interval 50 ms, five times). The cultured cells were then allowed to develop in humidified incubators. Observations were made with an IX71 inverted research microscope (Olympus Corporation). To detect a time series of axonal transport, also, Alexa-Fluo-555 conjugated cholera toxin, which is known as a tracer of axonal transport, was administrated.
(Results)

Figure 15:
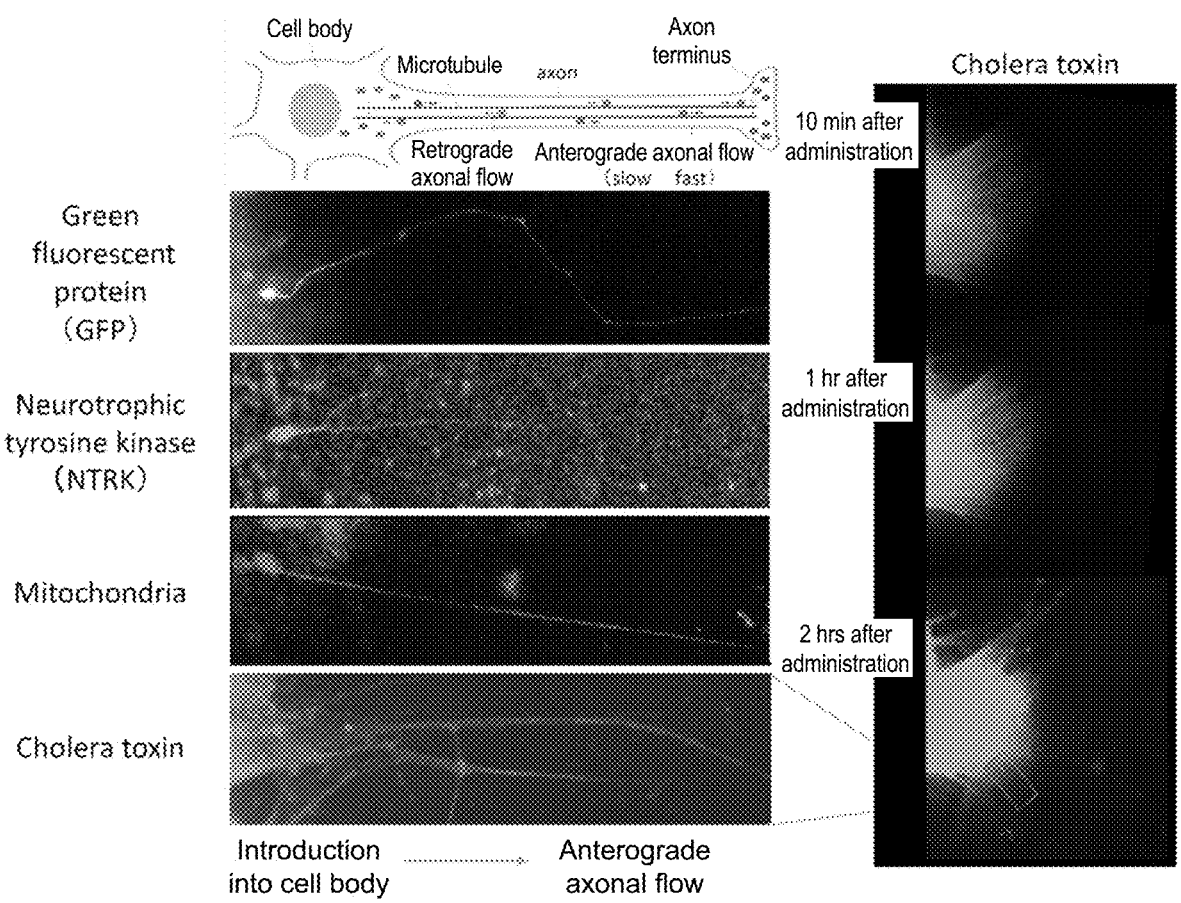
FIG. 15 shows the results of observation of the anterograde axonal flow of the embryoid bodies 34 days after the initiation of differentiation induction from human iPS cells (GFP (control), NTRK1, a mitochondria-specific protein is introduced into a cell body via electroporation, and cholera toxin is injected via micropipetting into a region at the colony margin in which cell bodies are mainly distributed).

Axonal transport showed two characteristic flows, the slow flow and the fast flow, both of which had anterograde and retrograde components. Several axons demonstrated anterograde axonal flow approximately 7 to 10 hours after introduction. Both NTRK1 and mitochondria were expressed in axons and the cell bodies. The presence thereof in axons indicates the anterograde rapid axonal transport (FIG. 15, left). Also, cholera toxin was injected into a region at the colony margin in which cell bodies are mainly distributed using a micropipette and incorporated into the cell bodies. As a result, anterograde axonal transport (fast slow) was apparently observed in RGCR, and cholera toxin was transported from the cell bodies to the marginal regions of axons by means of anterograde axonal transport within two hours after the injection thereof (FIG. 15, right).

(2) Electrophysiological Recording
(Method)

Whether or not the retinal ganglion cells (RGCs) induced to differentiate from human iPS cells by the method of the present invention would generate action potentials was analyzed. Colonies were cultured on a filter paper made of mixed cellulose esters (0.2-μm pore size; Advantech Co., Ltd.) for 1 week. After the colony-bearing filter paper was removed from the medium, suction was applied to the bottom of the filter to cause the colonies to attach firmly. Slices (200-μm thick) were cut vertically with a tissue chopper and fixed to the glass bottom of a recording chamber having a volume of 1.5 mL with a small amount of silicone grease (Dow Corning Corporation). All experiments were performed at physiological temperatures (35° C. to 37° C.) using a ThermoClamp-1 (AutoMate Scientific, Inc.). The chamber was continuously perfused at 1.5 mL/min with an extracellular solution containing 120 mM NaCl, 3 mM KCl, 2.5 mM $CaCl_2$, 1 mM $MgCl_2$, 10 mM glucose, and 25 mM $NaHCO_3$ equilibrated with 95%/5% $O_2/CO_2$ (pH 7.4). Whole-cell patch-clamp recordings were made from the retinal ganglion cells located on the outer perimeter of the cultured colony. Recordings were performed with an Axopatch 200B amplifier (Molecular Devices) using pCLAMP 9.2 software (Molecular Devices). The slice preparations were visualized using an upright microscope (BX50WI; Olympus Corporation) equipped with DIC optics and a 60× water-immersion objective. The voltage or current trace was low-pass filtered (Bessel filter, corner frequency 10 kHz) and sampled at 20 to 50 kHz with a Digidata 1322A interface (Molecular Devices). Voltage-dependent $Na^+$ currents were measured with leakage and capacitive current subtraction (P/−5 protocol) and were averaged over three trials. In some experiments, 1 μM tetrodotoxin (TTX) was added to the extracellular solution to block voltage-dependent $Na^+$ channels. The recording pipettes (6-8 MΩ) were filled with an intracellular solution containing 120 mM potassium gluconate, 6 mM KCl, 2 mM NaCl, 1 mM $CaCl_2$, 1 mM $MgCl_2$, 5 mM EGTA, 10 mM HEPES, 4 mM $Na_2ATP$, and 0.5 mM GTP (pH 7.2). In all experiments, Lucifer Yellow CH dilithium salt (LY; 0.05%) was added to the intracellular solutions to visualize the morphology of the recorded cells. Liquid junction potentials (−11 mV) were corrected. The average series resistance (Rs) was 29.4±4.77 MΩ (n=5). Rs was compensated by 40%. Data with Rs values of more than 35 MΩ were excluded from the analyses. The average membrane capacitance during the recordings was 7.20±2.84 pF (n=5). Current and voltage data were acquired using pCLAMP 9.2 software and saved on a custom-built personal computer (Physio-Tech Co., Ltd.). Analyses were performed with Clampfit 9.2 (Molecular Devices) and OriginPro 8J (OriginLab Corporation). Images of LY-filled cells were captured using a high-gain color camera (HCC-600; Flovel Co., Ltd.) and saved using INFO.TV Plus software (Infocity, Inc.). The images were adjusted for brightness and contrast and complemented by pasting in a part of another image obtained from the slice preparation with a different depth using Photoshop CS6 software (Adobe Systems). All data are presented as means±SDs.

(Results)

Figure 16:
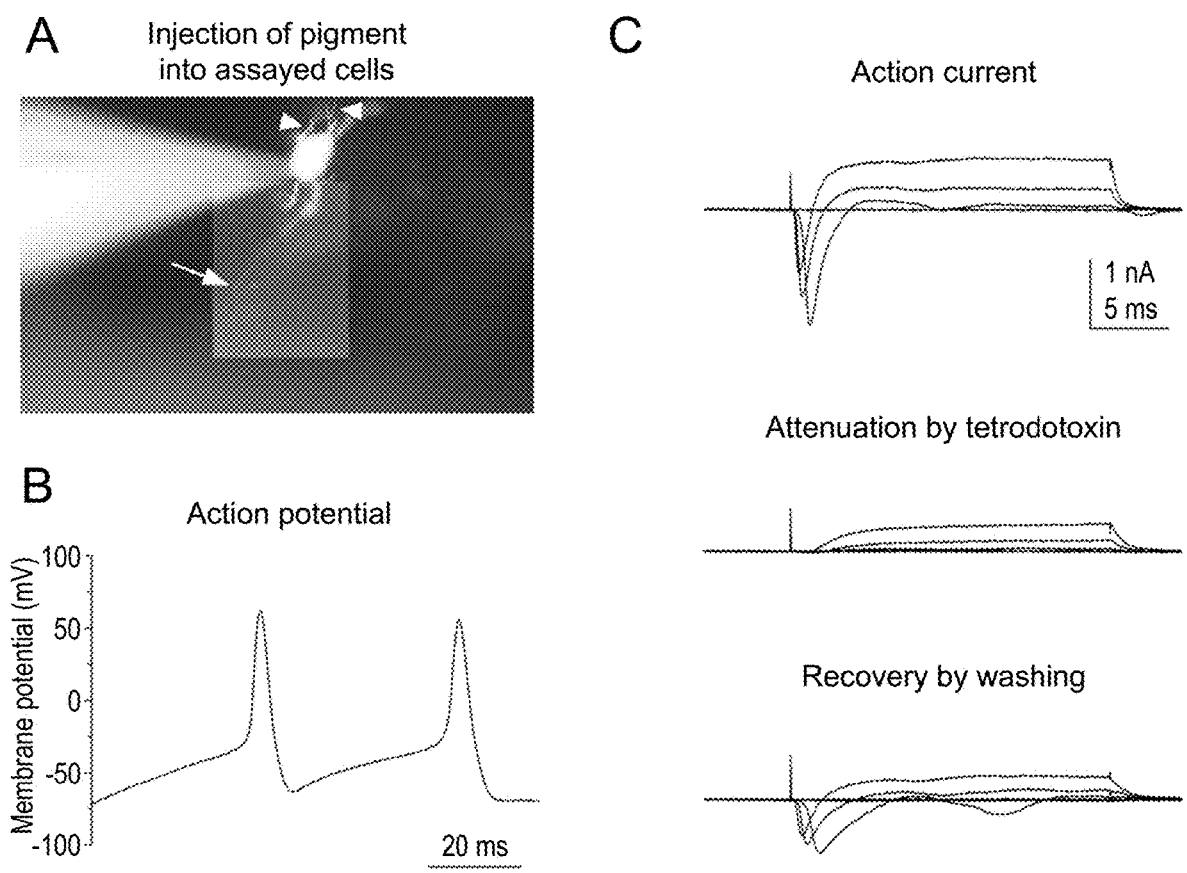
FIG. 16 shows the results of electrophysiological analysis of retinal ganglion cells induced to differentiate from human iPS cells.

The retinal ganglion cells (RGCs) each had a long axon process extending toward the filter paper side and possessed some dendritic processes (FIG. 16A). In the electrophysiological analysis of cells with axonal process, action potentials were continuously exhibited in response to current injection through the recording pipette in the current clump mode (4 cells out of 5 cells) (FIG. 16B). The resting membrane potential and the amplitude of the first action potential were −81.8±26.8 mV and 56.8±24.6 mV, respectively (n=4). The cells that generated action potentials first exhibited the outward current and then tetrodotoxin (TTX)-sensitive, sodium-dependent currents with a maximum amplitude of 1,248±573 pA (n=4) (FIG. 16C).

(Example 9) Preparation of Glaucoma Cell Model and Confirmation of Effectiveness Thereof (1) Preparation of Glaucoma Cell Model Human iPS cells were induced to differentiate into retinal ganglion cells in the same manner as in Example 1, embryoid bodies that had been subjected to floating culture were transferred to a 24-well plate and subjected to adhesion culture using a neuronal maintenance medium (GlutaMAX-containing D-MEM/F12, N2 Supplements (Life Technologies), 1% FBS), and retinal ganglion cell (RGC) colonies with elongated axons were then transferred to a pressure incubator 6 days after the initiation of adhesion culture (33 days after the initiation of differentiation induction). After culture was conducted at a pressure of 60 mmHg for 12 hours, colonies were recovered, RNAs were extracted from the cells using an RNeasy Mini Kit (Qiagen), RNAs were reversely transcribed into cDNAs, and real-time PCR (40 cycles of 95° C. for 15 seconds and 60° C. for 30 seconds,) was carried out using the StepOnePlus real-time PCR system (Life Technologies) and the sets of primers described below, so as to assay the expression levels of apoptosis-associated genes; Bax, Caspase 3 or Caspase 8, and Bcl2 genes. Immunostaining for apoptosis detection (TUNEL) was carried out using the ApopTag plus fluorescein in situ apoptosis detection kit (Merck Millipore) in accordance with the included protocols.

Primer Set for Bax Gene Amplification

```
Forward primer:
                            (SEQ ID NO: 51)
5'-CCCGAGAGGTCTTTTTCCGAG-3'

Reverse primer:
                            (SEQ ID NO: 52)
5'-CCAGCCCATGATGGTTCTGAT-3'
```

Primer Set for Caspase 3 Gene Amplification

```
Forward primer:
                                      (SEQ ID NO: 53)
5'-CATGGAAGCGAATCAATGGACT-3'

Reverse primer:
                                      (SEQ ID NO: 54)
5'-CTGTACCAGACCGAGATGTCA-3'
```

Primer Set for Caspase 8 Gene Amplification

```
Forward primer:
                                      (SEQ ID NO: 55)
5'-CTCCCCAAACTTGCTTTATG-3'

Reverse primer:
                                      (SEQ ID NO: 56)
5'-AAGACCCCAGAGCATTGTTA-3'
```

Primer Set for Bcl2 Gene Amplification

```
Forward primer:
                                      (SEQ ID NO: 57)
5'-GGTGGGGTCATGTGTGTGG-3'

Reverse primer:
                                      (SEQ ID NO: 58)
5'-CGGTTCAGGTACTCAGTCATCC-3'
```

Figure 17:
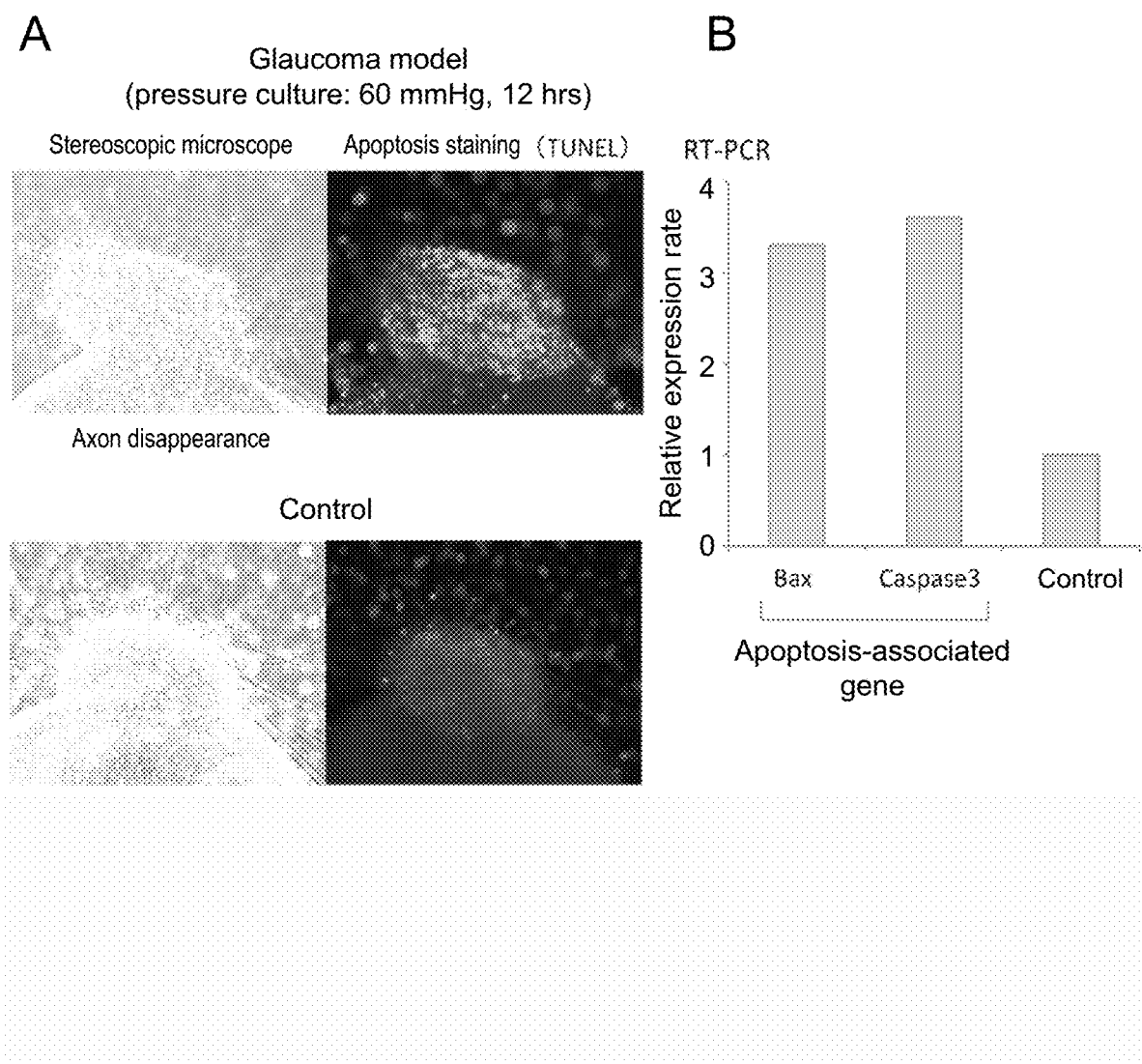
FIG. 17A shows a stereomicroscopic photograph of glaucoma cell models and images of apoptosis staining.
FIG. 17B shows the results of expression analysis of apoptosis-associated markers (Bax and Caspase3) in glaucoma cell models via RT-PCR.

In comparison with the unpressurized RGCs (the control cells), axons disappeared in the RGCs that had been continuously pressurized at 60 mmHg for 12 hours, and significantly increased apoptotic cells were detected by the TUNEL method (FIG. 17A). In addition, enhanced expression of apoptosis-promoting genes (Bax and Caspase 3 genes) was detected via RT-PCR analysis (FIG. 17B).

(2) Confirmation of Effects of Neurotrophic Factors

Human iPS cells were induced to differentiate into retinal ganglion cells in the same manner as in Example 1, embryoid bodies that had been subjected to floating culture were transferred to a 24-well plate and subjected to adhesion culture using a neuronal maintenance medium (GlutaMAX-containing D-MEM/F12, N2 Supplements (Life Technologies), 1% FBS), the medium was exchanged with a fresh medium prepared by supplementing the neuronal maintenance medium with the 100 ng/ml neurotrophic factor (brain-derived neurotrophic factor (hereafter referred to as "BDNF") and the ciliary neurotrophic factor (hereafter referred to as "CNTF") 4 days after the initiation of adhesion culture (31 days after the initiation of differentiation induction), and retinal ganglion cell (RGC) colonies with elongated axons were then transferred to a pressure incubator. After culture was conducted at a pressure of 60 mmHg for 12 hours, colonies were recovered, RNAs were extracted from the cells using an RNeasy Mini Kit (Qiagen), and the expression levels of Bax, Caspase 3 or Caspase 8, and Bcl2 genes were assayed via RT-PCR in the same manner as in (1) above.

Figure 18:
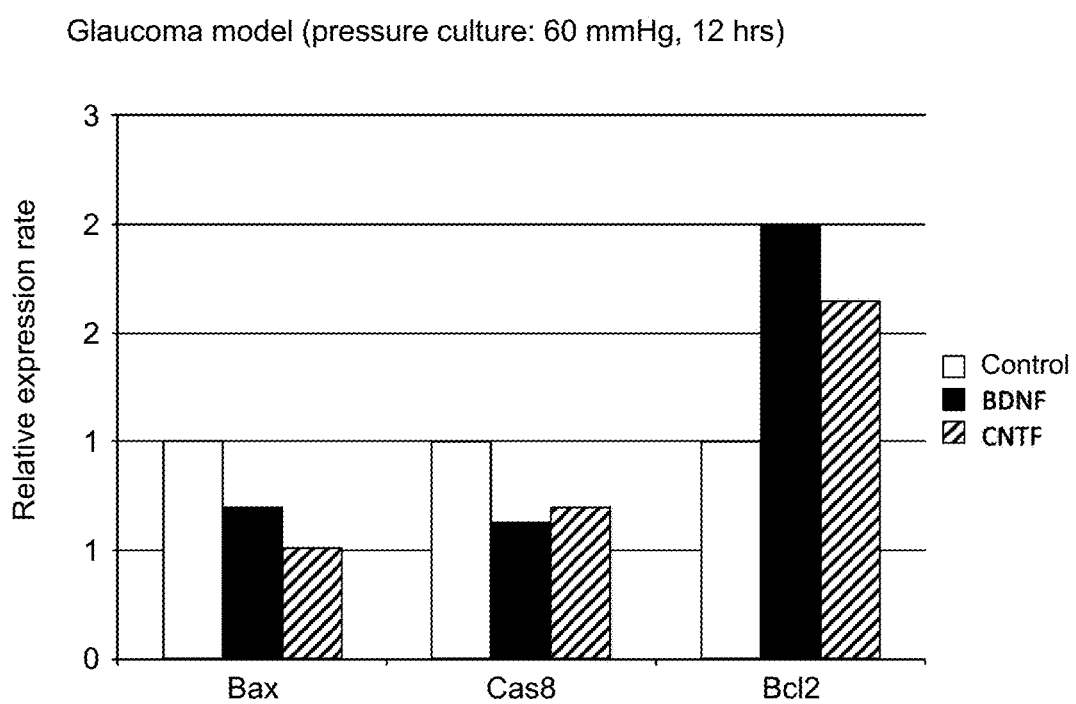
FIG. 18 shows the results of evaluation of effects of neurotrophic factors (BDNF and CNTF) on glaucoma cell models via expression analysis of apoptosis-associated markers (Bax, Caspase8, and Bcl2) via RT-PCR.

In comparison with the control cells (without administration), expression of apoptosis-promoting genes (Bax and Caspase 8) was remarkably suppressed, and expression of apoptosis-suppressing genes (Bcl2) was enhanced, as a result of BDNF and CNTF administration (FIG. 18).

(Example 10) Preparation of Cell Models of Congenital Iridosteresis/Optic Nerve Hypoplasia and Confirmation of Effectiveness Thereof (1) Preparation of Cell Models of Congenital Iridosteresis/Optic Nerve Hypoplasia Regarding two cases in which Pax6 gene mutation was observed (Case 1 and Case 2), disease iPS cells of optic nerve hypoplasia involved with congenital aniridia were prepared from conjunctival tissue samples obtained via surgery. A mutation of Case 1 was 3' splicing defect c.774+1G>T of Exon 5, and that of Case 2 was Q277X, both of which were nonsense mutations. iPS cells were prepared via introduction of four factors (OCT3/4, SOX2, KLF4, and C-MYC) (Yamanaka et al.) in accordance with a conventional technique. These disease iPS cells were induced to differentiate into retinal ganglion cells in the same manner as in Example 1, and embryoid bodies that had been subjected to floating culture were transferred to a 24-well plate and subjected to adhesion culture using a neuronal maintenance medium (GlutaMAX-containing D-MEM/F12, N2 Supplements (Life Technologies), 1% FBS). The retinal ganglion cell (RGC) colonies were observed under a microscope 8 days after the initiation of adhesion culture (35 days after the initiation of differentiation induction) in the same manner as in Example 1, and the expression levels of genes associated with retinal ganglion cell formation (Brn3b and Math5) were assayed via RT-PCR.

Figure 19:
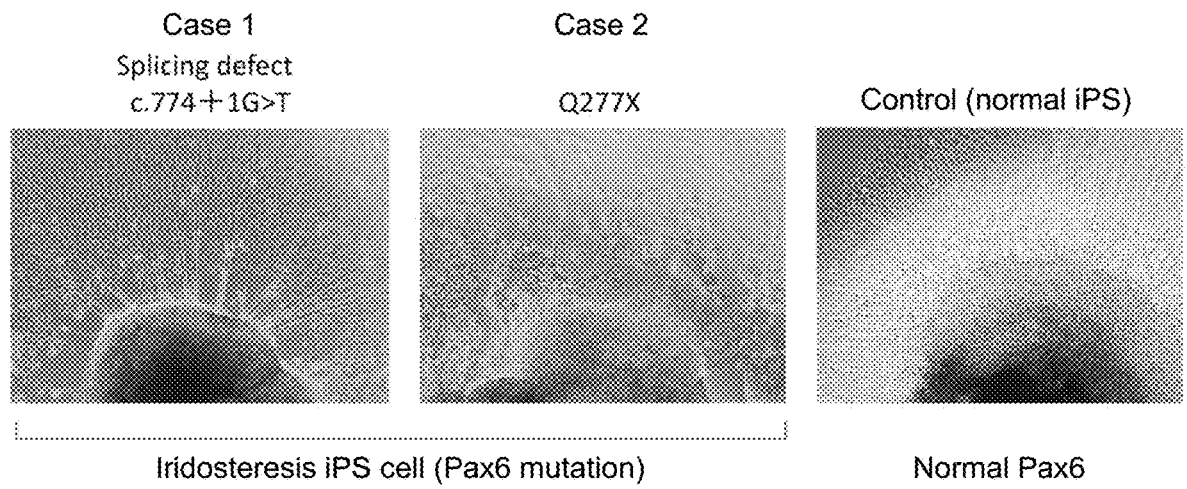
FIG. 19A shows a stereomicroscopic images of iridosteresis and optic nerve hypoplasia cell models (c.774+1G>T mutation: cells induced to differentiate from iPS cells with iridosteresis (Pax6 mutation); Q227X: cells induced to differentiate from iPS cells with iridosteresis (Pax6 mutation); control: cells induced to differentiate from normal iPS cells).
FIG. 19B shows the results of expression analysis of genes for retinal ganglion cell formation (Brn3b and Math5) in iridosteresis and optic nerve hypoplasia cell models via RT-PCR (c.774+1G>T mutation: cells induced to differentiate from iPS cells with iridosteresis (Pax6 mutation); Q227X: cells induced to differentiate from iPS cells with iridosteresis (Pax6 mutation); control: cells induced to differentiate from normal iPS cells).
Figure 19:
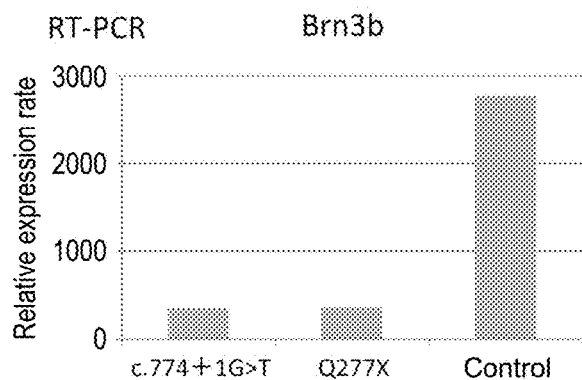
Figure 19:
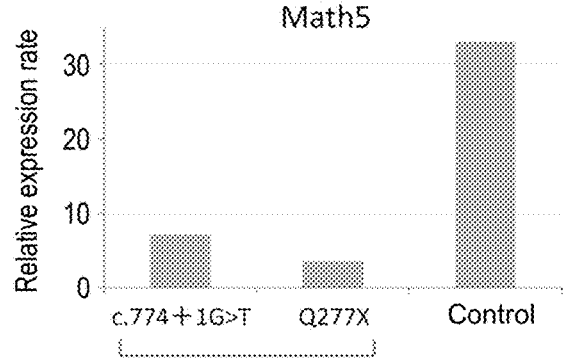

In comparison with the RGCs induced to differentiate from normal iPS cells in the same manner (i.e., the control cells), axon elongation was very poor in the RGCs induced to differentiate from disease iPS cells (FIG. 19A). In addition, expression of the genes associated with retinal ganglion cell formation (Brn3b and Math5) was more suppressed in the RGCs induced to differentiate from disease iPS cells than in the RGCs induced to differentiate from normal iPS cells (the control cells) (FIG. 19B).

(2) Confirmation of Effects of Neurotrophic Factors (Recovery of the Nerve Elongation)

The disease iPS cells of iridosteresis (c.774+1G>T mutation) of Case 1 or normal iPS cells were induced to differentiate into retinal ganglion cells in the same manner as in Example 1, and embryoid bodies that had been subjected to floating culture were transferred to a 24-well plate and subjected to adhesion culture using a neuronal maintenance medium (GlutaMAX-containing D-MEM/F12, N2 Supplements (Life Technologies), 1% FBS). The medium was exchanged with a fresh medium prepared by supplementing the neuronal maintenance medium with 100 ng/ml neurotrophic factors (BDNF and CNTF) 4 days after the initiation of adhesion culture (31 days after the initiation of differentiation induction), and culture was continued for 10 days. Thereafter, the retinal ganglion cell (RGC) colonies were observed under the stereoscopic microscope, so as to observe axon elongation. Also, the expression levels of transcription factors associated with retinal ganglion cell formation (Brn3b, Math5, Islet1, and Tuj1) and the retinal nerve fiber structural genes (Tau and NFL) were assayed via RT-PCR.

Figure 20:
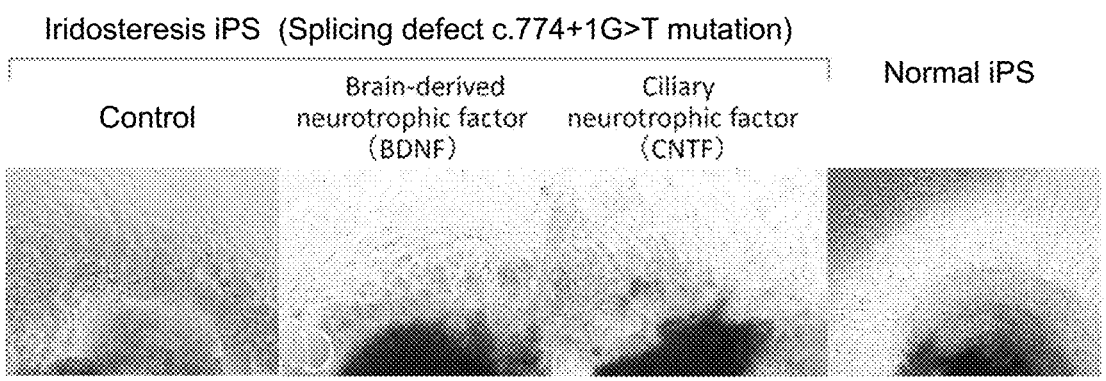
FIG. 20A shows the results of evaluation of effects of neurotrophic factors (BDNF and CNTF) on iridosteresis cell models (c.774+1G>T mutation) (i.e., axonal growth promotion) via microscopic observation.
FIG. 20B shows the results of evaluation of effects of neurotrophic factors (BDNF and CNTF) on iridosteresis cell models (c.774+1G>T mutation) via expression analysis of transcription factors for retinal ganglion cell formation (Brn3b, Math5, Islet1, and Tuj1) and structural genes of retinal nerve fibers (Tau and NFL) via RT-PCR.
Figure 20:
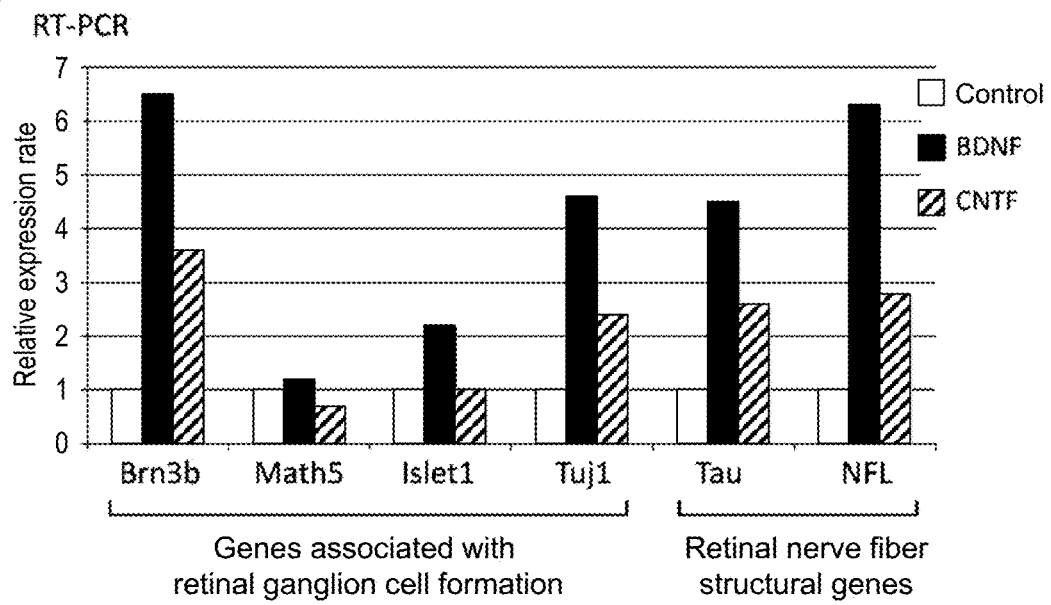

While axon elongation was less sufficient in comparison with that of retinal ganglion cells derived from normal iPS cells, axon elongation became more sufficient upon administration of BDNF or CNTF than that of the retinal ganglion cells derived from iPS cells of iridosteresis (c.774+1G>T mutation) to which neither BDNF nor CNTF had been administered (control cells) (FIG. 20A).

RT-PCR demonstrated that expression levels of Brn3b, Math5, Islet1, Tuj1, Tau, and NFL were enhanced as a result of BDNF administration and expression levels of Brn3b, Tuj1, Tau, and NFL were enhanced as a result of CNTF administration. Since the expression levels of transcription factors associated with retinal ganglion cell formation was enhanced (FIG. 20B), BDNF and CNTF are considered to act on retinogenesis genes located upstream of the genes associated with retinal ganglion cell formation.

(Example 11) Effects of Neurotrophic Factors or Neural Inhibitors on Axon Elongation Human iPS cells (normal) were induced to differentiate into retinal ganglion cells in the same manner as in Example 1, and embryoid bodies that had been subjected to floating culture were transferred to a 24-well plate and subjected to adhesion culture using a neuronal maintenance medium (GlutaMAX-containing D-MEM/F12, N2 Supplements (Life Technologies), 1% FBS). The medium was exchanged with a fresh medium prepared by supplementing the neuronal maintenance medium with 100 ng/ml neurotrophic factors (BDNF and CNTF) or neural inhibitors (Sema3A) 4 days after the initiation of adhesion culture (31 days after the initiation of differentiation induction), and culture was continued for 10 days. Thereafter, the retinal ganglion cell (RGC) colonies were observed under the microscope in the same manner as in Example 1, and the expression level of the Brn3b gene was assayed via RT-PCR.

Figure 21:
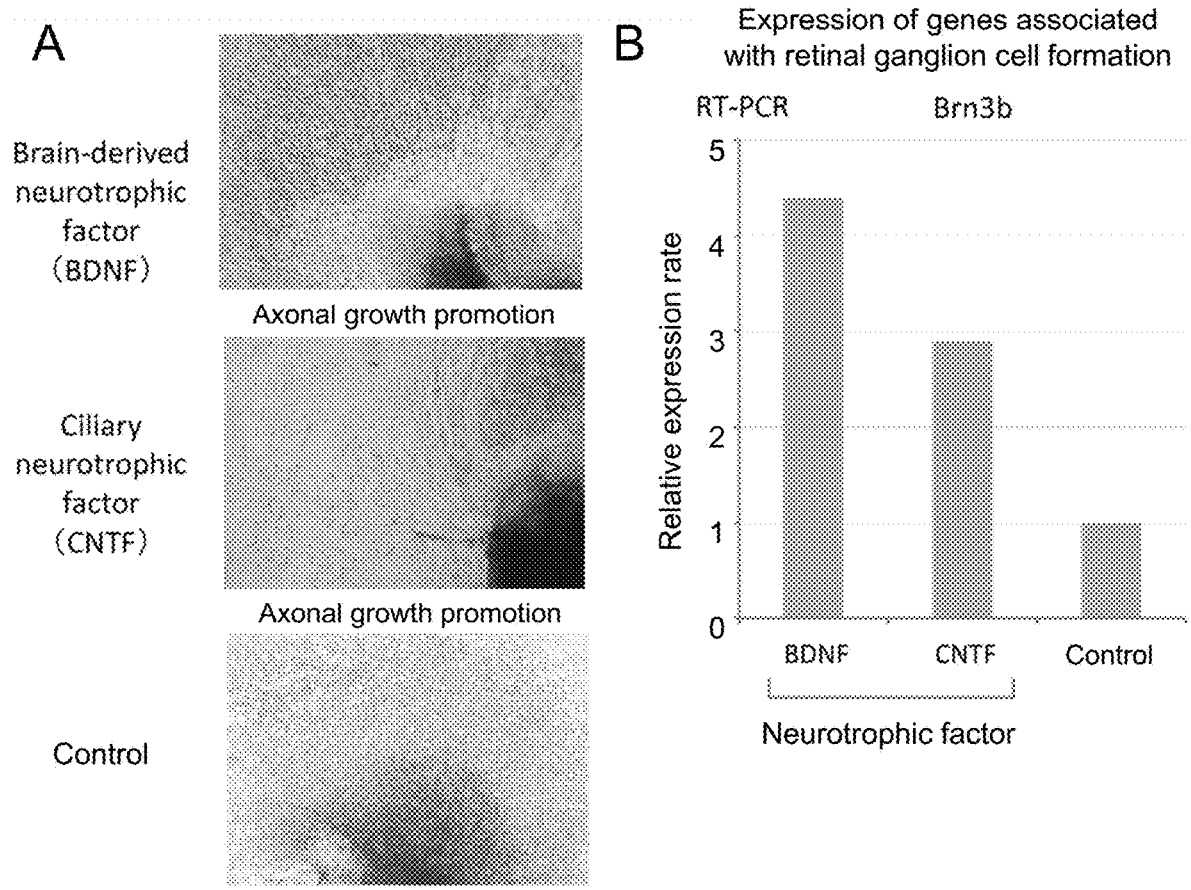
FIG. 21A shows the results of evaluation of effects (i.e., axonal growth promotion) of neurotrophic factors (BDNF and CNTF) on retinal ganglion cells induced from human iPS cells (i.e., normal cell models) via microscopic observation.
FIG. 21B shows the results of evaluation of effects of neurotrophic factors (BDNF and CNTF) on retinal ganglion cells induced from human iPS cells (i.e., normal cell models) via expression analysis of retinal ganglion cell-specific marker (Brn3b) via RT-PCR.

Axon elongation became more sufficient upon administration of BDNF and CNTF than in the control cells (without administration) (FIG. 21A). In comparison with the control cells (without administration), also, expression of retinal ganglion cell-specific marker (i.e., the Brn3b gene) was remarkably enhanced as a result of administration of BDNF and CNTF (FIG. 21B).

Figure 22:
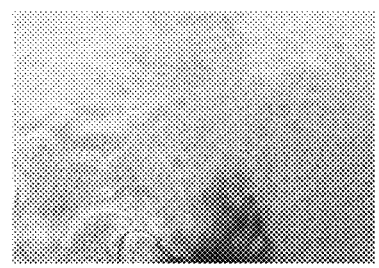
FIG. 22A shows the results of evaluation of effects (i.e., axonal growth promotion) of neural inhibitors (Sema3A) on retinals ganglion cells induced from human iPS cells (i.e., normal cell models) via microscopic observation.
FIG. 22B shows the results of evaluation of effects of neural inhibitors (Sema3A) on retinal ganglion cells induced from human iPS cells (i.e., normal cell models) via expression analysis of retinal ganglion cell-specific marker (Brn3b) via RT-PCR.
Figure 22:
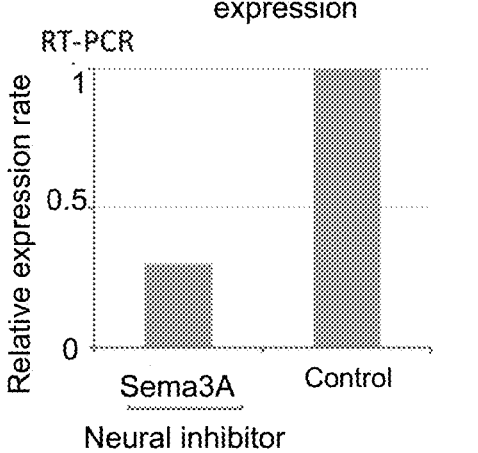

Upon administration of Sema3A, however, axon elongation was significantly suppressed in comparison with the control cells (without administration) (FIG. 22A). Also, expression of retinal ganglion cell-specific marker (i.e., the Brn3b gene) was significantly suppressed in comparison with the control cells (without administration) (FIG. 22B).

According to the results demonstrated above, the retinal ganglion cells prepared by the method of the present invention can be used for screening of drugs capable of protecting or regenerating retinal ganglion cells or dynamic evaluation of retinal ganglion cells against neural inhibitors with the use of axon elongation thereof or the retinal ganglion cell-specific marker (Brn3b gene) as the indicator.

(Example 12) Confirmation of Survival and Function in Retinal Ganglion Cell-Implanted Mice (Method)
The retinal ganglion cells (RGCs) induced to differentiate from GFP-mouse-derived ES cells in the same manner as in Example 2 were implanted into the vitreous cavities of the B6 mice or Wister rats. These animals were subjected to conjunctival incision in one of the eyes (the right eye) 24 to 36 hours before the experiment, and the retrobulbar optic nerves were exposed and crushed using forceps. Thus, animal models of optic neuropathy were prepared. In the case of rats, Cyclosporin A was intramuscularly injected at 20 mg/kg/day from 1 day before implantation to 1 week after implantation. Mice were not subjected to immunodepression. Colonies to be implanted were selected when axons began to extend 1 to 3 days after embryoid bodies were subjected to adhesion culture, following floating culture, in accordance with the method described in Example 2.

Figure 23:
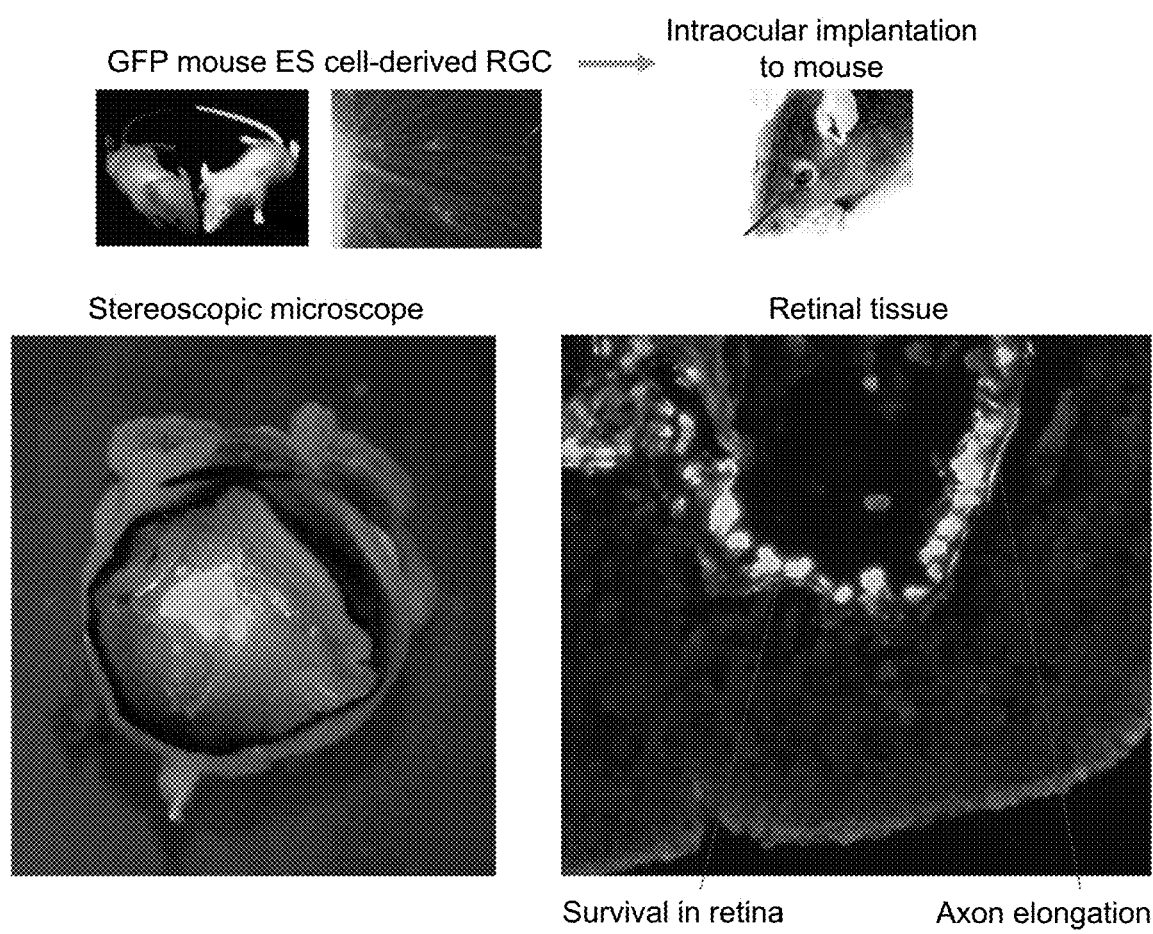
FIG. 23 shows the results of an intraocular implantation test of retinal ganglion cells produced by the method of the present invention in mouse eyes.

After gas anesthetics were introduced, the right eye and the areas surrounding the right eye were disinfected with the use of an Isodine solution, the conjunctiva was incised, and the sclera of a region presumed to be the ciliary body was incised using a 25G needle. Colonies were inserted into the vitreous body through the scleral wounds using forceps, the sclera was sutured with the 10/0 nylon thread, the conjunctiva was sutured with the 9/0 silk thread, and antibiotic ointments were applied to complete the surgery. The animal was euthanized under deep anesthesia 7 to 10 days after implantation, and the right eyeball was extirpated and then fixed with 4% paraformaldehyde. The eyeball was incised for 360 degrees at the ciliary body, so as to remove the anterior eye and the crystalline lens, and the retina of the cup-shaped posterior eye was observed under the fluorescent stereoscopic microscope. The specimens in which GFP was observed were frozen, and the resulting frozen specimens were observed under the fluorescent microscope.
(Results)
As a result of observation under the fluorescent stereoscopic microscope, GFP-positive tissue was detected on the retina. As a result of observation of the frozen specimens under the fluorescent microscope, survival of GFP-positive retinal ganglion cells (RGCs) was detected in the retina, and axon elongation was further detected in the retina (FIG. 23).

Figure 24:
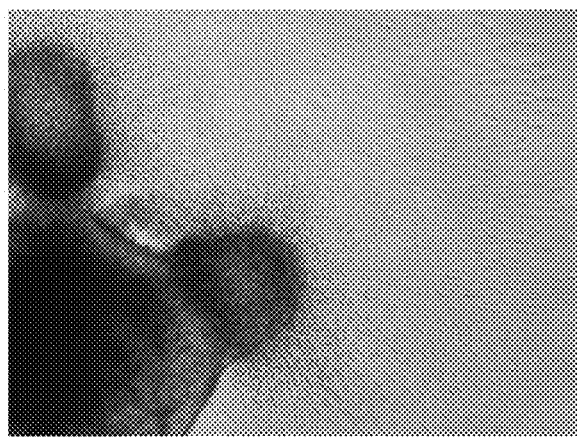
FIG. 24A shows a stereomicroscopic photograph of the embryoid bodies induced to differentiate from human ES (hES) cells (40×) (30 days after the initiation of differentiation induction and 3 days after the initiation of adhesion culture).
FIG. 24B shows the results of expression analysis of retinal differentiation-associated transcription factors (Rx, Pax6, Chx10, and Brn3b) in embryoid bodies conducted 24 days and 34 days after the initiation of differentiation induction from human ES (hES) cells (7 days after the initiation of adhesion culture) via RT-PCR. The mRNA expression level is normalized to the HPRT1 expression level, and it is expressed relative to the mRNA expression level measured 0 days after the initiation of differentiation induction, which is designated 1.
Figure 24:
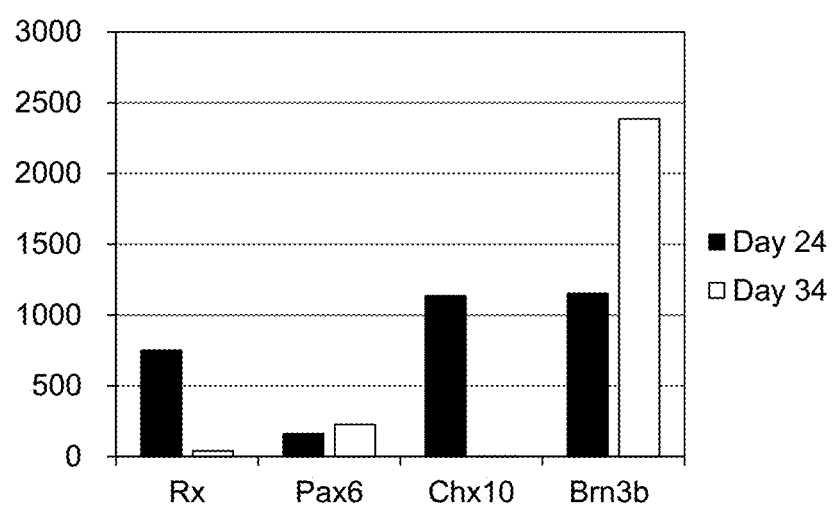

(Example 13) Preparation of Retinal Ganglion Cells from Human ES Cells and Analysis Thereof Retinal ganglion cells were induced to differentiate from human ES cells (obtained from the Riken BioResource Center (RIKEN BRC)) in the same manner as in Example 1, except that human ES cells were used instead of human iPS cells. FIG. 24A shows the stereomicroscopic image of embryoid bodies 30 days after the initiation of differentiation induction (3 days after the initiation of adhesion culture). When retinal ganglion cells were induced to differentiate from human ES cells, also, axons radially developed from the margin of embryoid bodies were observed. Also, the expression levels of transcription factors associated with retinal differentiation (i.e., Rx, Pax6, Chx10, and Brn3b) were assayed 24 days after the initiation of differentiation induction and 34 days after the initiation of differentiation induction (7 days after the initiation of adhesion culture) via real-time PCR with the use of the primers shown in Table 1 under the same conditions as in Example 1. As a result, expression of all the transcription factors was detected 24 days after the initiation of differentiation induction, and the expression level of the RGC-specific marker gene (Brn3b) was remarkably enhanced after the cells were transferred to adhesion culture (FIG. 24B).

Figure 25:
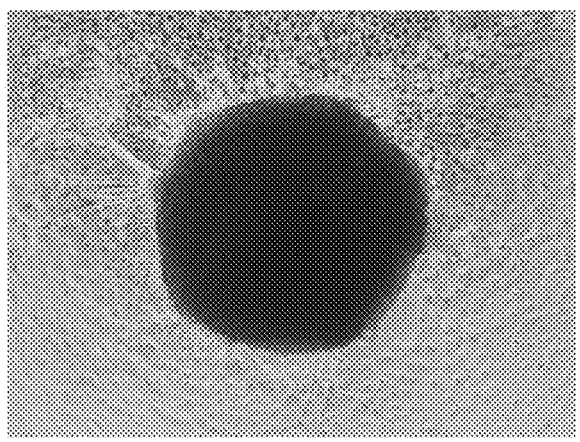
FIG. 25A shows a stereomicroscopic photograph (40×) of the embryoid bodies induced to differentiate from mouse iPS (miPS) cells (22 days after the initiation of differentiation induction and 8 days after the initiation of adhesion culture).
FIG. 25B shows the results of expression analysis of retinal differentiation-associated transcription factors (Rx, Pax6, Chx10, Math5, Brn3a, and Brn3b) in the embryoid bodies conducted 14 days after the initiation of differentiation induction from mouse iPS (miPS) cells (at the time of the initiation of adhesion culture) via RT-PCR. The mRNA expression level is normalized to the HPRT1 expression level, and it is expressed relative to the mRNA expression level measured 0 days after the initiation of differentiation induction, which is designated 1.
Figure 25:
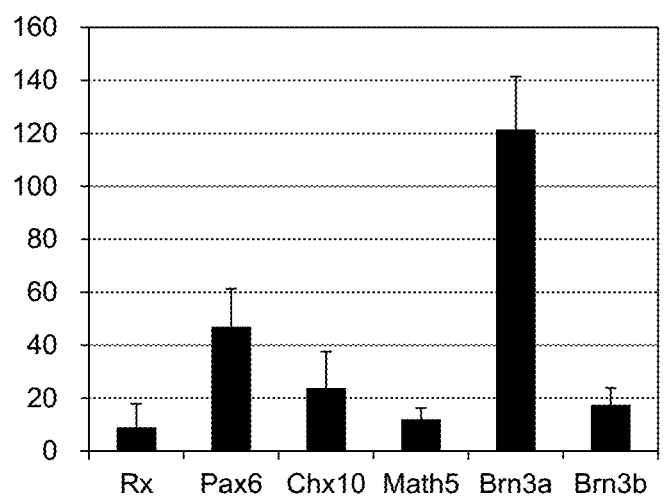

(Example 14) Preparation of Retinal Ganglion Cells from Mouse iPS Cells and Analysis Thereof Retinal ganglion cells were induced to differentiate from mouse iPS cells (obtained from the Riken BioResource Center (RIKEN BRC)) in the same manner as in Example 2, except that mouse iPS cells were used instead of mouse ES cells. However, adhesion culture was initiated 14 days after the initiation of differentiation induction, the cells were seeded on a 96-well plate at 4,000 cells/well, and Matrigel was added to the final concentration of 1.0% 1 day after the initiation of differentiation induction. FIG. 25A shows the stereomicroscopic image of embryoid bodies 22 days after the initiation of differentiation induction (8 days after the initiation of adhesion culture). When retinal ganglion cells were induced to differentiate from mouse iPS cells, axons radially developed from the margin of the embryoid bodies were observed. In addition, the expression levels of transcription factors associated with retinal differentiation (i.e., Rx, Pax6, Chx10, Math5, Brn3a, and Brn3b) were assayed 14 days after the initiation of differentiation induction (i.e., when adhesion culture was initiated) via real-time PCR with the use of the primers shown below under the same conditions as in Example 2. As a result, expression of all the transcription factors was detected, and the Brn3a expression level was higher than the Brn3b expression level when retinal ganglion cells were induced from mouse iPS cells (FIG. 25B).

Primer Set for Mouse Brn3b Gene Amplification

```
Forward primer:
                                       (SEQ ID NO: 7)
5'-ATCGTCTCCCAGAGTAAGAGC-3'

Reverse primer:
                                       (SEQ ID NO: 8)
5'-CACGGGATGGTGTTCATGG-3'
```

Primer Set for Mouse Rx Gene Amplification

```
Forward primer:
                                       (SEQ ID NO: 9)
5'-CGACGTTCACCACTTACCAA-3'

Reverse primer:
                                       (SEQ ID NO: 10)
5'-TCGGTTCTGGAACCATACCT-3'
```

Primer Set for Amplification of Mouse Pax6 Gene

```
Forward primer:
                                       (SEQ ID NO: 11)
5'-TACCAGTGTCTACCAGCCAAT-3'

Reverse primer:
                                       (SEQ ID NO: 12)
5'-TGCACGAGTATGAGGAGGTCT-3'
```

Primer Set for Mouse Chx10 Gene Amplification

```
Forward primer:
                                       (SEQ ID NO: 59)
5'-CGATTCCGAAGATGTTTCCTCC-3'

Reverse primer:
                                       (SEQ ID NO: 60)
5'-ATCTGGGTAGTGGGCTTCATT-3'
```

Primer Set for Mouse Math5 Gene Amplification

```
Forward primer:
                                       (SEQ ID NO: 61)
5'-ATCACCCCTACCTCCCTTTCC-3'

Reverse primer:
                                       (SEQ ID NO: 62)
5'-CGAAGAGCCTCTGCCCATA-3'
```

Primer Set for Mouse Brn3a Gene Amplification

```
Forward primer:
                                       (SEQ ID NO: 63)
5'-AGGCCTATTTTGCCGTACAA-3'

Reverse primer:
                                       (SEQ ID NO: 64)
5'-CGTCTCACACCCTCCTCAGT-3'
```

The axons of the retinal ganglion cells (RGCs) induced to differentiate from the mouse iPS cells described above and those of the retinal ganglion cells (RGCs) induced to differentiate from the mouse ES cells of Example 2 were analyzed in the manner described below.

(Observation of Axonal Transport)

Figure 26:
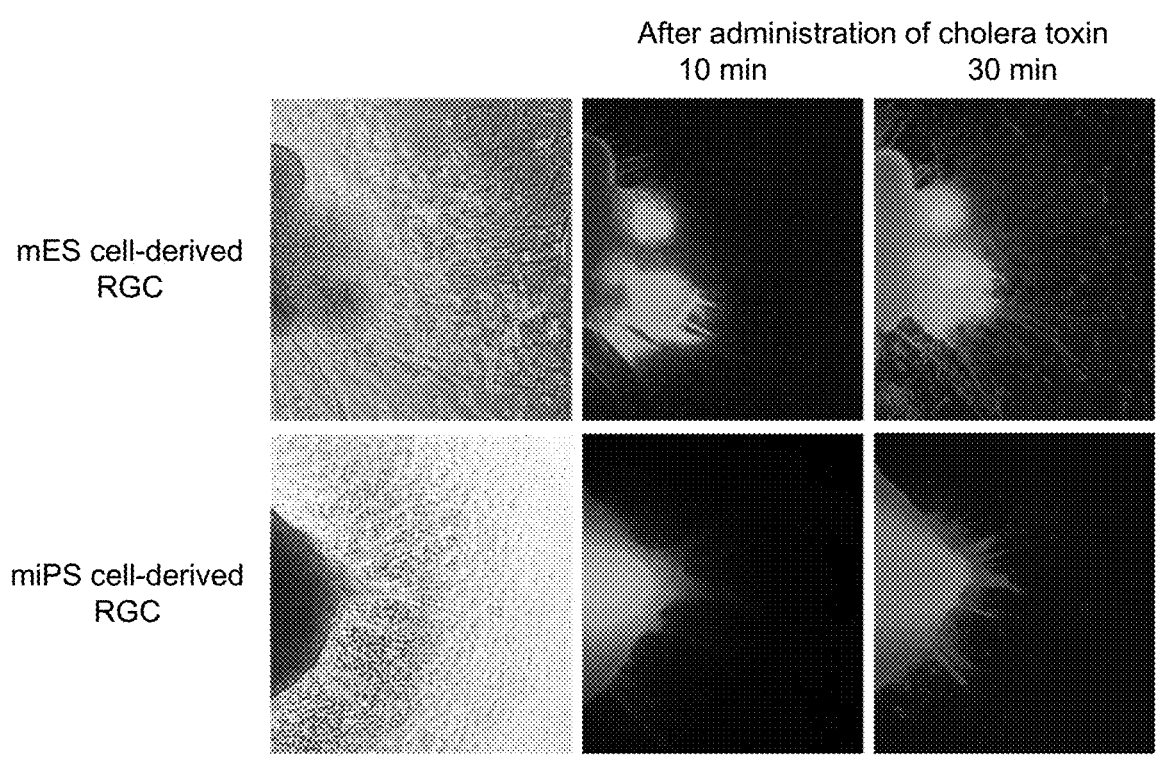
FIG. 26 shows the results of observation of the anterograde axonal flow of the retinal ganglion cells induced to differentiate from mouse ES (mES) cells or mouse iPS (miPS) cells (10 minutes and 30 minutes after the administration of cholera toxin into the center of the optic vesicle).

The time course of axonal transport was observed by injecting Alexa-Fluo-555 conjugated cholera toxin (Life Technologies) into the central region of the optic vesicle in the retinal ganglion cells (RGCs) induced to differentiate from mouse iPS cells or ES cells. Observation was carried out with the use of an IX71 inverted research microscope (Olympus Corporation). Time-lapse analysis was initiated immediately after the injection of cholera toxin with the use of DeltaVision ELITE (Comes Technologies Limited). Anterograde axonal transport was observed in both the RGCs induced to differentiate from mouse ES cells and the RGCs induced to differentiate from mouse iPS cells, and the injected cholera toxin was transported to the marginal region of axons by means of anterograde axonal transport (FIG. 26).

(Electrophysiological Recording)

Figure 27:
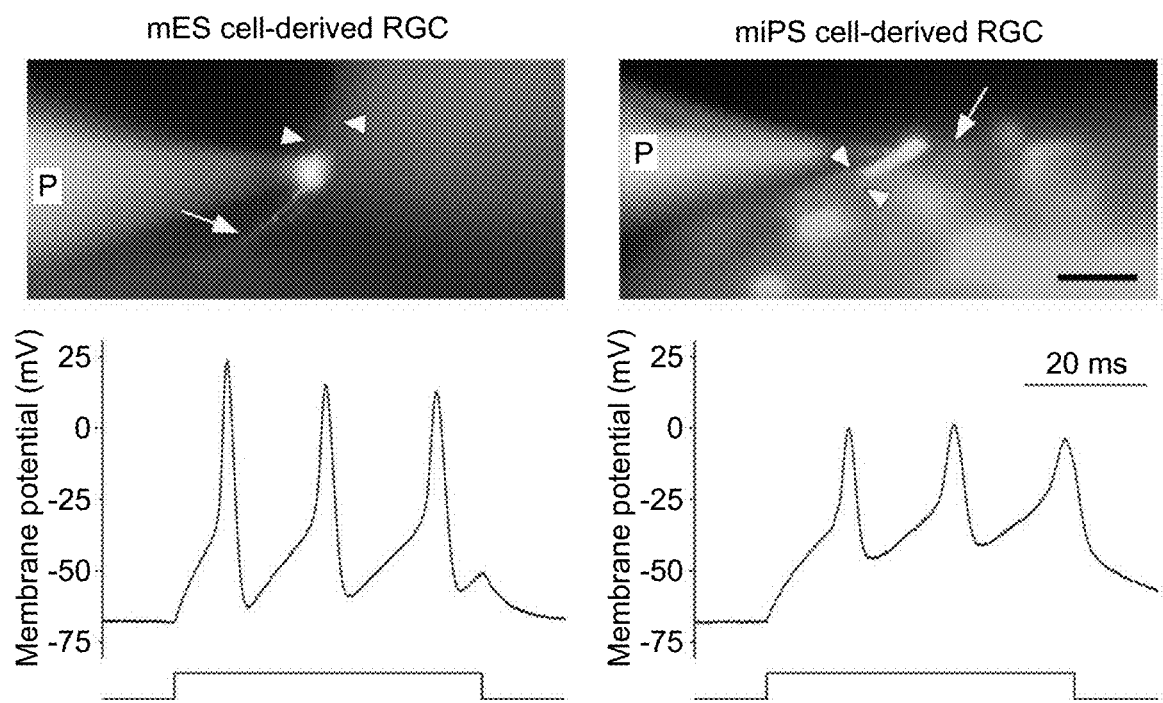
FIG. 27 shows microscopic photographs of retinal ganglion cells stained with Lucifer yellow CH (induced to differentiate from mouse ES (mES) cells or mouse iPS (miPS) cells) (triangular arrow: dendritic process; arrow: axonal process) and the records of action potentials (whole-cell recording: whole-cell recording).

Electrophysiological recording was carried out in the same manner as in Example 8 (2), except that the average membrane capacitance of RGCs (n=3) induced to differentiate from mouse iPS cells during the recordings was changed to 11±9.2 pF, and that of RGCs (n=3) induced to differentiate from mouse ES cells was changed to 12±5.7 pF. Both the RGCs induced to differentiate from mouse ES cells and the RGCs induced to differentiate from mouse iPS cells had long axon processes extending toward the filter paper side and possessed dendritic processes (FIG. 27, upper panel). In the electrophysiological analysis of cells with axonal process, action potentials were continuously exhibited in response to current injection through the recording pipette in the current clump mode (FIG. 27, lower panel).

Figure 28:
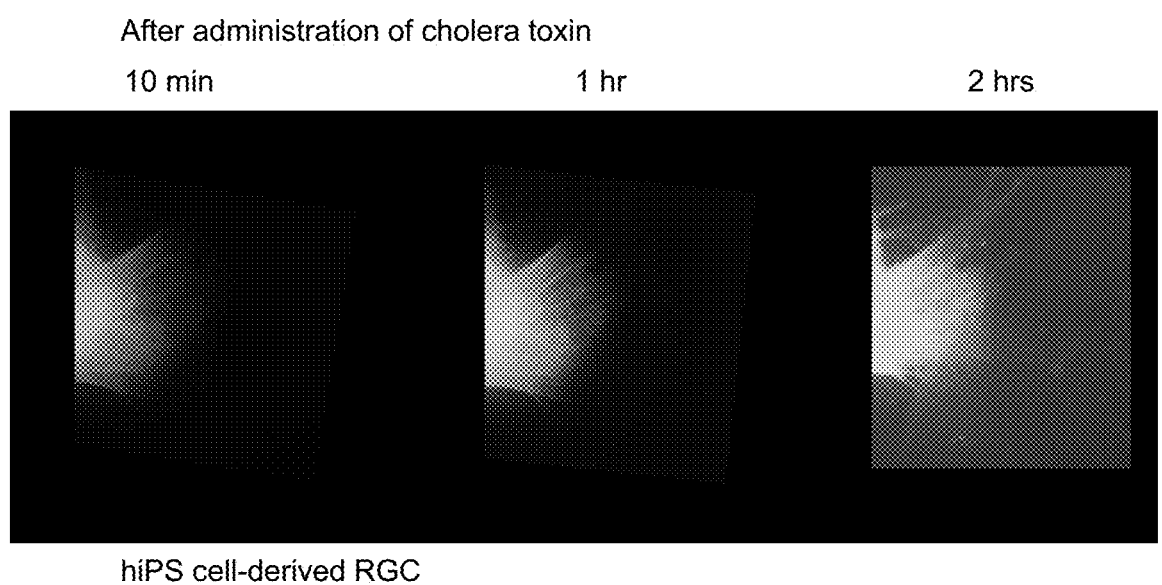
FIG. 28 shows the results of observation of the anterograde axonal flow of the retinal ganglion cells induced to differentiate from human iPS (hiPS) cells (10 minutes, 1 hour, and 2 hours after the administration of cholera toxin into the center of the optic vesicle).

(Example 15) Observation of Axonal Flow of Retinal Ganglion Cells Induced to Differentiate from Human iPS Cells The retinal ganglion cells (RGCs) induced to differentiate from human iPS cells in the same manner as in Example 1 were observed in terms of axonal transport in the same manner as in Example 14. The cholera toxin injected into the central region of the optic vesicle was transported to the marginal region of axons by means of anterograde axonal transport (FIG. 28).

Figure 29:
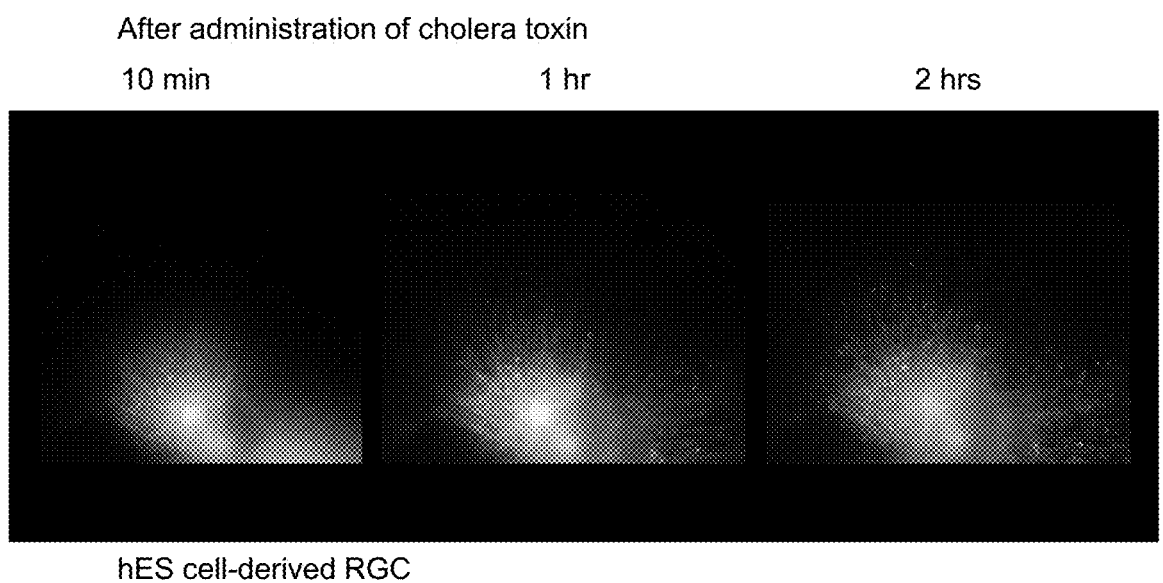
FIG. 29 shows the results of observation of the anterograde axonal flow of the retinal ganglion cells induced to differentiate from human ES (hES) cells (10 minutes, 1 hour, and 2 hours after the administration of cholera toxin into the center of the optic vesicle).
Figure 30:
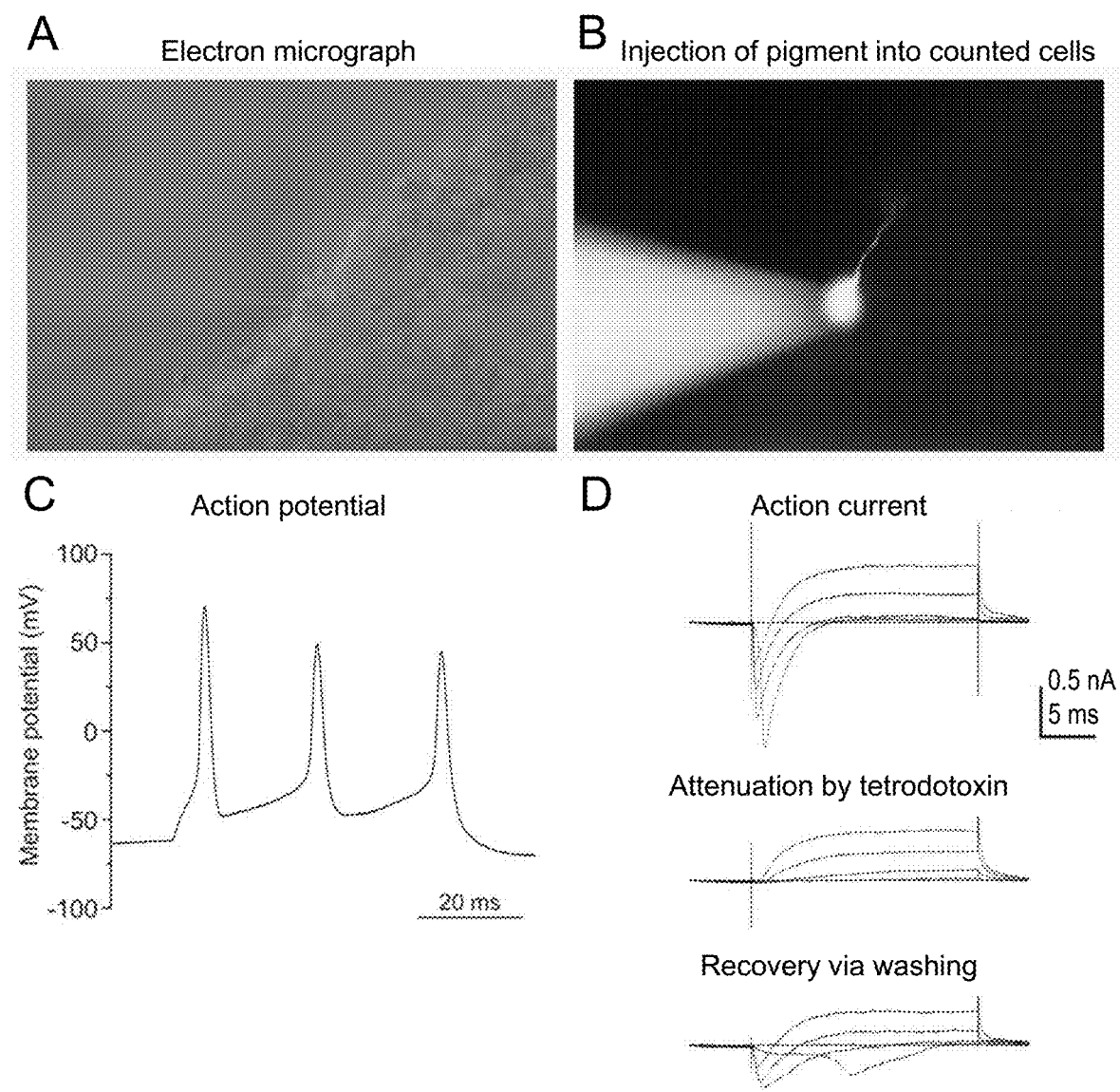
FIG. 30 shows the results of electrophysiological analysis of retinal ganglion cells induced to differentiate from human ES cells.

(Example 16) Observation and Electrophysiological Recording of Axonal Flow of Retinal Ganglion Cells Induced to Differentiate from Human ES Cells The retinal ganglion cells (RGCs) induced to differentiate from human ES cells in the same manner as in Example 13 were observed in terms of axonal transport in the same manner as in Example 14. The cholera toxin injected into the central region of the optic vesicle was transported to the marginal region of axons by means of anterograde axonal transport (FIG. 29). Electrophysiological recording was carried out in the same manner as in Example 8 (2). The RGCs induced to differentiate from human ES cells also had long axon processes extending toward the filter paper side and possessed dendritic processes (FIGS. 30A and 30B). In the electrophysiological analysis of cells with axonal processes, action potentials were continuously exhibited in response to current injection through the recording pipette in the current clump mode (FIG. 30C). The cells that generated action potentials first exhibited sensitivity to outward currents and then tetrodotoxin (TTX)-sensitivity (FIG. 30D).

(Example 17) Comparison and Examination of Conditions for Retinal Ganglion Cell Production Conditions for producing retinal ganglion cells (RGCs) from human iPS cells employed in Example 1 were changed, and differentiation induction and axon elongation were observed. Specifically, conditions in terms of the following were examined: the time to shift from floating culture to adhesion culture (18 days, 27 days, and 35 days after the initiation of differentiation induction); the amount of adhesion culture medium (250 μl, 400 μl); whether or not optic vesicles (OVs) were cleaved from embryoid bodies (EBs) at the time of adhesion culture; whether or not neurotrophic factors (BDNF) were added to the neuronal maintenance medium (+, −); whether or not retinoic acid (RA) was added to the neuronal maintenance medium (+, −); and oxygen concentration at the time of floating culture (high oxygen concentration: 40%; normal (indoor) oxygen concentration). The results are shown in FIGS. 31-1 and 31-2. In terms of differentiation into RGCs and the degree of axon elongation, more sufficient results were achieved under the culture conditions employed in Example 1 (i.e., adhesion was performed 27 days after the initiation of differentiation induction, in 250 μl of the medium, without the cleavage of optic vesicles (OVs), with the addition of BDNF (+), without the addition of RA (−), at the normal (indoor) oxygen concentration), compared with those achieved under conditions different therefrom (i.e., adhesion was performed 18 days and 35 days after the initiation of differentiation induction, in 400 μl of the medium, with the cleavage of optic vesicles (OVs), without the addition of BDNF (−), with the addition of RA (+), at the high oxygen concentration (40%)).

INDUSTRIAL APPLICABILITY

The present invention is applicable in the field of production of materials for regenerative medicine aimed at treatment of eye diseases involving retinal ganglion cell damage, such as glaucoma.

All publications, patents, and patent applications cited herein are incorporated herein by reference in their entirety.

The invention claimed is:

1. A method for producing retinal ganglion cells with elongated axons comprising:
 (a) subjecting pluripotent stem cells to floating culture to induce differentiation into retinal progenitor cells by floating culture;
 (b) subjecting the retinal progenitor cells obtained in step (a) to floating culture to induce differentiation into retinal ganglion cells by floating culture; and
 (c) allowing axons to elongate by adhesion culture of the retinal ganglion cells obtained in step (b).

2. The method according to claim 1, wherein the pluripotent stem cells are induced pluripotent stem cells (iPS cells) or embryonic stem cells (ES cells).

3. The method according to claim 1, wherein the adhesion culture is done in a medium containing neurotrophic factors.

4. The method according to claim 1, wherein the adhesion culture is done in a medium wherein the surface level of the medium is the same height or lower than the height of the cell mass adhered to the culture vessel.

* * * * *